US012420098B1

(12) United States Patent
Gliner

(10) Patent No.: US 12,420,098 B1
(45) Date of Patent: Sep. 23, 2025

(54) AUTONOMIC NERVOUS SYSTEM CONTROL VIA HIGH FREQUENCY SPINAL CORD MODULATION, AND ASSOCIATED SYSTEMS AND METHODS

(71) Applicant: Nevro Corp., Redwood City, CA (US)

(72) Inventor: Bradford Evan Gliner, Sammamish, WA (US)

(73) Assignee: Nevro Corp., Redwood City, CA (US)

( * ) Notice: Subject to any disclaimer, the term of this patent is extended or adjusted under 35 U.S.C. 154(b) by 504 days.

(21) Appl. No.: 17/579,811

(22) Filed: Jan. 20, 2022

Related U.S. Application Data

(63) Continuation of application No. 16/406,982, filed on May 8, 2019, now Pat. No. 11,247,057, which is a continuation of application No. 15/808,591, filed on Nov. 9, 2017, now Pat. No. 10,328,256, which is a continuation of application No. 13/922,765, filed on Jun. 20, 2013, now Pat. No. 9,833,614.

(60) Provisional application No. 61/663,466, filed on Jun. 22, 2012.

(51) Int. Cl.
*A61N 1/36* (2006.01)

(52) U.S. Cl.
CPC ..... *A61N 1/36139* (2013.01); *A61N 1/36062* (2017.08); *A61N 1/36171* (2013.01); *A61N 1/36071* (2013.01); *A61N 1/36121* (2013.01)

(58) Field of Classification Search
CPC ............... A61N 1/36139; A61N 1/36062
USPC ............................................... 607/117
See application file for complete search history.

(56) References Cited

U.S. PATENT DOCUMENTS

| | | |
|---|---|---|
| 1,597,061 A | 8/1926 | Cultra |
| 2,622,601 A | 12/1952 | Nemec |
| 3,195,540 A | 7/1965 | Waller |
| 3,724,467 A | 4/1973 | Avery et al. |
| 3,727,616 A | 4/1973 | Lenzkes |
| 3,817,254 A | 6/1974 | Maurer |
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,148,321 A | 4/1979 | Wyss et al. |

(Continued)

FOREIGN PATENT DOCUMENTS

| | | |
|---|---|---|
| DE | 10318071 A1 | 11/2004 |
| EP | 1181947 A2 | 2/2002 |

(Continued)

OTHER PUBLICATIONS

Cata et al., "Spinal cord stimulation relieves chemotherapy-induced pain: A Clinical Case Report," Journal of Pain and Symptom Management—10.1016/j.jpainsymman, vol. 27, No. 1, Jan. 2004, 7 pages.

(Continued)

*Primary Examiner* — Nadia A Mahmood

(57) ABSTRACT

Autonomic nervous system control via high frequency spinal cord modulation, and associated systems and methods. A method for treating a patient in accordance with a particular embodiment includes selecting a neural modulation site to include a neural population of the patient's spinal cord, and selecting parameters of a neural modulation signal to at least reduce an autonomic system deficit in the patient.

38 Claims, 11 Drawing Sheets

(56) References Cited

U.S. PATENT DOCUMENTS

| | | |
|---|---|---|
| 4,379,462 A | 4/1983 | Borkan et al. |
| 4,414,986 A | 11/1983 | Dickhudt et al. |
| 4,535,777 A | 8/1985 | Castel |
| 4,541,432 A | 9/1985 | Molina-Negro et al. |
| 4,608,985 A | 9/1986 | Crish et al. |
| 4,612,934 A | 9/1986 | Borkan et al. |
| 4,649,935 A | 3/1987 | Charmillot et al. |
| 4,735,204 A | 4/1988 | Sussman et al. |
| 4,764,132 A | 8/1988 | Stutz, Jr. |
| 4,793,353 A | 12/1988 | Borkan et al. |
| 4,841,973 A | 6/1989 | Stecker |
| RE33,420 E | 11/1990 | Sussman et al. |
| 5,002,053 A | 3/1991 | Garcia-Rill |
| 5,335,657 A | 8/1994 | Terry, Jr. et al. |
| 5,354,320 A | 10/1994 | Schaldach et al. |
| 5,514,175 A | 5/1996 | Kim et al. |
| 5,540,734 A | 7/1996 | Zabara |
| 5,562,717 A | 10/1996 | Tippey et al. |
| 5,643,330 A | 7/1997 | Holsheimer et al. |
| 5,716,377 A | 2/1998 | Rise et al. |
| 5,755,758 A | 5/1998 | Wolozko |
| 5,776,170 A | 7/1998 | MacDonald et al. |
| 5,830,151 A | 11/1998 | Hadzic et al. |
| 5,853,373 A | 12/1998 | Griffith et al. |
| 5,893,883 A | 4/1999 | Torgerson et al. |
| 5,938,690 A | 8/1999 | Law |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,049,701 A | 4/2000 | Sparksman |
| 6,161,044 A | 12/2000 | Silverstone |
| 6,161,048 A | 12/2000 | Sluijter et al. |
| 6,167,311 A | 12/2000 | Rezai |
| 6,176,242 B1 | 1/2001 | Rise |
| 6,233,488 B1 | 5/2001 | Hess |
| 6,238,423 B1 | 5/2001 | Bardy |
| 6,246,912 B1 | 6/2001 | Sluijter et al. |
| 6,319,241 B1 | 11/2001 | King et al. |
| 6,341,236 B1 | 1/2002 | Osorio et al. |
| 6,356,786 B1 | 3/2002 | Rezai et al. |
| 6,366,814 B1 | 4/2002 | Boveja |
| 6,393,325 B1 | 5/2002 | Mann et al. |
| 6,397,108 B1 | 5/2002 | Camps et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,473,644 B1 | 10/2002 | Terry, Jr. et al. |
| 6,505,078 B1 | 1/2003 | King et al. |
| 6,510,347 B2 | 1/2003 | Borkan |
| 6,516,227 B1 | 2/2003 | Meadows et al. |
| 6,526,318 B1 | 2/2003 | Ansarinia |
| 6,571,127 B1 | 5/2003 | Ben-Haim et al. |
| 6,584,358 B2 | 6/2003 | Carter et al. |
| 6,609,030 B1 | 8/2003 | Rezai et al. |
| 6,622,048 B1 | 9/2003 | Mann et al. |
| 6,659,968 B1 | 12/2003 | McClure |
| 6,662,051 B1 | 12/2003 | Eraker et al. |
| 6,714,822 B2 | 3/2004 | King et al. |
| 6,721,603 B2 | 4/2004 | Zabara et al. |
| 6,795,737 B2 | 9/2004 | Gielen et al. |
| 6,856,315 B2 | 2/2005 | Eberlein |
| 6,871,090 B1 | 3/2005 | He et al. |
| 6,871,099 B1 | 3/2005 | Whitehurst et al. |
| 6,885,888 B2 | 4/2005 | Rezai |
| 6,907,295 B2 | 6/2005 | Gross et al. |
| 6,923,784 B2 | 8/2005 | Stein |
| 6,928,320 B2 | 8/2005 | King |
| 6,950,707 B2 | 9/2005 | Whitehurst |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,054,686 B2 | 5/2006 | MacDonald |
| 7,082,333 B1 | 7/2006 | Bauhahn et al. |
| 7,117,034 B2 | 10/2006 | Kronberg |
| 7,146,224 B2 | 12/2006 | King |
| 7,149,574 B2 | 12/2006 | Yun et al. |
| 7,162,304 B1 | 1/2007 | Bradley |
| 7,167,750 B2 | 1/2007 | Knudson et al. |
| 7,174,215 B2 | 2/2007 | Bradley |
| 7,177,702 B2 | 2/2007 | Wallace et al. |
| 7,180,760 B2 | 2/2007 | Varrichio et al. |
| 7,206,640 B1 | 4/2007 | Overstreet |
| 7,212,865 B2 | 5/2007 | Cory |
| 7,225,035 B2 | 5/2007 | Brabec et al. |
| 7,236,822 B2 | 6/2007 | Dobak, III |
| 7,239,912 B2 | 7/2007 | Dobak, III |
| 7,252,090 B2 | 8/2007 | Goetz |
| 7,260,436 B2 | 8/2007 | Kilgore et al. |
| 7,266,412 B2 | 9/2007 | Stypulkowski |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,346,398 B2 | 3/2008 | Gross et al. |
| 7,349,743 B2 | 3/2008 | Tadlock |
| RE40,279 E | 4/2008 | Sluijter et al. |
| 7,359,751 B1 | 4/2008 | Erickson et al. |
| 7,363,076 B2 | 4/2008 | Yun et al. |
| 7,389,145 B2 | 6/2008 | Kilgore et al. |
| 7,393,351 B2 | 7/2008 | Woloszko et al. |
| 7,463,927 B1 | 12/2008 | Chaouat |
| 7,483,747 B2 | 1/2009 | Gliner et al. |
| 7,493,172 B2 | 2/2009 | Whitehurst et al. |
| 7,502,652 B2 | 3/2009 | Gaunt et al. |
| 7,571,007 B2 | 8/2009 | Erickson et al. |
| 7,580,753 B2 | 8/2009 | Kim et al. |
| 7,599,737 B2 | 10/2009 | Yomtov et al. |
| 7,634,317 B2 | 12/2009 | Ben-David et al. |
| 7,676,269 B2 | 3/2010 | Yun et al. |
| 7,689,276 B2 | 3/2010 | Dobak |
| 7,689,289 B2 | 3/2010 | King |
| 7,715,915 B1 | 5/2010 | Rye et al. |
| 7,734,340 B2 | 6/2010 | De Ridder |
| 7,734,355 B2 | 6/2010 | Cohen et al. |
| 7,742,810 B2 | 6/2010 | Moffitt et al. |
| 7,761,170 B2 | 7/2010 | Kaplan et al. |
| 7,778,704 B2 | 8/2010 | Rezai |
| 7,813,803 B2 | 10/2010 | Heruth et al. |
| 7,826,901 B2 | 11/2010 | Lee et al. |
| 7,853,322 B2 | 12/2010 | Bourget et al. |
| 7,860,570 B2 | 12/2010 | Whitehurst et al. |
| 7,865,243 B1 | 1/2011 | Whitehurst et al. |
| 7,877,136 B1 | 1/2011 | Moffitt et al. |
| 7,877,146 B2 | 1/2011 | Rezai |
| 7,881,805 B2 | 2/2011 | Bradley |
| 7,890,176 B2 | 2/2011 | Jaax et al. |
| 7,890,182 B2 | 2/2011 | Parramon et al. |
| 7,914,452 B2 | 3/2011 | Hartley et al. |
| 7,933,654 B2 | 4/2011 | Merfeld et al. |
| 7,937,145 B2 | 5/2011 | Dobak |
| 8,000,794 B2 | 8/2011 | Lozano |
| 8,010,198 B2 | 8/2011 | Libbus et al. |
| 8,027,718 B2 | 9/2011 | Spinner et al. |
| 8,046,075 B2 | 10/2011 | Rezai |
| 8,060,208 B2 | 11/2011 | Kilgore et al. |
| 8,082,039 B2 | 12/2011 | Kim et al. |
| 8,170,675 B2 | 5/2012 | Alataris et al. |
| 8,209,021 B2 | 6/2012 | Alataris et al. |
| 8,209,028 B2 | 6/2012 | Skelton et al. |
| 8,224,453 B2 | 7/2012 | De Ridder |
| 8,224,459 B1 | 7/2012 | Pianca et al. |
| 8,255,057 B2 | 8/2012 | Fang |
| 8,280,515 B2 | 10/2012 | Greenspan |
| 8,340,775 B1 | 12/2012 | Cullen et al. |
| 8,355,792 B2 | 1/2013 | Alataris et al. |
| 8,355,797 B2 | 1/2013 | Caparso |
| 8,359,102 B2 | 1/2013 | Alataris et al. |
| 8,359,103 B2 | 1/2013 | Alataris et al. |
| 8,364,271 B2 | 1/2013 | De Ridder |

(56) References Cited

U.S. PATENT DOCUMENTS

| | | |
|---|---|---|
| 8,364,273 B2 | 1/2013 | De Ridder |
| 8,396,559 B2 | 3/2013 | Alataris et al. |
| 8,423,147 B2 | 4/2013 | Alataris et al. |
| 8,428,735 B2 | 4/2013 | Littlewood et al. |
| 8,428,748 B2 | 4/2013 | Alataris et al. |
| 8,467,875 B2 | 6/2013 | Bennett et al. |
| 8,569,935 B1 | 10/2013 | Kosierkiewicz |
| 8,612,018 B2 | 12/2013 | Gillbe |
| 8,649,874 B2 | 2/2014 | Alataris et al. |
| 8,666,506 B2 | 3/2014 | King |
| 8,712,533 B2 | 4/2014 | Alataris |
| 8,751,009 B2 | 6/2014 | Wacnik |
| 8,767,469 B2 | 7/2014 | Tweden et al. |
| 8,768,469 B2 | 7/2014 | Tweden et al. |
| 8,768,472 B2 | 7/2014 | Fang |
| 8,825,166 B2 | 9/2014 | John |
| 8,886,326 B2 | 11/2014 | Alataris et al. |
| 8,886,328 B2 | 11/2014 | Alataris et al. |
| 8,892,209 B2 | 11/2014 | Alataris et al. |
| 8,903,501 B2 | 12/2014 | Perryman et al. |
| 8,918,172 B2 | 12/2014 | Moffitt et al. |
| 8,918,190 B2 | 12/2014 | Libbus et al. |
| 8,923,990 B2 | 12/2014 | Libbus et al. |
| 8,954,153 B2 | 2/2015 | Boggs, II |
| 9,002,459 B2 | 4/2015 | Lee et al. |
| 9,002,477 B2 | 4/2015 | Burnett |
| 9,026,226 B2 | 5/2015 | Gerber et al. |
| 9,061,153 B1 | 6/2015 | Lebovitz et al. |
| 9,067,076 B2 | 6/2015 | Nolan et al. |
| 9,168,000 B2 | 10/2015 | Dunki-Jacobs |
| 9,180,298 B2 | 11/2015 | Alataris et al. |
| 9,295,840 B1 | 3/2016 | Thacker |
| 9,295,841 B2 | 3/2016 | Fang et al. |
| 9,327,121 B2 | 5/2016 | Thacker |
| 9,327,127 B2 | 5/2016 | Alataris et al. |
| 9,381,356 B2 | 7/2016 | Parker |
| 9,387,338 B2 | 7/2016 | Burnett |
| 9,452,286 B2 | 9/2016 | Cowan et al. |
| 9,480,846 B2 | 11/2016 | Strother |
| 9,486,632 B2 | 11/2016 | Saab |
| 9,486,633 B2 | 11/2016 | Kramer et al. |
| 9,533,149 B2 | 1/2017 | Lee et al. |
| 9,561,370 B2 | 2/2017 | Rezai |
| 9,561,371 B2 | 2/2017 | Elborno |
| 9,630,011 B2 | 4/2017 | Lipani |
| 9,724,511 B2 | 8/2017 | Wei et al. |
| 9,757,584 B2 | 9/2017 | Burnett et al. |
| 9,782,589 B2 | 10/2017 | Oron et al. |
| 9,789,313 B2 | 10/2017 | Lipani |
| 9,833,614 B1 | 12/2017 | Gliner |
| 9,861,547 B2 | 1/2018 | Crunick et al. |
| 9,884,189 B2 | 2/2018 | Boggs, II |
| 9,895,530 B2 | 2/2018 | Boggs, II |
| 9,895,532 B2 | 2/2018 | Kaula et al. |
| 9,895,539 B1 | 2/2018 | Heit et al. |
| 9,950,164 B2 | 4/2018 | Lipani |
| 9,981,131 B2 | 5/2018 | Kent |
| 10,143,850 B2 | 12/2018 | Cowan et al. |
| 10,159,837 B2 | 12/2018 | Lee |
| 10,207,110 B1 | 2/2019 | Gelfand |
| 10,232,180 B2 | 3/2019 | Kramer et al. |
| 10,238,872 B2 | 3/2019 | Pivonka et al. |
| 10,307,585 B2 | 6/2019 | Boggs et al. |
| 10,328,256 B1 | 6/2019 | Gliner |
| 10,342,977 B2 | 7/2019 | Raghunathan |
| 10,369,366 B2 | 8/2019 | Oron et al. |
| 10,426,959 B2 | 10/2019 | Boggs, II |
| 10,493,275 B2 | 12/2019 | Alataris et al. |
| 10,583,284 B2 | 3/2020 | Peters et al. |
| 10,668,285 B2 | 6/2020 | Boggs, II |
| 10,799,701 B2 | 10/2020 | Lee |
| 11,247,057 B1 | 2/2022 | Gliner |
| 11,534,611 B2 | 12/2022 | Baldoni |
| 12,220,580 B2 | 2/2025 | Dawson |
| 12,226,634 B2 | 2/2025 | Subbaroyan |
| 2002/0055779 A1 | 5/2002 | Andrews |
| 2002/0128700 A1 | 9/2002 | Cross |
| 2003/0018367 A1 | 1/2003 | DiLorenzo |
| 2003/0055464 A1 | 3/2003 | Darvish et al. |
| 2003/0100931 A1 | 5/2003 | Mullett |
| 2003/0120323 A1 | 6/2003 | Meadows et al. |
| 2004/0015202 A1 | 1/2004 | Chandler et al. |
| 2004/0015204 A1 | 1/2004 | Whitehurst |
| 2004/0034394 A1 | 2/2004 | Woods et al. |
| 2004/0039425 A1 | 2/2004 | Greenwood-Van Meerveld |
| 2004/0059395 A1 | 3/2004 | North et al. |
| 2004/0073273 A1 | 4/2004 | Gluckman et al. |
| 2004/0093093 A1 | 5/2004 | Andrews |
| 2004/0116977 A1 | 6/2004 | Finch et al. |
| 2004/0122477 A1 | 6/2004 | Whitehorse |
| 2004/0162590 A1 | 8/2004 | Whitehurst et al. |
| 2004/0167584 A1 | 8/2004 | Carroll et al. |
| 2004/0186532 A1 | 9/2004 | Tadlock |
| 2004/0193228 A1 | 9/2004 | Gerber |
| 2004/0210270 A1 | 10/2004 | Erickson |
| 2004/0210271 A1 | 10/2004 | Campen et al. |
| 2004/0267330 A1 | 12/2004 | Lee et al. |
| 2005/0021104 A1 | 1/2005 | DiLorenzo |
| 2005/0033381 A1 | 2/2005 | Carter et al. |
| 2005/0038489 A1 | 2/2005 | Grill |
| 2005/0060001 A1 | 3/2005 | Singhal et al. |
| 2005/0070982 A1 | 3/2005 | Heruth et al. |
| 2005/0075701 A1 | 4/2005 | Shafer |
| 2005/0075702 A1 | 4/2005 | Shafer |
| 2005/0113877 A1 | 5/2005 | Spinelli et al. |
| 2005/0113878 A1 | 5/2005 | Gerber |
| 2005/0113882 A1 | 5/2005 | Cameron et al. |
| 2005/0119713 A1 | 6/2005 | Whitehurst et al. |
| 2005/0143789 A1 | 6/2005 | Whitehurst et al. |
| 2005/0149148 A1 | 7/2005 | King |
| 2005/0153885 A1 | 7/2005 | Yun et al. |
| 2005/0154435 A1 | 7/2005 | Stern et al. |
| 2005/0209655 A1 | 9/2005 | Bradley |
| 2005/0240241 A1 | 10/2005 | Yun et al. |
| 2005/0245978 A1 | 11/2005 | Varrichio et al. |
| 2005/0245987 A1 | 11/2005 | Woods |
| 2005/0246006 A1 | 11/2005 | Daniels |
| 2005/0267545 A1 | 12/2005 | Cory |
| 2005/0278000 A1 | 12/2005 | Strother et al. |
| 2005/0288721 A1 | 12/2005 | Girouard |
| 2006/0004422 A1 | 1/2006 | De Ridder |
| 2006/0009820 A1 | 1/2006 | Royle |
| 2006/0015153 A1 | 1/2006 | Gliner et al. |
| 2006/0030895 A1 | 2/2006 | Simon et al. |
| 2006/0041285 A1 | 2/2006 | Johnson |
| 2006/0047325 A1 | 3/2006 | Thimineur |
| 2006/0074456 A1 | 4/2006 | Pyles et al. |
| 2006/0079937 A1 | 4/2006 | King et al. |
| 2006/0095088 A1 | 5/2006 | De Ridder |
| 2006/0100671 A1 | 5/2006 | Ridder |
| 2006/0149337 A1 | 7/2006 | John |
| 2006/0161219 A1 | 7/2006 | Mock et al. |
| 2006/0161235 A1 | 7/2006 | King |
| 2006/0167525 A1 | 7/2006 | King |
| 2006/0168805 A1 | 8/2006 | Hegland et al. |
| 2006/0190044 A1 | 8/2006 | Libbus et al. |
| 2006/0190048 A1 | 8/2006 | Gerber |
| 2006/0224187 A1 | 10/2006 | Bradley et al. |
| 2006/0229687 A1 | 10/2006 | Goetz et al. |
| 2006/0253182 A1 | 11/2006 | King |
| 2006/0271108 A1 | 11/2006 | Libbus et al. |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0043400 A1 | 2/2007 | Donders et al. |
| 2007/0049988 A1 | 3/2007 | Carbunaru |
| 2007/0049991 A1 | 3/2007 | Klostermann et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson |
| 2007/0083240 A1 | 4/2007 | Peterson et al. |
| 2007/0106337 A1 | 5/2007 | Errico et al. |
| 2007/0106342 A1 | 5/2007 | Schumann |

(56) References Cited

U.S. PATENT DOCUMENTS

| | | |
|---|---|---|
| 2007/0150029 A1 | 6/2007 | Bourget et al. |
| 2007/0150034 A1 | 6/2007 | Rooney et al. |
| 2007/0156183 A1 | 7/2007 | Rhodes |
| 2007/0156201 A1 | 7/2007 | Rossing |
| 2007/0167992 A1 | 7/2007 | Carley |
| 2007/0179559 A1 | 8/2007 | Giftakis et al. |
| 2007/0179579 A1 | 8/2007 | Feler et al. |
| 2007/0203537 A1 | 8/2007 | Goetz et al. |
| 2007/0213789 A1 | 9/2007 | Nolan et al. |
| 2007/0239226 A1 | 10/2007 | Overstreet |
| 2007/0244522 A1 | 10/2007 | Overstreet |
| 2007/0255118 A1 | 11/2007 | Miesel et al. |
| 2007/0265681 A1 | 11/2007 | Gerber et al. |
| 2007/0293893 A1 | 12/2007 | Stolen et al. |
| 2007/0299482 A1 | 12/2007 | Littlewood et al. |
| 2008/0033511 A1* | 2/2008 | Dobak ............... A61N 1/3605 607/66 |
| 2008/0065158 A1 | 3/2008 | Ben-Ezra |
| 2008/0077192 A1 | 3/2008 | Harry et al. |
| 2008/0086036 A1 | 4/2008 | Hartley |
| 2008/0097539 A1 | 4/2008 | Belalcazar |
| 2008/0103570 A1 | 5/2008 | Gerber |
| 2008/0167697 A1 | 7/2008 | Johnson |
| 2008/0183259 A1 | 7/2008 | Bly et al. |
| 2008/0234791 A1 | 9/2008 | Arle et al. |
| 2008/0269854 A1 | 10/2008 | Hegland et al. |
| 2008/0281381 A1 | 11/2008 | Gerber et al. |
| 2008/0319511 A1 | 12/2008 | Pless |
| 2009/0018617 A1 | 1/2009 | Skelton et al. |
| 2009/0024187 A1 | 1/2009 | Erickson et al. |
| 2009/0036945 A1 | 2/2009 | Chancellor et al. |
| 2009/0054962 A1 | 2/2009 | Lefler et al. |
| 2009/0069803 A1 | 3/2009 | Starkebaum |
| 2009/0076565 A1 | 3/2009 | Surwit |
| 2009/0112282 A1 | 4/2009 | Kast et al. |
| 2009/0118777 A1 | 5/2009 | Iki |
| 2009/0125079 A1 | 5/2009 | Armstrong et al. |
| 2009/0132010 A1 | 5/2009 | Kronberg |
| 2009/0132016 A1 | 5/2009 | Putz |
| 2009/0157141 A1 | 6/2009 | Chiao et al. |
| 2009/0157149 A1 | 6/2009 | Wahlgren et al. |
| 2009/0196472 A1 | 8/2009 | Goetz et al. |
| 2009/0198306 A1 | 8/2009 | Goetz et al. |
| 2009/0204173 A1 | 8/2009 | Fang et al. |
| 2009/0204192 A1 | 8/2009 | Carlton et al. |
| 2009/0281595 A1 | 11/2009 | King et al. |
| 2009/0287274 A1 | 11/2009 | De Ridder |
| 2009/0287279 A1 | 11/2009 | Parramon et al. |
| 2009/0326611 A1 | 12/2009 | Gillbe |
| 2010/0010567 A1 | 1/2010 | Deem et al. |
| 2010/0016929 A1 | 1/2010 | Prochazka |
| 2010/0036454 A1 | 2/2010 | Bennett et al. |
| 2010/0042193 A1 | 2/2010 | Slavin |
| 2010/0057178 A1 | 3/2010 | Simon |
| 2010/0094375 A1 | 4/2010 | Donders et al. |
| 2010/0125313 A1 | 5/2010 | Lee et al. |
| 2010/0137938 A1 | 6/2010 | Kishawi |
| 2010/0152817 A1 | 6/2010 | Gillbe |
| 2010/0191307 A1 | 7/2010 | Fang et al. |
| 2010/0197708 A1 | 8/2010 | Talley |
| 2010/0241190 A1 | 9/2010 | Kilgore et al. |
| 2010/0249875 A1 | 9/2010 | Kishawi et al. |
| 2010/0256696 A1 | 10/2010 | Schleicher et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1* | 10/2010 | Chitre ............... A61N 1/36164 607/72 |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0009927 A1 | 1/2011 | Parker et al. |
| 2011/0022114 A1 | 1/2011 | Navarro |
| 2011/0040291 A1 | 2/2011 | Weissenrieder-Norlin et al. |
| 2011/0184301 A1 | 7/2011 | Holmstrom et al. |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0016437 A1 | 1/2012 | Alataris et al. |
| 2012/0016438 A1 | 1/2012 | Alataris et al. |
| 2012/0016439 A1 | 1/2012 | Alataris et al. |
| 2012/0016453 A1 | 1/2012 | Feler |
| 2012/0089200 A1 | 4/2012 | Ranu et al. |
| 2012/0150252 A1 | 6/2012 | Feldman et al. |
| 2012/0203304 A1 | 8/2012 | Alataris et al. |
| 2012/0209349 A1 | 8/2012 | Alataris et al. |
| 2012/0277833 A1 | 11/2012 | Gerber et al. |
| 2012/0283797 A1 | 11/2012 | De Ridder |
| 2012/0303098 A1 | 11/2012 | Perryman |
| 2013/0006325 A1 | 1/2013 | Woods et al. |
| 2013/0023951 A1 | 1/2013 | Greenspan |
| 2013/0041425 A1 | 2/2013 | Fang et al. |
| 2013/0066411 A1 | 3/2013 | Thacker |
| 2013/0096643 A1 | 4/2013 | Fang et al. |
| 2013/0096644 A1 | 4/2013 | Fang et al. |
| 2013/0110196 A1 | 5/2013 | Alataris et al. |
| 2013/0123879 A1 | 5/2013 | Alataris et al. |
| 2013/0172955 A1 | 7/2013 | Alataris |
| 2013/0204173 A1 | 8/2013 | Kelly et al. |
| 2013/0204320 A1 | 8/2013 | Alataris et al. |
| 2013/0204321 A1 | 8/2013 | Alataris et al. |
| 2013/0204322 A1 | 8/2013 | Alataris et al. |
| 2013/0204323 A1 | 8/2013 | Thacker et al. |
| 2013/0204324 A1 | 8/2013 | Thacker et al. |
| 2013/0204338 A1 | 8/2013 | Alataris et al. |
| 2013/0211487 A1 | 8/2013 | Fang et al. |
| 2013/0237948 A1 | 9/2013 | Donders |
| 2013/0261695 A1 | 10/2013 | Thacker et al. |
| 2013/0261696 A1 | 10/2013 | Alataris et al. |
| 2013/0261697 A1 | 10/2013 | Alataris et al. |
| 2013/0274846 A1 | 10/2013 | Lad et al. |
| 2014/0031896 A1 | 1/2014 | Alataris et al. |
| 2014/0046407 A1 | 2/2014 | Ben-Ezra |
| 2014/0142656 A1 | 5/2014 | Alataris et al. |
| 2014/0142657 A1 | 5/2014 | Alataris et al. |
| 2014/0142658 A1 | 5/2014 | Alataris et al. |
| 2014/0142659 A1 | 5/2014 | Alataris et al. |
| 2014/0142673 A1 | 5/2014 | Alataris et al. |
| 2014/0316484 A1 | 10/2014 | Edgerton |
| 2014/0343622 A1 | 11/2014 | Alataris et al. |
| 2014/0379044 A1 | 12/2014 | Walker et al. |
| 2015/0012079 A1 | 1/2015 | Goroszeniuk et al. |
| 2015/0018896 A1 | 1/2015 | Alataris et al. |
| 2015/0032181 A1 | 1/2015 | Baynham |
| 2015/0032182 A1 | 1/2015 | Alataris et al. |
| 2015/0032183 A1 | 1/2015 | Alataris et al. |
| 2015/0039040 A1 | 2/2015 | Cowan et al. |
| 2015/0039049 A1 | 2/2015 | Alataris et al. |
| 2015/0039050 A1 | 2/2015 | Alataris et al. |
| 2015/0045853 A1 | 2/2015 | Alataris et al. |
| 2015/0045854 A1 | 2/2015 | Alataris et al. |
| 2015/0051664 A1 | 2/2015 | Alataris et al. |
| 2015/0073510 A1 | 3/2015 | Perryman |
| 2015/0217114 A1 | 8/2015 | Parker |
| 2015/0217116 A1 | 8/2015 | Parramon et al. |
| 2015/0343220 A1 | 12/2015 | Alataris et al. |
| 2016/0030408 A1 | 2/2016 | Levin |
| 2016/0074663 A1 | 3/2016 | De Ridder |
| 2016/0121109 A1 | 5/2016 | Edgerton |
| 2016/0121119 A1 | 5/2016 | Alataris et al. |
| 2016/0177298 A1 | 6/2016 | Green |
| 2016/0184262 A1 | 6/2016 | Bollyky |
| 2016/0213918 A1 | 7/2016 | Howard et al. |
| 2016/0256683 A1 | 9/2016 | Butera et al. |
| 2016/0263376 A1 | 9/2016 | Yoo et al. |
| 2016/0287872 A1 | 10/2016 | Alataris et al. |
| 2016/0287873 A1 | 10/2016 | Alataris et al. |

(56) References Cited

U.S. PATENT DOCUMENTS

| | | |
|---|---|---|
| 2016/0287874 A1 | 10/2016 | Alataris et al. |
| 2016/0287875 A1 | 10/2016 | Thacker et al. |
| 2016/0287888 A1 | 10/2016 | Alataris et al. |
| 2016/0303374 A1 | 10/2016 | Alataris et al. |
| 2016/0367812 A1 | 12/2016 | De Ridder |
| 2017/0050021 A1 | 2/2017 | Cosman, Sr. |
| 2017/0095667 A1 | 4/2017 | Yakovlev |
| 2017/0095669 A1 | 4/2017 | Libbus et al. |
| 2017/0165485 A1 | 6/2017 | Sullivan et al. |
| 2017/0173335 A1 | 6/2017 | Min |
| 2017/0209699 A1 | 7/2017 | Thacker |
| 2017/0259065 A1 | 9/2017 | Baru |
| 2017/0274212 A1 | 9/2017 | Kramer et al. |
| 2017/0354831 A1 | 12/2017 | Burnett et al. |
| 2018/0000347 A1 | 1/2018 | Perez |
| 2018/0078754 A1 | 3/2018 | Perez |
| 2018/0085580 A1 | 3/2018 | Perez et al. |
| 2018/0110561 A1 | 4/2018 | Levin |
| 2018/0125689 A1 | 5/2018 | Perez |
| 2018/0256906 A1 | 9/2018 | Pivonka |
| 2018/0272132 A1 | 9/2018 | Subbaroyan |
| 2018/0280691 A1 | 10/2018 | Ackermann |
| 2018/0318585 A1 | 11/2018 | Pfeifer |
| 2018/0345020 A1 | 12/2018 | Ironi et al. |
| 2018/0361154 A1 | 12/2018 | Levin |
| 2019/0001139 A1 | 1/2019 | Mishra et al. |
| 2019/0046795 A1 | 2/2019 | Cakmak |
| 2019/0151652 A1 | 5/2019 | Boggs, II |
| 2019/0232062 A1 | 8/2019 | Falowski |
| 2019/0269913 A1 | 9/2019 | Pivonka et al. |
| 2019/0290900 A1 | 9/2019 | Esteller |
| 2019/0321641 A1 | 10/2019 | Baldoni |
| 2019/0336776 A1 | 11/2019 | Cowan et al. |
| 2019/0351235 A1 | 11/2019 | Leuthardt et al. |
| 2019/0374776 A1 | 12/2019 | Mishra et al. |
| 2020/0030606 A1 | 1/2020 | Boggs, II |
| 2020/0046973 A1 | 2/2020 | Simon et al. |
| 2020/0046981 A1 | 2/2020 | Kramer et al. |
| 2020/0108251 A1 | 4/2020 | Raghunathan |
| 2020/0139138 A1 | 5/2020 | Sit et al. |
| 2020/0289822 A1 | 9/2020 | Baynham |
| 2020/0324113 A1 | 10/2020 | Fisher |
| 2020/0353253 A1 | 11/2020 | Subbaroyan et al. |
| 2021/0060338 A1 | 3/2021 | Thacker |
| 2021/0104310 A1 | 4/2021 | Lin |
| 2021/0275812 A1 | 9/2021 | Subbaroyan et al. |
| 2021/0283400 A1 | 9/2021 | Hamner |
| 2021/0330981 A1 | 10/2021 | Mishra et al. |
| 2023/0191133 A1 | 6/2023 | Baldoni |
| 2023/0248973 A1 | 8/2023 | Subbaroyan et al. |

FOREIGN PATENT DOCUMENTS

| | | |
|---|---|---|
| EP | 2243511 A2 | 10/2010 |
| EP | 2448633 A1 | 5/2012 |
| EP | 2630984 A1 | 8/2013 |
| GB | 2449546 A | 11/2008 |
| JP | 2002200179 A | 7/2002 |
| JP | 2007528774 A | 10/2007 |
| JP | 2008500086 | 1/2008 |
| JP | 2013521979 | 5/2021 |
| KR | 10-2021-0050493 | 6/2013 |
| SU | 1512625 A1 | 10/1989 |
| SU | 1690727 A1 | 11/1991 |
| WO | WO-02065896 A2 | 8/2002 |
| WO | WO-02/085448 | 10/2002 |
| WO | WO-02092165 A1 | 11/2002 |
| WO | WO-03015863 A2 | 2/2003 |
| WO | WO-03066154 A2 | 8/2003 |
| WO | WO-2004007018 A1 | 1/2004 |
| WO | WO-2005115532 A2 | 12/2005 |
| WO | WO-2006007048 | 1/2006 |
| WO | WO-2006057734 A1 | 6/2006 |
| WO | WO-2006063458 | 6/2006 |
| WO | WO-2006084635 A2 | 8/2006 |
| WO | WO-2006119046 A1 | 11/2006 |
| WO | WO-2007035925 A2 | 3/2007 |
| WO | WO-2007082382 A1 | 7/2007 |
| WO | WO-2007103324 A1 | 9/2007 |
| WO | WO-2007117232 A1 | 10/2007 |
| WO | WO-2008039982 A2 | 4/2008 |
| WO | WO-2008045434 A2 | 4/2008 |
| WO | WO-2008106174 A1 | 9/2008 |
| WO | WO-2008121891 A1 | 10/2008 |
| WO | WO-2008140940 | 11/2008 |
| WO | WO-2008142402 A1 | 11/2008 |
| WO | WO-2008153726 A2 | 12/2008 |
| WO | WO-2009018518 A1 | 2/2009 |
| WO | WO-2009061813 A1 | 5/2009 |
| WO | WO-2009097224 A1 | 8/2009 |
| WO | WO-20090129329 A1 | 10/2009 |
| WO | WO-2010111358 A2 | 9/2010 |
| WO | WO-2011014570 A1 | 2/2011 |
| WO | WO-2012154985 | 11/2012 |
| WO | WO-2013036880 | 3/2013 |
| WO | WO-2014146082 | 9/2014 |
| WO | WO-2016154091 A1 | 9/2016 |
| WO | WO-2017044904 | 3/2017 |
| WO | WO-2017142948 | 8/2017 |
| WO | WO-2017146658 | 8/2017 |
| WO | 2018125538 | 7/2018 |
| WO | WO-2020051484 | 3/2020 |

OTHER PUBLICATIONS

CISION PRWeb, "Seattle Pain Relief Now Offering Groundbreaking Treatments for Diabetic and Peripheral Neuropathy," http://www.prweb.com/releases/seattle-pain-center/diabeticneuropathydoctor/prweb12492970.htm Jul. 25, 2022, 3 pages.

McDonnell et al., "Treatment of pain secondary to diabetic peripheral neuropathy (DPN) wit the precisions spinal cord stimulation (SCS) system: a case series," European Journal of Pain 11(S1), 2007, 1 page.

National Institute of Neurological Disorders and Stroke (NINDS), "Paresthesia," https://www.ninds.gov/Disorders/All-Disorders/Paresthesia-Information-Page#disorders-r3>, 2014.

Seattle Pain Relief Video: "What is a Spinal Cord Stimulator," https://www.painmanagement-seattle.com/spinal-cord-stimulator.html 2016, 5 pages.

Tesfaye et al., "Electrical spinal-cord stimulation for painful diabetic peripheral neuropathy," The Lancet. 1996, 4 pages.

YouTube Video: Spinal Cord Stimulator Implants Help Diabetic Peripheral Neuropathy (602) 507-6550, https://www.youtube.com/watch?v=EYao-SfPOwo, Jul. 23, 2012, 3 pages.

U.S. Appl. No. 18/344,579, filed Jun. 29, 2023, Lee.

Karamian et al., "The role of electrical stimulation for rehabilitation and regeneration after spinal cord injury," Journal of Orthopaedics and Traumatology, Jan. 6, 2022, 18 pages.

Mayo Clinic, "Diabetic Neuropathy," https://www.mayoclinic.org/diseases-conditions/diabetic-neuropathy/symptoms-causes/syc-20371580, 1998, 5 pages.

U.S. Appl. No. 14/534,769, filed Nov. 6, 2014, Park.

U.S. Appl. No. 15/606,869, filed May 26, 2017, Lee.

U.S. Appl. No. 17/030,349, filed Sep. 23, 2020, Thacker.

"The Need for Mechanism-Based Medicine in Neuromodulation," Neuromodulation: Technology at the Neural Interface, 2012, 7 pages.

Acticare.com website, http://web.archive.org/web/*/acticare.com, Internet Archive Way Back Machine, 2012, 22 pages.

Al-Kaisy et al., "Sustained Effectiveness of 10kHz High-Frequency Spinal Cord Stimulation for Patients with Chronic, Low Back Pain: 24-month Results of Prospective Multicenter Study," Pain Medicine, 2014, 8 pages.

Alo et al., "New Trends in Neuromodulation for the Management of Neuropathic Pain," Neurosurgery, vol. 50, No. 4, Apr. 2002, 15 pages.

Amendment in Response to Ex Parte Office Action for U.S. Appl. No. 13/446,970, First Named Inventor: Konstantinos Alataris, Mailed: Nov. 28, 2012, 14 pages.

(56) References Cited

OTHER PUBLICATIONS

Amendment in Response to Non-Final Office Action for U.S. Appl. No. 13/245,450, First Named Inventor: Konstantinos Alataris, filed: Feb. 7, 2012, 15 pages.
Amendment in Response to Non-Final Office Action for U.S. Appl. No. 12/765,747, First Named Inventor: Konstantinos Alataris, Mailed: Jan. 24, 2014, 21 pages.
ANSAR—A Medical Technology Developer "Autonomic Nervous System Physiology," http://www.ans-hrv.com/ansphys.htm, Jun. 21, 2012, 2 pages.
Abejon et al., "Is Impedance a Parameter to be Taken into Account in Spinal Cord Stimulation?" Pain Physician, 2007, 8 pages.
Applicant-Initiated Interview Summary for U.S. Appl. No. 13/245,450, First Named Inventor: Konstantinos Alataris, Mailed: Feb. 1, 2012, 2 pages.
Applicant-Initiated Interview Summary for U.S. Appl. No. 13/725,770, First Named Inventor: Konstantinos Alataris, Mailed: Apr. 5, 2013, 3 pages.
Applicant-Initiated Interview Summary for U.S. Appl. No. 12/765,747, First Named Inventor: Konstantinos Alataris, Mailed: Sep. 11, 2013, 3 pages.
Application Data Sheet for U.S. Appl. No. 13/446,970, now U.S. Pat. No. 8,359,102, First Named Inventor: Konstantinos Alataris, Filed: Apr. 13, 2012, 6 pages.
Autonomic Nervous System—Wikipedia, http://en.wikipedia.org/wiki/Autonomic_nervous_system, ; Jun. 20, 2012, 10 pages.
Bahdra et al., Stimulation of High-Frequency Sinusoidal Electrical Block of Mammalian Myelinated Axons, J Comput Neurosco, 22:313-326, 2007.
Bara et al., Poster re: High Frequency Spinal Cord Stimulation for Dominant Back Pain—1 year follow up, 2013, 1 page.
Barolat et al., "Multifactorial Analysis of Epidural Spinal Cord Stimulation," Stereotactic and Functional Neurosurgery, 1991; 56: 77-103.
Barolat et al., "Surgical Management of Pain—Spinal Cord Stimulation: Equipment and Implantation Techniques," Chapter 41, Thieme Medical Publishers, New York, 2002, 11 pages.
Bennett et al., "Spinal Cord Stimulation for Complex regional pain syndrome I [RSD]: a Retrospective Multicenter Experience from 1995 to 1998 of 101 patients." Neuromodulation, vol. 2, No. 3, 1999, 9 pages.
Benyamin et al., "A Case of Spinal Cord Stimulation in Raynaud's Phenomenon: Can Subthreshold Sensory Stimulation Have an Effect? " Pain Physician www.painphysicianjournal.com, 2007, 6 pages.
Bhadra et al., "High Frequency electrical conduction block of the pudendal nerve," Journal of Neural Engineering—Institute of Physics Publishing, ; 2006, 8 pages.
Bhadra MD, Niloy et al., "High-Frequency Electrical Conduction Block of Mammalian Peripheral Motor Nerve," Muscle and Nerve, Dec. 2005, 9 pages.
BionicNAVIGATOR Software Guide, Part MP9055261-001, 2004, 58 pages.
Boger et al., "Bladder Voiding by Combined High Frequency Electrical Pudendal Nerve Block and Sacral Root Stimulation," Neurorology and Urodynamics, 27, 2008, 5 pages.
Boston Scientific "Precision™ Spinal Cord Stimulator System Clinician Manual—Directions for Use," 2015, 74 pages.
Boston Scientific, News Release: "New Data Presented at NANS 2014 Demonstrate Long-Term, Low Back Pain Relief with Boston Scientific Precision Spectra™ Spinal Cord Stimulator System," Dec. 12, 2014, 8 pages.
Bowman and McNeal, Response of Single Alpha Motoneurons to High-Frequency Pulse Trains, Appl. Neurophysiol. 49, p. 121-138, 1986, 10 pages.
Broseta et al., "High-Frequency cervical spinal cord stimulation in spasticity and motor disorders," Advances in Stereotactic and Functional Neurosurgery 7. Springer Verlag 1987, 6 pages.
Burton, Charles, "Dorsal Column Stimulation: Optimization of Application," Surgical Neurology, vol. 4, No. 1, Jul. 1975, 10 pages.
Butt et al., "Histological Findings Using Novel Stimulation Parameters in a Caprine Model," European Journal of Pain Supplements, 2011, 2 pages.
Cahana et al., "Acute Differential Modulation of Synaptic Transmission and Cell Survival During Exposure to Pulsed and Continuous Radiofrequency Energy," Journal of Pain, vol. 4, No. 4, May 2003, 6 pages.
Cameron et al., "Effects of posture on stimulation parameters in spinal cord stimulation," Neuromodulation: Technology at the Neural Interface 1.4, 1998, 8 pages.
Camilleri et al., "Intra-abdominal vagal blocking (VBLOC therapy): clinical results with a new implantable medical device," Surgery 143.6, 2008, 9 pages.
ClinicalTrials.gov, "Safety and Effectiveness Study of the Precision SCS System Adapted for High-Rate Spinal Cord Stimulation (ACCELERATE)," https://clinicaltrials.gov/ct2/show/NCT02093793?term=boston+scientific&recr=Open&cond=%22Pain%22&rank=3, Feb. 2015, 3 pages.
CNS Clinic Jordan, Autonomic Nervous System, ; http://www.neurophysiology.ws.autonomicns.htm, Jun. 21, 2012, 7 pages.
Crapanzano et al., "High Frequency Spinal Cord Stimulation for Complex Regional Pain Syndrome: A Case Report," Pain Physician, 2017, 6 pages.
Crosby et al., "Stimulation Parameters Define the Effectiveness of Burst Spinal Cord Stimulation in a Rat Model of Neuropathic Pain," Neuromodulation Technology at the Neural Interface, International Neuromodulation Society, 2014, 8 pages.
Cuellar et al., "Effect of High Frequency Alternating Current ; on Spinal Afferent Nociceptive Transmission," Neuromodulation: Technology at the Neural Interface, 2012, 10 pages.
Curriculum Vitae and Declaration of Dr. Ganesan Baranidharan on behalf of European Patent No. 2630984,, 4 pages, 2016.
Curriculum Vitae and Declaration of Dr. Jonathan Miller on behalf of European Patent No. 2630984, 20 pages, Oct. 25, 2016.
Curriculum Vitae and Declaration of Dr. Simon James Thomson on behalf of European Patent No. 2630984, Oct. 24, 2016, 2 pages.
Curriculum Vitae and Declaration of Prof. Bengt Linderoth on behalf of European Patent No. 2630984, Oct. 21, 2016, 3 pages.
Curriculum Vitae of Michael A. Moffitt for European Patent No. 2630984, 2015, 2 pages.
De Carolis et al., Poster: "Efficacy of Spinal Cord Stimulation (SCS) in the Treatment of Failed Back Surgery Syndrome (FBSS): a comparative study," 2013, 1 page.
Decision and Minutes: Opposition of European Patent No. 2421600 by Boston Scientific Neuromodulation Corporation, Apr. 3, 2017, 28 pages.
Declaration of Cameron C. McIntyre, Ph.D., May 6, 2015, 88 pages.
Declaration of Cameron C. McIntyre, Ph.D., May 6, 2015, 57 pages.
Declaration of Dr. Jonathan Miller on behalf of European Patent No. 2853285, 26 pages, May 16, 2017.
Declaration of M. Jason D. Rahn for European Patent No. 2243510, dated Feb. 2, 2017, 2 pages.
Declaration of M. Jason D. Rahn, Jan. 7, 2015, 7 pages.
Declaration of Prof. Bengt Linderoth for European Patent No. 2421600, dated Dec. 16, 2016 2 pages.
DeRidder et al., "Are Paresthesias necessary for pain suppression in SCS—Burst Stimulation," Brain, Brain Research Center Antwerp of Innovative and Interdisciplinary Neuromodulation, 2010, 27 pages.
DeRidder et al., "Burst Spinal Cord Stimulation: Toward Paresthesia-Free Pain Suppression," www.neurosurgery-online.com, vol. 66, Nos. 5, May 2010, 5 pages.
Dorland's Illustrated Medical Dictionary, Twenty-sixth Edition, "Paresthesia," 1981, 4 pages.
Doug Atkins of Medtronic Neurological, "Medtronic Neurostimulation Leads, 510(k) Summary," Submission Prepared: Feb. 27, 2004, 6 pages.
Eddicks et al., "Thoracic Spinal Cord Stimulation Improves Functional Status and Relieves Symptoms in Patients with Refractory Angina Pectoris: The First Placebo-Controlled Randomised Study," Heart Journal, 2007, 6 pages.
Ex Parte Office Action for U.S. Appl. No. 13/446,970, First Inventor Named: Konstantinos Alataris, Mailed: Oct. 15, 2012, 9 pages.

(56) References Cited

OTHER PUBLICATIONS

Feeling vs. Function Poster, Mager and Associates Consulting, 2009, 1 page.
First Preliminary Amendment for U.S. Appl. No. 13/446,970, First Named Inventor: Konstantinos Alataris, Mailed: May 18, 2012, 7 pages.
Geddes, "A Short History of the electrical stimulation of excitable tissue—Including Electrotherapeutic Applications," The Physiologist, vol. 27, No. 1, Feb. 1984, 51 pages.
Grill, Warren et al., "Stimulus Waveforms for Selective Neural Stimulation," IEEE Engineering in Medicine and Biology, Jul./Aug. 1995, pp. 375-385.
Gulve et al., Poster: "10kHz High Frequency Spinal Cord Stimulation: Middlesbrough Experience," 2013, 1 page.
Guo et al., "Design and Implement of a Mini-Instrument for Rehabilitation with Transcutaneous Electrical Nerve Stimulation," School of Medical Instrument and Food Engineering, University of Shanghai for Science and Technology, Shanghai China, Mar. 31, 2007, 5 pages.
Hefferman et al., "Efficacy of Transcutaneous Spinal Electroanalgesia in Acute Postoperative Pain Management," Anesthesiology, 2001, 2 pages.
Higuchi et al., "Exposure of the Dorsal Root Ganglion in Rats to Pulsed Radiofrequency Currents Activates Dorsal Horn Lamina I and II Neurons," Neurosurgery, vol. 50, No. 4, Apr. 2002, 7 pages.
Hilberstadt et al., "The Effect of Transcutaneous Spinal Electroanalgesia upon Chronic Pain: A single case study," Physiotherapy, vol. 86 No. 3, Mar. 2000, 2 pages.
Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.
Hopp et al., "Effect of anodal blockade of myelinated fibers on vagal c-fiber afferents," American Journal Physiological Society, Nov. 1980; 239(5), 9 pages.
Hoppenstein, Reuben, "Electrical Stimulation of the Ventral and Dorsal cols. of the Spinal Cord for Relief of Chronic Intractable Pain: Preliminary Report," Surgical Neurology, vol. 4, No. 1, Jul. 1975, 9 pages.
House et al., "Safety and Efficacy of the House/3M Cochlear Implant in Profoundly Deaf Adults," Otolaryngologic Clinics of North America, vol. 19, No. 2, May 1986, 12 pages.
Hunskaar et al., "Epidemiology and Natural History for Urinary Incontinence," International Urogynecology Journal, 2000, 19 pages.
Huxely et al., "Excitation and Conduction in Nerve: Quantitative Analysis," Science, 1964 Sep. 11; 145: 1154-9.
International Neuromodulation Society 10th World Congress, Neuromodulation: Technology that Improves Patient Care, London, England, May 21-26, 2011, 385 pages.
J.P. Morgan North America Equity Research, "Nevro—Let the Launch Begin: Senza Approved, Raising PT to $54," www.jpmorganmarkets.com, May 10, 2015, 8 pages.
J.P. Morgan North America Equity Research, "Nevro—Welcome to the Future of Spinal Cord Stimulation Initiating at OW with $34 Price Target," www.jpmorganmarkets.com, Dec. 1, 2014, 39 pages.
Jacques et al., "Development of a New Implantable Bio-Telestimulator," Surg. Neurol., vol. 13, May 1980, 2 pages.
Jain et al., Abstract—"Accelerate: A Prospective Multicenter Trial Evaluating the Use of High-Rate Spinal Cord Stimulation in the Management of Chronic Intractable Pain," The American Academy of Pain Medicine, 2015, 1 page.
Jang et al., "Analysis of Failed Spinal Cord Stimulation Trails in the Treatment of Intractable Chronic Pain," J. Korean Neurosurg Soc 43, 2008, 5 pages.
Jezernik et al., "Electrical Stimulation for the Treatment of Bladder Dysfunction: Current Status and Future Possibilities," Neurological Research, vol. 24, Jul. 2002, 18 pages.
JMP Securities, "Nevro Corp. (NVRO) Initiating Coverage on Nevro Corp. with a Market Outperform Rating—Investment Highlights," Dec. 1, 2014, 42 pages.

Kapural et al., "Comparison of 10-kHz High Frequency and Traditional Low-Frequency Spinal Cord Stimulation for the Treatment of Chronic Back and Leg Pain: 24-Month Results From a Multicenter, Randomized, Controlled Pivotal Trial," Neurosurgery, vol. 79, No. 5, Nov. 2016, 11 pages.
Kapural et al., "Novel 10-Khz High Frequency Therapy (HF10 Therapy) is Superior to Traditional Low-Frequency Spinal Cord Stimulation for Treatment of Chronic Back and Leg Pain," Anesthesiology The Journal of American Society of Anesthesiologists, Inc., 2015, 11 pages.
Kilgore et al. "Nerve Conduction Block Utilizing High-Frequency Alternating Current" Medical & Biology Engineering and Computing, 2004, vol. 24, pp. 394-406.
Kilgore et al. "Reversible Nerve Conduction Block Using Kilohertz Frequency Alternating Current," Neuromodulation Technology at the Neural Interface, International Neuromodulation Society, 2013, 13 pages.
Kreitler et al., "Chapter 15: Implantable Devices and Drug Delivery Systems—The Handbook for Chronic Pain," NOVA Biomedical Books, New York, 2007, 17 pages.
Krista Oakes of Neuromed, Inc., "Implanted Spinal Cord Stimulator Lead 510(k) Summary of Safety and Effectiveness," Submission Prepared Feb. 21, 1996, 3 pages.
Kuechmann et al., Abstract #853: "Could Automatic Position Adaptive Stimulation Be Useful in Spinal Cord Stimulation?" Medtronic, Inc., Minneapolis, MN, European Journal of Pain 13, 2009, 1 page.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Kumar et al., "The Effects of Spinal Cord Stimulation in Neuropathic Pain Are Sustained: A 24-month Follow-Up of the Prospective Randomized Controlled Multicenter Trial of the Effectiveness of Spinal Cord Stimulation," www.neurosurgery-online.com, vol. 63, No. 4, Oct. 2008, 9 pages.
Lambru et al., "Safety and Efficacy of Cervical 10 kHz Spinal Cord Stimulation in Chronic Refractory Primary Headaches: A Retrospective Case Series," The Journal of Headache and Pain, 2016, 8 pages.
Lempka et al., "Computational Analysis of Kilohertz Frequency Spinal Cord Stimulation for Chronic Pain Management," Anesthesiology, vol. 122, No. 6, Jun. 2015, 15 pages.
Linderoth et al., "Mechanisms of Spinal Cord Stimulation in Neuropathic and Ischemic Pain Syndromes," Neuromodulation, Chapter 25, 2009, 19 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
MacDonald, Alexander J. R, and Coates, Tim W., "The Discovery of Transcutaneous Spinal Electroanalgesia and Its Relief of Chronic Pain," Physiotherapy, vol. 81. No. 11, Nov. 1995, 9 pages.
Manola et al., "Technical Performance of Percutaneous Leads for Spinal Cord Stimulation: A Modeling Study," International Neuromodulation Society, 2005, 12 pages.
Mavoori et al., "An Autonomous implantable computer for neural recording and stimulation in unrestrained primates," Journal of Neuroscience Methods, 2005, 7 pages.
Mayo Clinic, "Erectile Dysfunction—Symptoms & Causes," http://www.mayoclinic.org/diseases-conditions/erectile-dysfunction/symptoms-causes/dxc-20314091, accessed Jun. 5, 2017, 7 pages.
Mayo Clinic, "Tachycardia—Symptoms & Causes," http://www.mayoclinic.org/diseases-conditions/tachycardia/symptoms-causes/dxc-20253873?p=1, accessed Jun. 5, 2017, 4 pages.
Mediati, R.D., "Mechanisms of Spinal Cord Stimulation," Florence, Oct. 2, 2002, 31 pages.
Medtronic—Neurological Division, QuadPlus, Model 3888, Lead Kit for Spinal Cord Stimulation (SCS) Implant Manual, 1996, 33 pages.
Medtronic—Neurological Division, Resume II, Model 3587A, Lead Kit for Spinal Cord Stimulation (SCS) and Peripheral Nerve Stimulation (PNS), Implant Manual, 1996, 32 pages.

(56) References Cited

OTHER PUBLICATIONS

Medtronic—Neurological Division, Resume TL, Model 3986, Lead Kit for Spinal Cord Stimulation (SCS) and Peripheral Nerve Stimulation (PNS), Implant Manual, 1996, 27 pages.
Medtronic—Neurostimulation Systems: Expanding the Array of Pain Control Solutions, 1999, 6 pages.
Medtronic commercial leaflet entitled: Surgical Lead Comparison, 1999, 4 pages.
Medtronic, "Medtronic Pain Therapy—Using Neurostimulation for Chronic Pain, Information for Prescribers" 2007, 29 pages.
Medtronic, Pain Therapy Product Guide, Dec. 2008, 31 pages.
Medtronic, Pisces Quad 3487A, Pisces Quad Compact model 3887, Pisces Quad Plus 3888 Lead Kit, Implant Manual, 2008, 16 pages.
Medtronic: Spinal Cord Stimulation Systems, 2013, 4 pages.
Melzack, Ronald et al., "Pain Mechanisms: A New Theory," Science, vol. 150, No. 3699, Nov. 19, 1965, 9 pages.
Merriam Webster's Collegiate Dictionary, Tenth Edition, definition of "Implantable," 1995, 3 pages.
Meyerson et al., Mechanisms of spinal cord stimulation in neuropathic pain, Neurological Research, vol. 22, Apr. 2000, 5 pages.
Miller, Jonathan, "Neurosurgery Survival Guide—A Comprehensive Guide to Neurosurgical Diagnosis and Treatment," http://d3jonline.tripod.com/neurosurgery/, Nov. 14, 2016, 4 pages.
Miller, Jonathan, "Parameters of Spinal Cord Stimulation and Their Role in Electrical Charge Delivery: A Review," Neuromodulation: Technology at the Neural Interface, 2016.
Morgan Stanley Research North America, "Nevro Corp—There's Something Happening Here," Dec. 15, 2014, 12 pages.
Mosby's Medical Dictionary, 8th Edition, "Paresthesia," 2009, 3 pages.
Mounaïm et al., "New Neurostimulation Strategy and Corresponding Implantable Device to Enhance Bladder Functions," Biomedical Engineering Trends in Electronics, Communications and Software, Chapter 5, 2011, 15 pages.
Mueller et al., "The Med-El Sonatati 100 Cochlear Implant: An evaluation of its safety in adults and children," Acta Oto-Laryngologica, vol. 131, No. 5, 2011, 8 pages.
Muller and Hunsperger, "Helvetica Physiologica Acta—Reversible Blockierung der Erregungsleitung im Nerven durch Mittelfrequenz-Daverstrom," Schwabe & Co. Basel, vol. 25, Fasc. 1, 1967, 4 pages.
Munglani, Rajesh, "The Longer Term Effect of Pulsed Radiofrequency for Neuropathic Pain," Pain 80, 1999, 3 pages.
Nashold et al., "Dorsal col. Stimulation for Control Pain—Preliminary Report on 30 Patients," J. Neurosurg., vol. 36, May 1972, 8 pages.
Nevro—Chronic Pain and Treatments, http://www.nevro.com/English/Patients/Chronic-Pain-and-Treatments/default.aspx; 2016, 3 pages.
Nevro—Clinical Evidence, www.nevro.com/English/Physicians/Clinical-Evidence/default.aspx, 2016, 2 pages.
Nevro—HF10™ Therapy Fact Sheet, http://www.nevro.com/English/Newsroom/Resources/default.aspx, 2015, 4 pages.
Nevro—Physician Overview www.nevro.com/English/Physicians/Physician-Overview/default aspx, 2016, 5 pages.
Nevro—Senza System http://www.nevro.com/English/Physicians/Senza-System/default.aspx, 2016, 3 pages.
Nevro HF10 Therapy—New Hope for Chronic Back Pain and Leg Pain Sufferers, http://s21.q4cdn.com/478267292/files/doc_downloads/HF10-Therapy-New-Hope-for-Chronic-Pain.pdf, 2016, 2 pages.
Nevro Observations and Response to Notice of Oppositions filed by Medtronic Inc., and Boston Scientific for European Patent No. 2207587, mailed Aug. 26, 2016, 16 pages.
Nevro Response to Notice of Oppositions filed by Boston Scientific for European Patent No. 2421600, mailed Jul. 22, 2015, 16 pages.
Nevro Response to Notice of Oppositions filed by Medtronic and Boston Scientific for European Patent No. 2630984, mailed Dec. 7, 2015, 26 pages.
Nevro Response to Opposition of Division's Comments and Summons to Oral Proceedings for European Patent No. 2630984, mailed Oct. 25, 2016, 8 pages.
Nevro Senza Patient Manual, Jan. 16, 2015, 53 pages.
Nevro Senza Physician Implant Manual, Jan. 16, 2015, 31 pages.
Nevro website: HF10 Therapy Advantages, www.nevro.com/English/Patients/HF10-Therapy-Advantages/default.aspx, 2016, 3 pages.
Nevro Written Submissions and Response to Notice of Oppositions filed by Medtronic Inc., and Boston Scientific for European Patent No. 2243510, mailed Aug. 28, 2015, 17 pages.
Nevro, PMA Approval Letter and Referenced Summary of Safety and Effectiveness Data (SSED) May 8, 2015, 60 pages.
Nevro's presentation of HF10 therapy on Nevro's website, http://www.nevro.com/English/Home/default.aspx, 2016, 2 pages.
Nevro's Response to Further Submission by Medtronic, Inc., and Boston Scientific Neuromodulation Corporation for European Patent No. 2243510, mailed Feb. 24, 2017, 9 pages.
Nevros Response to Opponent Submission of Declaration of Jonathan Miller in European Patent No. 2630984, mailed Nov. 18, 2016, 4 pages.
Nevro's Response to Preliminary Opinion for Opposition by Medtronic, Inc., and Boston Scientific Neuromodulation Corporation for European Patent No. 2243510, mailed Feb. 3, 2017, 36 pages.
News Release Details, "Nevro Corp. Announces Pricing of Initial Public Offering, " 2014, 1 page.
NIDCD-NIH 2011, Cochlear Implant Brochure, http://www.nidcd.nih.gov/health/hearing/pages/coch.aspx, Jun. 29, 2012, 2 pages.
Non-Final Office Action for U.S. Appl. No. 12/765,747, First Named Inventor: Konstantinos Alataris, Mailed: Jul. 25, 2013, 7 pages.
Non-Final Office Acton for U.S. Appl. No. 13/245,450, First Named Inventor: Konstantinos Alataris, Mailed Nov. 18, 2011, 11 pages.
North American Neuromodulation Society—14th Annual Meeting, "Neuromodulation: Vision 2010," Dec. 2-5, 2010, 9 pages.
North American Neuromodulation Society—16th Annual Meeting, "From Innovation to Reality Syllabus," Dec. 6-9, 2012, 198 pages.
North American Neuromodulation Society—Celebrating 20 years, 18th Annual Meeting Program Book, Dec. 11-14, 2014, 28 pages.
North American Neuromodulation Society, "Today's Vision, Tomorrow's Reality—17th Annual Meeting," Dec. 5-8, 2013, 12 pages.
North American Neuromodulation, "15th Annual Meeting, Our Crystal Anniversary," Dec. 8-11, 2011, 8 pages.
North et al., "Failed Back Surgery Syndrome: 5-year Follow-Up after Spinal; Cord Stimulator Implantation," Neurosurgery, Official Journal of Congress of Neurological Surgeons, vol. 28, No. 5, May 1991, 9 pages.
North et al., "Spinal Cord Stimulation for Axial Low Back Pain," Spine, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
North et al., "Spinal Cord Stimulation With Interleaved Pulses: A Randomized, Controlled Trial," vol. 10, No. 4, 2007, 9 pages.
Notice of Allowance for U.S. Appl. No. 13/245,450, First Named Inventor: Konstantinos Alataris, Mailed: Mar. 14, 2012, 8 pages.
Notice of Opposition to a European Patent for European Patent No. 2586488, Proprietor of the Patent: Nevro Corporation, Opponent: Medtronic, Inc., Mar. 15, 2017, 7 pages.
Notice of Opposition to a European Patent for European Patent No. 2853285, Proprietor of the Patent: Nevro Corporation, Opponent: Medtronic, Inc., Apr. 19, 2017, 40 pages.
Notice of Opposition to a European Patent for European Patent No. 2853285, Proprietor of the Patent: Nevro Corporation, Opponent: Boston Scientific Neuromodulation Corporation, May 16, 2017, 18 pages.
Notice of Opposition to a European Patent, Argument and Facts, and Annex for European Patent No. 2421600, Proprietor of the Patent: Nevro Corporation; Opponent: Boston Scientific Neuromodulation Corporation, Dec. 4, 2014, 22 pages.
Notice of Opposition to a European Patent, Argument and Facts, for European Patent No. 2243510, Proprietor of the Patent: Nevro Corporation, Opponent: Medtronic, Jan. 8, 2015, 22 pages.
Notice of Opposition to a European Patent, Argument and Facts, and Annex for European Patent No. 2243510, Proprietor of the Patent: Nevro Corporation; Opponent: Boston Scientific Neuromodulation Corporation, Jan. 8, 2015, 28 pages.

(56) References Cited

OTHER PUBLICATIONS

Notice of Opposition to a European Patent, Argument and Facts for European Patent No. 2630984, Proprietor of the Patent: Nevro Corporation; Opponent: Medtronic, Mar. 17, 2015, 17 pages.

Notice of Opposition to a European Patent, Argument and Facts, and Annex for European Patent No. 2630984, Proprietor of the Patent: Nevro Corporation; Opponent: Boston Scientific Neuromodulation Corporation, Mar. 17, 2015, 21 pages.

Notice of Opposition to a European Patent, Argument and Facts, for European Patent No. 2207587, Proprietor of the Patent: Nevro Corporation; Opponent: Medtronic, Inc., Jan. 12, 2016, 22 pages.

Notice of Opposition to a European Patent, Argument and Facts, for European Patent No. 2207587, Proprietor of the Patent: Nevro Corporation; Opponent: Boston Scientific Neuromodulation Corporation, Jan. 8, 2016, 17 pages.

Oakley et al., "A New Spinal Cord Stimulation System Effectively Relieves Chronic, Intractable Pain: A Multicenter Prospective Clinical Study," Neuromodulation: Technology at the Neural Interface, vol. 10, No. 3, 2007, 17 pages.

Oakley et al., "Spinal Cord Stimulation in Axial Low Back Pain: Solving the Dilemma," Pain Medicine, vol. 7, No. S1, 2006, 6 pages.

Oakley, John C., "Spinal Cord Stimulation Mechanisms of Action," ; Spine vol. 27, No. 22, copyright 2002, 10 pages.

OHSIPP Summer Newsletter, The Official Newsletter for the Ohio Society of Interventional Pain Physicians, vol. 1 Ed. 2, Summer 2010, 8 pages.

Opponent Boston Scientific: Response to Attend Oral Proceedings for European Patent No. 2630984, mailed Oct. 25, 2016, 21 pages.

Opponent Response to Patent Proprietor Comments to Declaration of Dr. Jonathan Miller for European Patent No. 2630984, mailed Nov. 22, 2016, 3 pages.

Opponents Boston Scientific Neuromodulation Corp.: Additional Observations in view of Oral Proceedings for European Patent No. 2243510, mailed Feb. 3, 2017, 8 pages.

Opponents Boston Scientific: Response to Summons to Attend Oral Proceedings for European Patent No. 2421600, mailed Jan. 2, 2017, 15 pages.

Opponents Medtronic, Inc.: Additional Observations in view of Oral Proceedings for European Patent No. 2243510, mailed Feb. 3, 2017, 10 pages.

Opponents Medtronic, Inc.: Response to Attend Oral Proceedings for European Patent No. 2630984, mailed Oct. 25, 2016, 26 pages.

Opponents Medtronic: Response to Nevro Requests and Submission for European Patent No. 22453510, mailed Mar. 29, 2017, 3 pages.

Opponents Response to Patentee's (Nevro) Written Submissions for European Patent No. 2243510, mailed Feb. 22, 2016, 21 pages.

Paicius et al., "Peripheral Nerve Field Stimulation for the Treatment of Chronic Low Back Pain: Preliminary Results of Long-Term Follow-up: A Case Series," Neuromodulation: Technology at the Neural Interface, vol. 10, No. 3, 2007, 12 pages.

Palmer et al., "Transcutaneous electrical nerve stimulation and transcutaneous spinal electroanalgesia: A preliminary efficacy and mechanisms-based investigation," Physiotherapy, 95, 2009, 7 pages.

Patent Owner's Preliminary Response for Inter Partes Review for U.S. Pat. No. 8,359,102, Case No. IPR2015-01203, Petitioner: Boston Scientific Neuromodulation Corporation, Patent Owner: Nevro Corporation, mailed Sep. 1, 2015, 70 pages.

Patent Owner's Preliminary Response for Inter Partes Review for U.S. Pat. No. 8,359,102, Case No. IPR2015-01204, Petitioner: Boston Scientific Neuromodulation Corporation, Patent Owner: Nevro Corporation, mailed Sep. 1, 2015, 63 pages.

Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.

Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, May 14, 2015, 45 pages.

Petition for Inter Partes Review of Claims 1, 2, 11-15, 17-23, 25 and 26 for U.S. Pat. No. 8,359,102, Petitioner: Boston Scientific Neuromodulation Corporation, Patent Owner: Nevro Corporation, May 14, 2015, 67 pages.

Prausnitz et al., "The Effects of Electric Current Applied to Skin: A Review for Transdermal Drug Delivery," Advanced Drug Delivery Reviews 18, ; 1996, 31 pages.

Precision—Physician System Handbook, Advanced Bionic Corporation, Part 9055253-0001, 2005, 92 pages.

Precision—Physician Trail Kit Insert, Advanced Bionic Corporation, Part 9055258-0001, 2005, 2 pages.

Precision Spinal Cord Stimulation—Charging System Insert, Advanced Bionic Corporation, Part 9055074-0001, 2004, 2 pages.

Precision Spinal Cord Stimulation—Charging System, Advanced Bionic Corporation, Part 9055259-0001, 2004, 2 pages.

Precision Spinal Cord Stimulation—Patient System Handbook, Advanced Bionic Corporation, Part 9055072-0001, 2004, 93 pages.

Precision Spinal Cord Stimulation—Patient Trial Journal, Advanced Bionic Corporation, Part 9055260-0001, 2004, 10 pages.

Precision Spinal Cord Stimulation—Physician Implant Manual, Advanced Bionic Corporation, Part 9055100, 2004, 62 pages.

Precision Spinal Cord Stimulation—Physician Implant Manual, Advanced Bionic Corporation, Part 9055255-0001, 2005, 70 pages.

Precision Spinal Cord Stimulation—Physician Lead Manual, Advanced Bionic Corporation, Part 9055095, 2004, 62 pages.

Precision Spinal Cord Stimulation—Physician Lead Manual, Advanced Bionic Corporation, Part 9055256-0001, 2005, 56 pages.

Precision Spinal Cord Stimulation—Physician Lead Manual, Advanced Bionic Corporation, Part No. 9055183-001, May 2004, 31 pages.

Precision Spinal Cord Stimulation—Physician Trail Handbook, Advanced Bionic Corporation, Part 9055254-0001, 2005, 66 pages.

Precision Spinal Cord Stimulation—Physician Trail Kit Model SC-7005, Part 9055066-001, Advanced Bionic Corporation, 2004, 2 pages.

Precision Spinal Cord Stimulation—Remote Control Model SC-5200, Part 9055107-001, 2004, Advanced Bionic Corporation, 2 pages.

Precision Spinal Cord Stimulation—Remote Control Model SC-5210, Advanced Bionic Corporation, Part 9055257-001, 2005, 2 pages.

Precision Spinal Cord Stimulation System, Patient Trial Handbook, Part 9055078, 2004, 74 pages.

Pudenz et al., "Development of an Implantable Telestimulator," Proc. 4th Ann. Nat'l Conf. Neuroelectric Soc., Mar. 10-12, 1971, 111-12 (Wulfsohn, Norman L. and Anthony Sances, Jr. (eds.) 1971, 4 pages.

Pudenz et al., "Neural Stimulation: Clinical and Laboratory Experiences", Surg. Neurol, 39:235-242 (1993).

Rapcan et al., Clinical Study, "High-Frequency—Spinal Cord Stimulation," Indexed and Abstracted in Science Citation Index Expanded and in Journal Citation Reports, 2015, 3 pages.

Reddy et al., "Comparison of Conventional and Kilohertz Frequency Epidural Stimulation in Patients Undergoing Trailing for Spinal Cord Stimulation: Clinical Considerations," World Neurosurgery, www.sciencedirect.com, 6 pages, 2015.

Remedi Pain Relief—ENM (Electronic Nerve Modulation), https://web.archive.org/web/20050906181041/http://www.remediuk.com/trials.htm, 2005, 5 pages.

Resume of Jason D. Rahn, Jan. 7, 2015, 2 pages.

Robb et al., "Transcutaneous Electrical Nerve Stimulation vs. Transcutaneous Spinal Electroanalgesia for Chronic Pain Associated with Breast Cancer Treatments," Journal of Pain and Symptom Management, vol. 33, No. 4, Apr. 2007, 10 pages.

Royle, John., "Transcutaneous Spinal Electroanalgesia and Chronic Pain," Physiotherapy, vol. 86, No. 5, May 2000, 1 page.

Satish et al., "State of the Art: Pathophysiology—Pathophysiology of Adult Fecal Incontinence," Gastroenterology, 2004, 9 pages.

Schulman et al., "Battery Powered BION FES Network," Proceedings of the 26th Annual Conference of the IEEE EMBS, San Francisco, CA., Sep. 1-5, 2004, 4 pages.

(56) References Cited

OTHER PUBLICATIONS

Science Daily, "Chronic Pain Costs U.S. up to $635 billion, study shows," www.sciencedaily.com/releases/2012/09/120911091100.htm, Sep. 11, 2012, 2 pages.
Senza Spinal Cord Stimulation (SCS) System—P130022, http://www.fda.gov/MedicalDevices/ProductsandMedicalProcedures/DeviceApprovalsandClearances/Recently-ApprovedDevices/ucm449963.htm Oct. 14, 2016, 2 pages.
Shealy et al., "Dorsal col. Electrohypalgesia," Jul. 1969, 8 pages.
Shealy MD, C. Norman et al., "Electrical Inhibition of Pain by Stimulation of the Dorsal cols. Preliminary Clinical Report," Anesthesia and Analgesia Current Researches, vol. 446, No. 4, Jul.- Aug. 1967, 3 pages.
Shelden et al., "Depolarization in the Treatment of Trigeminal Neuralgia," Evaluation of Compression and Electrical Methods, Clinical Concept of Neurophysiological Mechanism, 1966, 8 pages.
Shelden et al., "Development and Clinical Capabilities of a New Implantable Biostimulator," The American J. of Surgery, vol. 124, Aug. 1972, 6 pages.
Shelden et al., Electrical Control of Facial Pain, Am. J. of Surgery, vol. 114, Aug. 1967, 6 pages.
Shelden et al., "Electrical stimulation of the nervous system," Surg. Neurol. vol. 4, No. 1, Jul. 1975, 6 pages.
Simpson et al., "A Randomized, Double-Blind, Crossover Study of the Use of Transcutaneous Spinal Electroanalgesia in Patients with Pain from Chronic Critical Limb Ischemia," Journal of Pain and Symptom Management, vol. 28, No. 5, Nov. 2004, 6 pages.
Simpson, BA, "Spinal Cord Stimulation in 60 cases of Intractable Pain." Journal of Neurology, Neurosurgery and Psychiatry, 1991; 54 pp. 196-199.
Simpson, BA, "Spinal Cord Stimulation." British Journal of Neurosurgery, 1997, Feb. 11 (1), 5-11, 7 pages.
Sluijter et al., "The Effects of Pulsed Radiofrequency Fields Applied to the Dorsal Root Ganglion—A Preliminary Report," The Pain Clinic, vol. 11, No. 2, 1998, 12 pages.
Smet et al.,., "Successful Treatment of Low Back Pain with a Novel Neuromodulation Device," AZ Nikolaas, 12 pages.
Smet et al., Poster: "High-Frequency Spinal Cord Stimulation at 10 kHz after Failed Traditional Spinal Cord Stimulation," NANS, 2013, 1 page.
Solomonow et al., "Control of Muscle Contractile Force through Indirect High-Frequency Stimulation," AM Journal of Physical Medicine, 1983, vol. 62, No. 3, pp. 71-82.
St. Jude Medical, "Eon Mini™ Rechargeable IPG," Apr. 29, 2013, 3 pages.
St. Jude Medical, "Individualized Therapy through Diverse Lead Options," 2008, 6 pages.
Stimwave, News Release: "Stimwave Receives FDA Approval for High Frequency IDE," http://stimwave.com/newsroom/latest-news, Jun. 9, 2015, 2 pages.
Struijk et al., "Recruitment of Dorsal Column Fibers in Spinal Cord Stimulation: Influence of Collateral Branching," IEEE Transactions on Biomedical Engineering, vol. 39, No. 9, Sep. 1992, 10 pages.
Sweet et al., "Paresthesia-Free High Density Spinal Cord Stimulation for Postlaminectomy Syndrome in a Prescreened Population: A Prospective Case Series," Neuromodulation: Technology at the Neural Interface, 2015, 7 pages.
Swigris et al., "Implantable Spinal Cord Stimulator to Treat the Ischemic Manifestations of Thromboangiitis Obliterans (Buerger's disease)," Journal of Vascular Surgery, vol. 29, No. 5, 1998, 8 pages.
Tan et al., "Intensity Modulation: A Novel Approach to Percept Control in Spinal Cord Stimulation," Neuromodulation Technology at the Neural Interface, International Neuromodulation Society 2015, 6 pages.
Tanner, J.A., "Reversible blocking of nerve conduction by alternating-current; excitation," Nature, 1962, Aug. 18; 195: 712-3.
Taylor et al., "The Cross Effectiveness of Spinal Cord Stimulation in the Treatment of Pain: A Systematic Review of the Literature," Journal of Pain and Symptom Management, vol. 27, No. 4., Apr. 2001, 9 pages.
Tesfaye et al., "Electrical Spinal Cord Stimulation for Painful Diabetic Peripheral Neuropathy," The Lancet, vol. 348, Dec. 21-28, 1996, 4 pages.
Thompson et al., "A double blind randomised controlled clinical trial on the effect of transcutaneous spinal electroanalgesia (TSE) on low back pain," European Journal of Pain, vol. 12, Issue 3, Apr. 2008, 6 pages.
Tiede et al., "Novel Spinal Cord Stimulation Parameters in Patients with Predominate Back Pain," Neuromodulation: Technology at the Neural Interface, 2013, 6 pages.
Tollison et al., "Practical Pain Management; Neurostimulation Techniques," Chapter 12, Lippincott Williams and Wilkins, Third Edition, 2002, 13 pages.
Towell et al., "High Frequency non-invasive stimulation over the spine: Effects on mood and mechanical pain tolerance in normal subjects," Behavioral Neurology, vol. 10, 1997, 6 pages.
Urban et al., "Percutaneous epidural stimulation of the spinal cord for relief of pain—Long Term Results," Journal of Neurosurgery, vol. 48, ; Mar. 1978, 7 pages.
Van Butyen et al., "High Frequency Spinal Cord Stimulation for the Treatment of Chronic Back Pain Patients: Results of a Prospective Multicenter European Clinical Study," Neuromodulation Technology at the ; Neural Interface, International Neuromodulation Society, 2012, 8 pages.
Van Buyten et al., "Pain Relief for Axial Back Pain Patients," INS Meeting Poster, 1 page.
Van Den Honert et al. "Generation of Unidirectionally Propagated Action Potentials Nerve by Brief Stimuli" Science, vol. 26, pp. 1311-1312.
Van Den Honert, Mortimer JT, "A Technique for Collision Block of Peripheral Nerve: Frequency Dependence," MP-11 IEEE Trans. Biomed, Eng. 28: 379-382, 1981.
Van Havenbergh et al., "Spinal Cord Stimulation for the Treatment of Chronic Back Pain Patients: 500-Hz vs. 1000-Hz Burst Stimulation," Neuromodulation: Technology at the Neural Interface, International Neuromodulation Society, 2014, 4 pages.
Verrills et al., "Peripheral Nerve Field Stimulation for Chronic Pain: 100 Cases and Review of the Literature," Pain Medicine, 2011, 11 pages.
Verrills et al., "Salvaging Failed Neuromodulation Implants with Nevro High Frequency Spinal Cord System," NANS Poster, 2013, 1 page.
Von Korff et al., "Assessing Global Pain Severity by Self-Report in Clinical and Health Services Research," Spine, vol. 25, No. 24, 2000, 12 pages.
Wallace et al., Poster: "Accelerate: A Prospective Multicenter Trial Evaluating the Use of High-Rate Spinal Cord Stimulation in the Management of Chronic Intractable Pain," Boston Scientific Corporation, 2015, 1 page.
Wallin et al., "Spinal Cord Stimulation inhibits long-term potentiation of spinal wide dynamic range neurons," Elsevier Science B.V., Brain Research, 5 pages, 2003.
Ward et al., "Electrical Stimulation Using Kilohertz-Frequency Alternating Current," Journal of the American Physical Therapy Association, vol. 89, No. 2, Feb. 2009, 12 pages.
Ward et al., "Variation in Motor Threshold with Frequency Using kHz Frequency Alternating Current," Muscle and Nerve, Oct. 2001, 9 pages.
Webster's Third New International Dictionary of the English Language Unabridged, "Paresthesia," 1993, 3 pages.
Weinberg et al., "Increasing the oscillation frequency of strong magnetic fields above 101 kHz significantly raises peripheral nerve excitation thresholds," Medical Physics Letter, May 2012, 6 pages.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.
Woo MY, Campbell B. "Asynchronous Firing and Block of Peripheral Nerve Conduction by 20KC Alternating Current," Los Angeles Neuro Society, 1964, Jun.; 87-94, 5 pages.
Yearwood et al., "A Prospective Comparison of Spinal Cord Stimulation (SCS) Using Dorsal col. Stimulation (DCS), Intraspinal Nerve Root Stimulation (INRS), and Varying Pulse Width in the

(56) References Cited

OTHER PUBLICATIONS

Treatment of Chronic Low Back Pain," Congress of Neurological Surgeons 56th Annual Meeting, Oct. 7-12, 2006, 2 pages.
Yearwood et al., Case Reports: "A Prospective Comparison of Spinal Cord Stimulation (SCS) Using Dorsal col. Stimulation (DCS), Intraspinal Nerve Root Stimulation (INRS), and Varying Pulse Width in the Treatment of Chronic Low Back Pain," Presented at the Congress of Neurological Surgeons 56th Annual Meeting, Oct. 7-12, 2006, 7 pages.
Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
Zhang et al., Changes Across Time in Spike Rate and Spike Amplitude of Auditory Nerve Fibers Stimulated by Electric Pulse Trains, Journal of the Association for Research of Otolaryngology, 2007, 17 pages.
Declaration of Rafael Carbunaru in Support of Boston Scientific's Invalidity Contentions, *Nevro Corp.* (Plaintiff) vs. *Boston Scientific Corporation and Boston Scientific Neuromodulation Corporation,* Case No. 3:16-cv-06830-VC, executed Mar. 17, 2017, 5 pages.
Exhibit A of Declaration of Rafael Carbunaru: "Physician Implant Manual—Precision," in Support in Support of Defendants Boston Scientific Corporation's and Boston Scientific Neuromodulation Corporation's Invalidity Contentions, Advanced Bionics, 2004, 62 pages.
Exhibit B of Declaration of Rafael Carbunaru: "Physician Lead Manual—Precision," in Support in Support of Defendants Boston Scientific Corporation's and Boston Scientific Neuromodulation Corporation's Invalidity Contentions, Advanced Bionics, 2004, 62 pages.
Exhibit C of Declaration of Rafael Carbunaru: "Patient System Handbook—Precision," in Support in Support of Defendants Boston Scientific Corporation's and Boston Scientific Neuromodulation Corporation's Invalidity Contentions, Advanced Bionics, 2004, 93 pages.
Defendant's Boston Scientific Corporation's and Boston Scientific Neuromodulation Corporation's Preliminary Invalidity Contentions, Case No. 3:16-cv-06830-VC, filed Mar. 17, 2017, 159 pages.
Exhibit A1: Invalidity Chart v. MacDonald (U.S. Pat. No. 5,776,170), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 294 pages.
Exhibit A2: Invalidity Chart v. Spinner (U.S. Patent Application Publication No. 2007/0213771), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 235 pages.
Exhibit A3: Invalidity Chart v. Knudson (U.S. Patent Application Publication No. 2007/0073354), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 301 pages.
Exhibit A4: Invalidity Chart v. Butukhanov (Soviet Union Publication No. 1512625), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 233 pages.
Exhibit A5: Invalidity Chart v. Sluijter (U.S. Pat. No. 6,246,912), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16- cv-06830-VC (N.D. Cal.), Mar. 17, 2017, 226 pages.
Exhibit A6: Invalidity Chart v. Kilgore (U.S. Pat. No. 7,389,145), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16- cv-06830-VC (N.D. Cal.), Mar. 17, 2017, 219 pages.
Exhibit A7: Invalidity Chart v. Royle (U.S. Patent Application Publication No. 2006/0009820), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 188 pages.
Exhibit A8: Invalidity Chart v. King (U.S. Patent Application Publication No. 2007/0149148), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 222 pages.
Exhibit A9: Invalidity Chart v. DeRidder (U.S. Patent Application Publication No. 2011/0184488), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 266 pages.
Exhibit A10: Invalidity Chart v. Fang (U.S. Patent Application Publication No. 2009/0204173), Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 191 pages.
Exhibit B1: Invalidity Chart v. Boston Scientific's Precision Spinal Cord Stimulation System, Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 337 pages.
Exhibit C1: 35 U.S.C. § 103(a) Invalidity Chart, Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Mar. 17, 2017, 400 pages.
Nevro's Motion for Summary Adjudication—Notice of Motion, Motion and Memorandum of Points and Authorities in the Support of Nevro's Motion for Summary Adjudication (Document 461), *Nevro Corp.* v. *Boston Scientific Corporation and Boston Scientific Neuromodulation Corporation,* Case No. 3:16-cv-06830-VC-MEJ, filed Jul. 30, 2018, 50 pages.
Declaration of Konstantinos Alataris in Support of Nevro's Motion of Summary Adjudication (Document 342-1), *Nevro Corp.* v. *Boston Scientific Corporation and Boston Scientific Neuromodulation Corporation,* Case No. 3:16-cv-06830-VC-MEJ, Apr. 11, 2018, 3 pages.
Exhibit 1 for Declaration of Konstantinos Alataris in Support of Nevro's Motion of Summary Adjudication (Document 342-2), Notes from NBI Mayo Physician Meeting Dec. 4, 2016, Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), Apr. 12, 2018, 3 pages.
Exhibit 2 for Declaration of Konstantinos Alataris in Support of Nevro's Motion of Summary Adjudication (Document 342-3), Notes from NBI Development—Mayo Clinic Dec. 4, 2016, Boston Scientific Corporation's and Boston Scientific Neuromodulation Corporation's Invalidity Contentions, *Nevro Corp.* v. *Boston Scientific Corporation and Boston Scientific Neuromodulation Corporation,* Case No. 3:16-cv-06830-VC (N.D. Cal.), filed Apr. 12, 2018, 11 pages.
Exhibit 3 for Declaration of Konstantinos Alataris in Support of Nevro's Motion of Summary Adjudication (Document 342-4), Sep. 2007 Email between O. Filho and Konstantinos Alataris, Boston Scientific Corporation's and Boston Scientific Neuromodulation Corporation's Invalidity Contentions, *Nevro Corp.* v. *Boston Sci-*

(56) References Cited

OTHER PUBLICATIONS

*entific Corporation and Boston Scientific Neuromodulation Corporation,* Case No. 3:16-cv-06830-VC (N.D. Cal.), filed Apr. 12, 2018, 4 pages.
Exhibit 4 for Declaration of Konstantinos Alataris in Support of Nevro's Motion of Summary Adjudication (Document 342-5) NBI Development Inc., Jun. 12, 2007 Board Meeting, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 31 pages.
Declaration of Ben Pless in Support of Nevro's Motion for Summary Adjudication (Updated Redacted Version of EFC No. 347-24), *Nevro Corp. v. Boston Scientific Corporation and Boston Scientific Neuromodulation Corporation,* Case No. 3:16-cv-06830-VC-MEJ, Apr. 11, 2018, 64 pages.
Exhibit A for Declaration of Ben Pless in Support of Nevro's Motion for Summary Adjudication (Document 342-7) Curriculum Vitae of Benjamin Pless, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Jul. 30, 2018, 15 pages.
Declaration of Eric C. Pai in Support of Nevro's Motion for Summary Adjudication (Document 343), *Nevro Corp. v. Boston Scientific Corporation and Boston Scientific Neuromodulation Corporation,* Case No. 3:16-cv-06830-VC-MEJ, Apr. 12, 2018, 11 pages.
Exhibit 1 for Declaration of Eric C. Pai in Support of Nevro's Motion for Summary Adjudication (Document 343-1) Chart—Asserted Claims with Disputed Terms Underlined, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 5 pages.
Exhibit 2 for Declaration of Eric C. Pai in Support of Nevro's Motion for Summary Adjudication (Document 343-2) Certified Copy of U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 34 pages.
Exhibit 3 for Declaration of Eric C. Pai in Support of Nevro's Motion for Summary Adjudication (Document 343-3) Certified Copy of U.S. Pat. No. 8,712,533, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 37 pages.
Exhibit 4 for Declaration of Eric C. Pai in Support of Nevro's Motion for Summary Adjudication (Document 343-4) Certified Copy of U.S. Pat. No. 8,768,472, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 37 pages.
Exhibit 5 for Declaration of Eric C. Pai in Support of Nevro's Motion for Summary Adjudication (Document 343-5) Certified Copy of U.S. Pat. No. 8,792,988, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 35 pages.
Exhibit 6 for Declaration of Eric C. Pai in Support of Nevro's Motion for Summary Adjudication (Document 343-6) Certified Copy of U.S. Pat. No. 9,327,125, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 40 pages.
Exhibit 7 for Declaration of Eric C. Pai in Support of Nevro's Motion for Summary Adjudication (Document 343-7) Certified Copy of U.S. Pat. No. 9,333,357, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-CV-06830-VC (N.D. Cal.), filed Apr. 12, 2018, 39 pages.
Exhibit 8 for Declaration of Eric C. Pai in Support of Nevro's Motion for Summary Adjudication (Document 343-8) Certified Copy of U.S. Pat. No. 9,480,842, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 38 pages.
Exhibit 9 for Declaration of Eric C. Pai in Support of Nevro's Motion for Summary Adjudication (Document 343-9) Article by Leonardo Kapural et al., Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 11 pages.
Exhibit 10 for Declaration of Eric C. Pai in Support of Nevro's Motion for Summary Adjudication (Document 343-10) Article by Antonio Foletti et al., Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 15 pages.
Exhibit 11 for Declaration of Eric C. Pai in Support of Nevro's Motion for Summary Adjudication (Document 343-11) Article by Leonardo Kapural et al., Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 12 pages.
Exhibit 12 for Declaration of Eric C. Pai in Support of Nevro's Motion for Summary Adjudication (Document 343-12) Poster by Mark Wallace et al., Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 2 pages.
Exhibit 13 for Declaration of Eric C. Pai in Support of Nevro's Motion for Summary Adjudication (Document 343-13) Summary of Safety and Effectiveness Data (SSED), Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 6 pages.
Exhibit 14 for Declaration of Eric C. Pai in Support of Nevro's Motion for Summary Adjudication (Document 343-14) Nevro - Notes from Las Vegas and Our Survey of 50 US pain docs, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 19 pages.
Exhibit 15 for Declaration of Eric C. Pai in Support of Nevro's Motion for Summary Adjudication (Document 343-15) Apr. 2012 Email between K. Bradley and J. Cassidy, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 5 pages.
Exhibit 16 for Declaration of Eric C. Pai in Support of Nevro's Motion for Summary Adjudication (Document 343-16) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation,* Case No. 3:16-cv-06830-VC (N.D. Cal.), filed Apr. 12, 2018, 1 page.

(56) References Cited

OTHER PUBLICATIONS

Exhibit 17 for Declaration of Eric C. Pai in Support of Nevro's Motion for Summary Adjudication (Document 343-17) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 18 for Declaration of Eric C. Pai in Support of Nevro's Motion for Summary Adjudication (Document 343-18) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 19 for Declaration of Eric C. Pai in Support of Nevro's Motion for Summary Adjudication (Document 343-19) Entire Document Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 20 for Declaration of Eric C. Pai in Support of Nevro's Motion for Summary Adjudication (Document 343-20) Redacted Version of Document Sought to be Sealed—Excerpts from May 18, 2018 Deposition of R. Carbunaru, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.

Exhibit 21 for Declaration of Eric C. Pai in Support of Nevro's Motion for Summary Adjudication (Document 343-21) Certified Copy of U.S. Pat. No. 8,792,988, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 9 pages.

Exhibit 22 for Declaration of Eric C. Pai in Support of Nevro's Motion for Summary Adjudication (Document 462) Updated Redacted Version of ECF No. 347-10 - Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 9 pages.

Exhibit 23 for Declaration of Eric C. Pai in Support of Nevro's Motion for Summary Adjudication (Document 463) Updated Redacted Version of ECF No. 347-12, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Jul. 30, 2018, 23 pages.

Exhibit 24 for Declaration of Eric C. Pai in Support of Nevro's Motion for Summary Adjudication (Document 343-24) Redacted Version of Document Sought to Be Sealed—BSC's Supplemental Responses and Objections to Nevro First Set of Interrogatory Request, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 11 pages.

Exhibit 25 for Declaration of Eric C. Pai in Support of Nevro's Motion for Summary Adjudication (Document 464) Updated Redacted Version of ECF No. 347-16—BSC's Second Supplemental Responses and Objections to Nevro First Set of Interrogatory Request, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.

Exhibit 26 for Declaration of Eric C. Pai in Support of Nevro's Motion for Summary Adjudication (Document 343-26) Decision Denying Institution of Inter Partes Review 37 CFR § 42.108-IPR2015-01203 U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 21 pages.

Exhibit 27 for Declaration of Eric C. Pai in Support of Nevro's Motion for Summary Adjudication (Document 343-27) Decision Denying Institution of Inter Partes Review 37 CFR § 42.108-IPR2015-01204 U.S. Pat. No. 8,359,102, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 15 pages.

Exhibit 28 for Declaration of Eric C. Pai in Support of Nevro's Motion for Summary Adjudication (Document 343-28) Certified Copy of U.S. Pat. No. 9,333,357, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.

Exhibit 29 for Declaration of Eric C. Pai in Support of Nevro's Motion for Summary Adjudication (Document 343-29) Rebuttal Expert Report and Declaration of Gene Fridman, Ph.D., regarding Claim Construction—Feb. 14, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.

Exhibit 30 for Declaration of Eric C. Pai in Support of Nevro's Motion for Summary Adjudication (Document 343-30) Deposition of Dr. Gene Fridman on Mar. 7, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 49 pages.

Exhibit 31 for Declaration of Eric C. Pai in Support of Nevro's Motion for Summary Adjudication (Document 343-31) Rebuttal Expert Report and Declaration of Gene Fridman, Ph.D., regarding Claim Construction—Jan. 18, 2018, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.

Exhibit 32 for Declaration of Eric C. Pai in Support of Nevro's Motion for Summary Adjudication (Document 343-32) Deposition of Kaoru Lee Adair—May 10, 2017, Entire Document Sought to be Sealed, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.

Exhibit 33 for Declaration of Eric C. Pai in Support of Nevro's Motion for Summary Adjudication (Document 343-33) Expert Report and Declaration of Adam Lipson, M.D., pursuant to Federal Rule of Civil Procedure 26(A)(2)(B) dated Jan. 18, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.

Exhibit 34 for Declaration of Eric C. Pai in Support of Nevro's Motion for Summary Adjudication (Document 343-34) Stedman's Medical Dictionary 27th Edition, definition "paresthesia", Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.

Exhibit 35 for Declaration of Eric C. Pai in Support of Nevro's Motion for Summary Adjudication (Document 343-35) Dorland's

(56) References Cited

OTHER PUBLICATIONS

Illustrated Medical Dictionary, definition "paresthesia", Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 4 pages.

Exhibit 36 for Declaration of Eric C. Pai in Support of Nevro's Motion for Summary Adjudication (Document 343-36) Mosby's Medical Dictionary, definition "paresthesia", Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 5 pages.

Exhibit 37 for Declaration of Eric C. Pai in Support of Nevro's Motion for Summary Adjudication (Document 343-37) National Institute of Neurological Disorders and Stroke—Paresthesia Information Page, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 4 pages.

Exhibit 38 for Declaration of Eric C. Pai in Support of Nevro's Motion for Summary Adjudication (Document 343-38) Videotaped Deposition of Richard T. Mihran, Ph.D. on Mar. 12, 2018, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 10 pages.

Exhibit 39 for Declaration of Eric C. Pai in Support of Nevro's Motion for Summary Adjudication (Document 343-39) Boston Scientific—Precision Spinal Cord Stimulator System with MultiWave Technology Clinician Manual,, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 68 pages.

Exhibit 40 for Declaration of Eric C. Pai in Support of Nevro's Motion for Summary Adjudication (Document 343-40) BSC's Amended and Supplemental Responses and Objections to Nevro's Second Set of Interrogatories (Nos. 9, 10) dated Aug. 24, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 18 pages.

Exhibit 41 for Declaration of Eric C. Pai in Support of Nevro's Motion for Summary Adjudication (Document 343-41) Rebuttal Expert Report of Richard T. Mihran, Ph.D. dated Feb. 14, 2018, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 23 pages.

Exhibit 42 for Declaration of Eric C. Pai in Support of Nevro's Motion for Summary Adjudication (Document 343-42) Redacted Version of Document Sought to be Sealed—Videotaped Deposition of Nevro Corp. with designated corporate representative Jim Cassidy on May 17, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 5 pages.

Exhibit 43 for Declaration of Eric C. Pai in Support of Nevro's Motion for Summary Adjudication (Document 343-43) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 1 page.

Exhibit 44 for Declaration of Eric C. Pai in Support of Nevro's Motion for Summary Adjudication (Document 343-44) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 1 page.

Exhibit 45 for Declaration of Eric C. Pai in Support of Nevro's Motion for Summary Adjudication (Document 343-45) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 1 page.

Exhibit 46 for Declaration of Eric C. Pai in Support of Nevro's Motion for Summary Adjudication (Document 343-46) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 1 page.

Exhibit 47 for Declaration of Eric C. Pai in Support of Nevro's Motion for Summary Adjudication (Document 343-47) Entire Document Sought to be Sealed—Deposition of Kaoru Lee Adair taken on May 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 1 page.

Exhibit 48 for Declaration of Eric C. Pai in Support of Nevro's Motion for Summary Adjudication (Document 343-48) Defendant's Identification of 40 Prior Art Grounds for Invalidity dated Dec. 22, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 4 pages.

Exhibit 49 for Declaration of Eric C. Pai in Support of Nevro's Motion for Summary Adjudication (Document 343-49) Defendant's Second Amended Preliminary Invalidity Contentions dated Aug. 10, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 47 pages.

Exhibit 50 for Declaration of Eric C. Pai in Support of Nevro's Motion for Summary Adjudication (Document 343-50) Declaration of Rafael Carbunaru in Support of Boston Scientific's Invalidity Contentions dated Mar. 17, 2017, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 6 pages.

Exhibit 51 for Declaration of Eric C. Pai in Support of Nevro's Motion for Summary Adjudication (Document 343-51) Declaration of Kaoru Lee Adair in Support of Boston Scientific's Motion to Dismiss Nevro's Declaratory Judgment Claims dated Dec. 27, 2016, Boston Scientific Corporation's and Boston Scientific Neuromodulation Corporation's Invalidity Contentions, *Nevro Corp.* v. *Boston Scientific Corporation and Boston Scientific Neuromodulation Corporation*, Case No. 3:16-cv-06830-VC (N.D. Cal.), filed Apr. 12, 2018, 5 pages.

Exhibit 52 for Declaration of Eric C. Pai in Support of Nevro's Motion for Summary Adjudication (Document 343-52) Expert Report of Richard T. Mihran, Ph.D., regarding Invalidity of U.S. Pat. No. 8,712,533; U.S. Pat. No. 9,327,125; U.S. Pat. No. 8,359,102; U.S. Pat. No. 9,480,842; U.S. Pat. No. U.S. Pat. No. 9,333,357; U.S. Pat. No. 8,792,988; and U.S. Pat. No. 8,768,472 dated Jan. 18, 2018,

(56) References Cited

OTHER PUBLICATIONS

Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 78 pages.
Exhibit 53 for Declaration of Eric C. Pai in Support of Nevro's Motion for Summary Adjudication (Document 343-53) Redacted Version of Document Sought to be Sealed - Rebuttal Expert Report and Declaration of Daniel Lanovaz dated Feb. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv- 06830-VC (N.D. Cal.), filed Apr. 12, 2018, 6 pages.
Exhibit 54 for Declaration of Eric C. Pai in Support of Nevro's Motion for Summary Adjudication (Document 343-54) Certified Copy of U.S. Pat. No. 8,712,533, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.
Exhibit 55 for Declaration of Eric C. Pai in Support of Nevro's Motion for Summary Adjudication (Document 343-55) Copy of U.S. Patent Application No. 2009/0204173 to Fang et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 33 pages.
Exhibit 56 for Declaration of Eric C. Pai in Support of Nevro's Motion for Summary Adjudication (Document 343-56) Deposition of Konstantinos Alataris dated Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 34 pages.
Exhibit 57 for Declaration of Eric C. Pai in Support of Nevro's Motion for Summary Adjudication (Document 343-57) Videotaped Deposition of Andre B. Walker dated Nov. 10, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 26 pages.
Exhibit 58 for Declaration of Eric C. Pai in Support of Nevro's Motion for Summary Adjudication (Document 343-58) Videotaped Deposition of Zi-Ping Fang dated Nov. 2, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 12 pages.
Exhibit 59 for Declaration of Eric C. Pai in Support of Nevro's Motion for Summary Adjudication (Document 343-59) Videotaped Deposition of Anthony Vincent Caparso dated Nov. 2, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.
Exhibit 60 for Declaration of Eric C. Pai in Support of Nevro's Motion for Summary Adjudication (Document 343-60) Videotaped Deposition of Brian Erickson dated Dec. 15, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 44 pages.
Exhibit 61 for Declaration of Eric C. Pai in Support of Nevro's Motion for Summary Adjudication (Document 343-61) Deposition of Yougandh Chitre dated Nov. 20, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 6 pages.
Exhibit 62 for Declaration of Eric C. Pai in Support of Nevro's Motion for Summary Adjudication (Document 343-62) Deposition of Sangsoo Wesley Park dated Nov. 27, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.
Exhibit 63 for Declaration of Eric C. Pai in Support of Nevro's Motion for Summary Adjudication (Document 343-63) Deposition of Jon Parker dated Nov. 16, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.
Exhibit 64 for Declaration of Eric C. Pai in Support of Nevro's Motion for Summary Adjudication (Document 343-64) Videotaped James Thacker dated Dec. 7, 2017 (vol. 1), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 10 pages.
Exhibit 65 for Declaration of Eric C. Pai in Support of Nevro's Motion for Summary Adjudication (Document 343-65) Sep. 2007 Email between O. Filho and K. Alataris, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 4 pages.
Exhibit 66 for Declaration of Eric C. Pai in Support of Nevro's Motion for Summary Adjudication (Document 343-66) Redacted Version of Document Sought to be Sealed—BSC's Dec. 1, 2017 Supplemental Responses and Objections to Nevro's Second Set of Interrogatories (Nos. 10 and 14), Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 13 pages.
Exhibit 67 for Declaration of Eric C. Pai in Support of Nevro's Motion for Summary Adjudication (Document 343-67) Certified Copy of U.S. Appl. No. 60/985,353, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 63 pages.
Exhibit 68 for Declaration of Eric C. Pai in Support of Nevro's Motion for Summary Adjudication (Document 343-68) Certified Copy of U.S. Appl. No. 12/264,836, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 67 pages.
Exhibit 69 for Declaration of Eric C. Pai in Support of Nevro's Motion for Summary Adjudication (Document 343-69) Certified Copy File Wrapper for U.S. Appl. No. 12/264,836, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 119 pages.
Exhibit 70 for Declaration of Eric C. Pai in Support of Nevro's Motion for Summary Adjudication (Document 343-70) Copy of Request to Add to Originally Named Inventors for U.S. Appl. No. 12/264,836, filed Aug. 13, 2012, Boston Scientific Corporation's and Boston Scientific Neuromodulation Corporation's Invalidity

(56) References Cited

OTHER PUBLICATIONS

Contentions, *Nevro Corp. v. Boston Scientific Corporation and Boston Scientific Neuromodulation Corporation*, Case No. 3:16-cv-06830-VC (N.D. Cal.), filed Apr. 12, 2018, 27 pages.
Exhibit 71 for Declaration of Eric C. Pai in Support of Nevro's Motion for Summary Adjudication (Document 343-71) Poster by Yearwood et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 8 pages.
Exhibit 72 for Declaration of Eric C. Pai in Support of Nevro's Motion for Summary Adjudication (Document 343-72) Case Report by Yearwood et al., Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 3 pages.
Exhibit 73 for Declaration of Eric C. Pai in Support of Nevro's Motion for Summary Adjudication (Document 343-73) Entire Document Sought to be Sealed—Deposition of Rafael Carbunaru taken on Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 1 page.
Exhibit 74 for Declaration of Eric C. Pai in Support of Nevro's Motion for Summary Adjudication (Document 343-74) Deposition of David Caraway dated Nov. 14, 2017, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 9 pages.
Exhibit 75 for Declaration of Eric C. Pai in Support of Nevro's Motion for Summary Adjudication (Document 343-75) Boston Scientific document, Boston Scientific Corporation's and Boston Scientific Neuromodulation Corporation's Invalidity Contentions, *Nevro Corp. v. Boston Scientific Corporation and Boston Scientific Neuromodulation Corporation*, Case No. 3:16-cv-06830-VC (N.D. Cal.), filed Apr. 12, 2018, 5 pages.
Declaration of Carson D. Anderson in Support of Nevro's Administrative Motion to File under Seal Portions of Nevro's Motion for Summary Adjudication and Supporting Documents (Document 348), *Nevro Corp. vs. Boston Scientific Corporation and Boston Scientific Neuromodulation Corporation*, Case No. 3:16-cv-06830-VC-MEJ, Apr. 16, 2018, 10 pages.
Exhibit A for Declaration of Carson D. Anderson in Support of Nevro's Administrative Motion to File under Seal Portions of Nevro's Motion for Summary Adjudication and Supporting Documents (Document 347-1) Redacted Version of Document Sought to Be Filed under Seal—Nevro's Notice of Motion, *Nevro Corp. vs. Boston Scientific Corporation and Boston Scientific Neuromodulation Corporation*, Case No. 3:16-cv-06830-VC-MEJ, Apr. 16, 2018, 50 pages.
Exhibit A—Updated—for Declaration of Carson D. Anderson in Support of Nevro's Administrative Motion to File under Seal Portions of Nevro's Motion for Summary Adjudication and Supporting Documents (Document 347-2 / Document 461) Redacted Version of Document Sought to Be Filed under Seal - Nevro's Motion for Summary Adjudication, *Nevro Corp. vs. Boston Scientific Corporation and Boston Scientific Neuromodulation Corporation*, Case No. 3:16-cv-06830-VC-MEJ, Jul. 30, 2018, 50 pages.
Exhibit B for Declaration of Carson D. Anderson in Support of Nevro's Administrative Motion to File under Seal Portions of Nevro's Motion for Summary Adjudication and Supporting Documents (Document 347-3) Redacted Version of Document Sought to Be Filed under Seal—Videotaped Deposition of Rafael Carbunaru, Ph.D., taken Nov. 15, 2017, *Nevro Corp. vs. Boston Scientific Corporation and Boston Scientific Neuromodulation Corporation*, Case No. 3:16-cv-06830-VC-MEJ, filed Apr. 16, 2018, 46 pages.
Exhibit C for Declaration of Carson D. Anderson in Support of Nevro's Administrative Motion to File under Seal Portions of Nevro's Motion for Summary Adjudication and Supporting Documents (Document 347-5) Boston Scientific Neuromodulation—SPRINT High Rate—Product Opportunity Proposal, *Nevro Corp. vs. Boston Scientific Corporation and Boston Scientific Neuromodulation Corporation*, Case No. 3:16-cv-06830-VC-MEJ, filed Apr. 16, 2018, 14 pages.
Exhibit D for Declaration of Carson D. Anderson in Support of Nevro's Administrative Motion to File under Seal Portions of Nevro's Motion for Summary Adjudication and Supporting Documents (Document 347-7) Redacted Version of Document Sought to be Filed under Seal—Boston Scientific Neuromodulation—SPRINT High Rate—Project Authorization Review, *Nevro Corp. vs. Boston Scientific Corporation and Boston Scientific Neuromodulation Corporation*, Case No. 3:16-cv-06830-VC-MEJ, filed Apr. 16, 2018, 7 pages.
Exhibit E for Declaration of Carson D. Anderson in Support of Nevro's Administrative Motion to File under Seal Portions of Nevro's Motion for Summary Adjudication and Supporting Documents (Document 347-9) Redacted Version of Document Sought to be Filed under Seal—Videotaped Deposition of Kaoru Lee Adair, *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit E—Updated—for Declaration of Carson D. Anderson in Support of Nevro's Administrative Motion to File under Seal Portions of Nevro's Motion for Summary Adjudication and Supporting Documents (Document 347-10) Redacted Version of Document Sought to be Filed under Seal—Videotaped Deposition of Kaoru Lee Adair, taken Nov. 17, 2017, *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit F for Declaration of Carson D. Anderson in Support of Nevro's Administrative Motion to File under Seal Portions of Nevro's Motion for Summary Adjudication and Supporting Documents (Document 347-11) Redacted Version of Document Sought to be Filed under Seal—Videotaped Deposition of Kaoru Lee Adair, taken May 10, 2017, *Nevro Corp. vs. Boston Scientific Corporation and Boston Scientific Neuromodulation Corporation*, Case No. 3:16-cv-06830-VC-MEJ, filed Apr. 16, 2018, 23 pages.
Exhibit F—Updated—for Declaration of Carson D. Anderson in Support of Nevro's Administrative Motion to File under Seal Portions of Nevro's Motion for Summary Adjudication and Supporting Documents (Document 347-12) Redacted Version of Document Sought to be Filed under Seal—Videotaped Deposition of Kaoru Lee Adair, taken May 10, 2017, *Nevro Corp. vs. Boston Scientific Corporation and Boston Scientific Neuromodulation Corporation*, Case No. 3:16-cv-06830-VC-MEJ, filed Apr. 16, 2018, 23 pages.
Exhibit G for Declaration of Carson D. Anderson in Support of Nevro's Administrative Motion to File under Seal Portions of Nevro's Motion for Summary Adjudication and Supporting Documents (Document 347-13) BSC's Supplemental Responses and Objections to Nevro's First Set of Interrogatory Requests (1-8), *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit H for Declaration of Carson D. Anderson in Support of Nevro's Administrative Motion to File under Seal Portions of Nevro's Motion for Summary Adjudication and Supporting Documents (Document 347-15) Redacted Version of Document Sought to be Filed under Seal—BSC's Second Supplemental Responses and Objections to Nevro's First Set of Interrogatory Requests (1-8), *Nevro Corp. vs. Boston Scientific Corporation and Boston Scientific Neuromodulation Corporation*, Case No. 3:16-cv-06830-VC-MEJ, filed Apr. 16, 2018, 12 pages.
Exhibit H—Updated—for Declaration of Carson D. Anderson in Support of Nevro's Administrative Motion to File under Seal Portions of Nevro's Motion for Summary Adjudication and Supporting Documents (Document 347-16) Updated Redacted Version of Document Sought to be Filed under Seal—BSC's Second Supple-

(56) References Cited

OTHER PUBLICATIONS mental Responses and Objections to Nevro's First Set of Interrogatory Requests (1-8), *Nevro Corp. vs. Boston Scientific Corporation and Boston Scientific Neuromodulation Corporation*, Case No. 3:16-cv-06830-VC-MEJ, filed Apr. 16, 2018, 12 pages.

Exhibit I for Declaration of Carson D. Anderson in Support of Nevro's Administrative Motion to File under Seal Portions of Nevro's Motion for Summary Adjudication and Supporting Documents (Document 347-17) Redacted Version of Document Sought to be Filed under Seal—Rebuttal Expert Report of Richard T. Mihran, Ph.D., *Nevro Corp. vs. Boston Scientific Corporation and Boston Scientific Neuromodulation Corporation*, Case No. 3:16-cv-06830-VC-MEJ, filed Apr. 16, 2018, 24 pages.

Exhibit J for Declaration of Carson D. Anderson in Support of Nevro's Administrative Motion to File under Seal Portions of Nevro's Motion for Summary Adjudication and Supporting Documents (Document 347-19) Redacted Version of Document Sought to be Filed under Seal—Oct. 24, 2016 Boston Scientific Letter to U.S. Food and Drug Administration, *Nevro Corp. vs. Boston Scientific Corporation and Boston Scientific Neuromodulation Corporation*, Case No. 3:16-cv-06830-VC-MEJ, filed Apr. 16, 2018, 5 pages.

Exhibit K for Declaration of Carson D. Anderson in Support of Nevro's Administrative Motion to File under Seal Portions of Nevro's Motion for Summary Adjudication and Supporting Documents (Document 347-21) Redacted Version of Document Sought to be Filed under Seal—Rebuttal Expert Report and Declaration of Daniel Lanovaz dated Feb. 14, 2017, *Nevro Corp. vs. Boston Scientific Corporation and Boston Scientific Neuromodulation Corporation*, Case No. 3:16-cv-06830-VC-MEJ, filed Apr. 16, 2018, 7 pages.

Exhibit L for Declaration of Carson D. Anderson in Support of Nevro's Administrative Motion to File under Seal Portions of Nevro's Motion for Summary Adjudication and Supporting Documents (Document 347-23) Redacted Version of Document Sought to be Filed under Seal—Declaration of Ben Pless in Support of Nevro's Motion of Summary Adjudication dated Apr. 12, 2018, *Nevro Corp. vs. Boston Scientific Corporation and Boston Scientific Neuromodulation Corporation*, Case No. 3:16-cv-06830-VC-MEJ, filed Apr. 16, 2018, 64 pages.

Exhibit L—Updated—for Declaration of Carson D. Anderson in Support of Nevro's Administrative Motion to File under Seal Portions of Nevro's Motion for Summary Adjudication and Supporting Documents (Document 347-24) Updated Redacted Version of Document Sought to be Filed under Seal—Declaration of Ben Pless in Support of Nevro's Motion of Summary Adjudication dated Apr. 12, 2018, *Nevro Corp. vs. Boston Scientific Corporation and Boston Scientific Neuromodulation Corporation*, Case No. 3:16-cv-06830-VC-MEJ, filed Apr. 16, 2018, 64 pages.

Declaration of Rafael Carbunaru in Support of Nevro's Administrative Motion to File under Seal Portions of Nevro's Motion for Summary Adjudication and Supporting Documents (Document 347-25), *Nevro Corp. vs. Boston Scientific Corporation and Boston Scientific Neuromodulation Corporation*, Case No. 3:16-cv-06830-VC-MEJ, filed Apr. 16, 2018, 13 pages.

[Proposed] Order Granting Administrative Motion to File under Seal Portions of Nevro's Administrative Motion to File under Seal Portions of Nevro's Motion for Summary Adjudication and Supporting Documents (ECF No. 341) (Document 347-26), *Nevro Corp. vs. Boston Scientific Corporation and Boston Scientific Neuromodulation Corporation*, Case No. 3:16-cv-06830-VC-MEJ, filed Apr. 16, 2018, 5 pages.

Boston Scientific's Responsive Claim Construction Brief, Opposition to Nevro's Motion for Summary Adjudication and Supporting Documents (Document 466), Updated Redacted Version of ECF No. 357-4, *Nevro Corp. vs. Boston Scientific Corporation and Boston Scientific Neuromodulation Corporation*, Case No. 3:16-cv-06830-VC-MEJ, filed Jul. 30, 2018, 61 pages.

Expert Report and Declaration of Gene Fridman, Ph.D., regarding Claim Construction (Document 358-1), *Nevro Corp. vs. Boston Scientific Corporation and Boston Scientific Neuromodulation Corporation*, Case No. 3:16-cv-06830-VC-MEJ, filed Apr. 26, 2018, 18 pages.

Rebuttal Expert Report and Declaration of Gene Fridman, Ph.D., regarding Claim Construction (Document 358-2), *Nevro Corp. vs. Boston Scientific Corporation and Boston Scientific Neuromodulation Corporation*, Case No. 3:16-cv-06830-VC-MEJ, filed Apr. 26, 2018, 11 pages.

Declaration of Richard T. Mihran, Ph.D., regarding Claim Construction Brief (Document 358-3), *Nevro Corp. vs. Boston Scientific Corporation and Boston Scientific Neuromodulation Corporation*, Case No. 3:16-cv-06830-VC-MEJ, filed Apr. 26, 2018, 2 pages.

Exhibit A for Declaration of Richard T. Mihran, Ph.D., regarding Claim Construction Brief (Document 358-4), Expert Report of Richard T. Mihran, Ph.D. regarding Invalidity of U.S. Pat. No. 8,712,533; U.S. Pat. No. 9,327,125; U.S. Pat. No. 8,359,102; U.S. Pat. No. 9,480,842; U.S. Pat. No. 9,333,357; U.S. Pat. No. 8,792,988; and U.S. Pat. No. 8,768,472, *Nevro Corp. vs. Boston Scientific Corporation and Boston Scientific Neuromodulation Corporation*, Case No. 3:16-cv-06830-VC-MEJ, filed Apr. 26, 2018, 129 pages.

Exhibit B Declaration of Richard T. Mihran, Ph.D., regarding Claim Construction Brief (Document 358-5), Redacted Version of Document Sought to be Filed under Seal—Rebuttal Expert Report of Richard T. Mihran, Ph.D., *Nevro Corp. vs. Boston Scientific Corporation and Boston Scientific Neuromodulation Corporation*, Case No. 3:16-cv-06830-VC-MEJ, filed Apr. 26, 2018, 79 pages.

Declaration of Clara W. Wang in Support of Boston Scientific's Responsive regarding Claim Construction Brief; Opposition to Nevro's Motion for Summary Judgement and Opening Motion for Summary Judgement (Document 358-6), *Nevro Corp. vs. Boston Scientific Corporation and Boston Scientific Neuromodulation Corporation*, Case No. 3:16-cv-06830-VC-MEJ, filed Apr. 26, 2018, 8 pages.

Exhibit 1 for Declaration of Clara W. Wang in Support of Boston Scientific's Responsive regarding Claim Construction Brief; Opposition to Nevro's Motion for Summary Judgement and Opening Motion for Summary Judgement (Document 358-7), Sep. 2005 Email between K. Bradley and M. Moffitt, *Nevro Corp. vs. Boston Scientific Corporation and Boston Scientific Neuromodulation Corporation*, Case No. 3:16-cv-06830-VC-MEJ, filed Apr. 26, 2018, 2 pages.

Exhibit 2 for Declaration of Clara W. Wang in Support of Boston Scientific's Responsive regarding Claim Construction Brief; Opposition to Nevro's Motion for Summary Judgement and Opening Motion for Summary Judgement (Document 358-8), Filed under Seal—Document NEVRO_BSXCA0165810-52, *Nevro Corp. vs. Boston Scientific Corporation and Boston Scientific Neuromodulation Corporation*, Case No. 3:16-cv-06830-VC-MEJ, filed Apr. 26, 2018, 1 page.

Exhibit 3 for Declaration of Clara W. Wang in Support of Boston Scientific's Responsive regarding Claim Construction Brief; Opposition to Nevro's Motion for Summary Judgement and Opening Motion for Summary Judgement (Document 358-9), Filed under Seal—Document NEVRO_BSXCA0389050-100, *Nevro Corp. vs. Boston Scientific Corporation and Boston Scientific Neuromodulation Corporation*, Case No. 3:16-cv-06830-VC-MEJ, filed Apr. 26, 2018, 1 page.

Exhibit 4 for Declaration of Clara W. Wang in Support of Boston Scientific's Responsive regarding Claim Construction Brief; Opposition to Nevro's Motion for Summary Judgement and Opening Motion for Summary Judgement (Document 358-10), Summary of Safety and Effectiveness Data (SSED), *Nevro Corp. vs. Boston Scientific Corporation and Boston Scientific Neuromodulation Corporation*, Case No. 3:16-cv-06830-VC-MEJ, filed Apr. 26, 2018, 57 pages.

Exhibit 5 for Declaration of Clara W. Wang in Support of Boston Scientific's Responsive regarding Claim Construction Brief; Opposition to Nevro's Motion for Summary Judgement and Opening Motion for Summary Judgement (Document 358-11), Article by Andres et al., *Nevro Corp. vs. Boston Scientific Corporation and Boston Scientific Neuromodulation Corporation*, Case No. 3:16-cv-06830-VC-MEJ, filed Apr. 26, 2018, 22 pages.

(56) References Cited

OTHER PUBLICATIONS

Exhibit 6 for Declaration of Clara W. Wang in Support of Boston Scientific's Responsive regarding Claim Construction Brief; Opposition to Nevro's Motion for Summary Judgement and Opening Motion for Summary Judgement (Document 358-12), Article by Thomson et al., *Nevro Corp. vs. Boston Scientific Corporation and Boston Scientific Neuromodulation Corporation,* Case No. 3:16-cv-06830-VC-MEJ, filed Apr. 26, 2018, 11 pages.
Exhibit 7 for Declaration of Clara W. Wang in Support of Boston Scientific's Responsive regarding Claim Construction Brief; Opposition to Nevro's Motion for Summary Judgement and Opening Motion for Summary Judgement (Document 358-13), Filed under Seal—Document labeled NEVRO_BSXCA0053540-89, *Nevro Corp. vs. Boston Scientific Corporation and Boston Scientific Neuromodulation Corporation,* Case No. 3:16-cv-06830-VC-MEJ, filed Apr. 26, 2018, 1 page.
Exhibit 8 for Declaration of Clara W. Wang in Support of Boston Scientific's Responsive regarding Claim Construction Brief; Opposition to Nevro's Motion for Summary Judgement and Opening Motion for Summary Judgement (Document 358-14), Filed under Seal—Document labeled NEVRO_BSXCA0055766-70, *Nevro Corp. vs. Boston Scientific Corporation and Boston Scientific Neuromodulation Corporation,* Case No. 3:16-cv-06830-VC-MEJ, filed Apr. 26, 2018, 1 page.
Exhibit 9 for Declaration of Clara W. Wang in Support of Boston Scientific's Responsive regarding Claim Construction Brief; Opposition to Nevro's Motion for Summary Judgement and Opening Motion for Summary Judgement (Document 358-15), Filed under Seal—Document labeled NEVRO_BSXCA0049348-69, *Nevro Corp. vs. Boston Scientific Corporation and Boston Scientific Neuromodulation Corporation,* Case No. 3:16-cv-06830-VC-MEJ, filed Apr. 26, 2018, 1 page.
Exhibit 10 for Declaration of Clara W. Wang in Support of Boston Scientific's Responsive regarding Claim Construction Brief; Opposition to Nevro's Motion for Summary Judgement and Opening Motion for Summary Judgement (Document 358-16), Videotaped Deposition of Rafael Carbunaru, Ph.D., taken on Nov. 15, 2017, *Nevro Corp. vs. Boston Scientific Corporation and Boston Scientific Neuromodulation Corporation,* Case No. 3:16-cv-06830-VC-MEJ, filed Apr. 26, 2018, 9 pages.
Exhibit 11 for Declaration of Clara W. Wang in Support of Boston Scientific's Responsive regarding Claim Construction Brief; Opposition to Nevro's Motion for Summary Judgement and Opening Motion for Summary Judgement (Document 358-17), Redacted Version of Document Sought to be Filed under Sealed—Videotaped Deposition of Jim Cassidy, taken on Nov. 29, 2017, *Nevro Corp. vs. Boston Scientific Corporation and Boston Scientific Neuromodulation Corporation,* Case No. 3:16-cv-06830-VC-MEJ, filed Apr. 26, 2018, 9 pages.
Exhibit 12 for Declaration of Clara W. Wang in Support of Boston Scientific's Responsive regarding Claim Construction Brief; Opposition to Nevro's Motion for Summary Judgement and Opening Motion for Summary Judgement (Document 467), Filed under Sealed—Videotaped Deposition of Kaoru Lee Adair, taken on Nov. 17, 2017, *Nevro Corp. vs. Boston Scientific Corporation and Boston Scientific Neuromodulation Corporation,* Case No. 3:16-cv-06830-VC-MEJ, filed Apr. 26, 2018, 10 pages.
Exhibit 13 for Declaration of Clara W. Wang in Support of Boston Scientific's Responsive regarding Claim Construction Brief; Opposition to Nevro's Motion for Summary Judgement and Opening Motion for Summary Judgement (Document 358-19), Redacted Version of Document Sought to be Filed under Seal—Videotaped Deposition of Jim Cassidy, taken on Nov. 30, 2017, *Nevro Corp. vs. Boston Scientific Corporation and Boston Scientific Neuromodulation Corporation,* Case No. 3:16-cv-06830-VC-MEJ, filed Apr. 26, 2018, 10 pages.
Exhibit 14 for Declaration of Clara W. Wang in Support of Boston Scientific's Responsive regarding Claim Construction Brief; Opposition to Nevro's Motion for Summary Judgement and Opening Motion for Summary Judgement (Document 358-20), Apr. 2018 Email between K. Carter and MoFo-NevroBSX, taken on Nov. 30, 2017, *Nevro Corp. vs. Boston Scientific Corporation and Boston Scientific Neuromodulation Corporation,* Case No. 3:16-cv-06830-VC-MEJ, filed Apr. 26, 2018, 2 pages.
Exhibit 15 for Declaration of Clara W. Wang in Support of Boston Scientific's Responsive regarding Claim Construction Brief; Opposition to Nevro's Motion for Summary Judgement and Opening Motion for Summary Judgement (Document 358-21), Boston Scientific Advancing Science for Life—Technical Sales Training, *Nevro Corp. vs. Boston Scientific Corporation and Boston Scientific Neuromodulation Corporation,* Case No. 3:16-cv-06830-VC-MEJ, filed Apr. 26, 2018, 3 pages.
Exhibit 16 for Declaration of Clara W. Wang in Support of Boston Scientific's Responsive regarding Claim Construction Brief; Opposition to Nevro's Motion for Summary Judgement and Opening Motion for Summary Judgement (Document 358-22), Product Specification for Ninja System, *Nevro Corp. vs. Boston Scientific Corporation and Boston Scientific Neuromodulation Corporation,* Case No. 3:16-cv-06830-VC-MEJ, filed Apr. 26, 2018, 3 pages.
Exhibit 17 for Declaration of Clara W. Wang in Support of Boston Scientific's Responsive regarding Claim Construction Brief; Opposition to Nevro's Motion for Summary Judgement and Opening Motion for Summary Judgement (Document 358-23), Deposition of Ben Pless, taken on Apr. 10, 2018, *Nevro Corp. vs. Boston Scientific Corporation and Boston Scientific Neuromodulation Corporation,* Case No. 3:16-cv-06830-VC-MEJ, filed Apr. 26, 2018, 3 pages.
Exhibit 18 for Declaration of Clara W. Wang in Support of Boston Scientific's Responsive regarding Claim Construction Brief; Opposition to Nevro's Motion for Summary Judgement and Opening Motion for Summary Judgement (Document 358-24), Merriam-Webster's Collegiate Dictionary, *Nevro Corp. vs. Boston Scientific Corporation and Boston Scientific Neuromodulation Corporation,* Case No. 3:16-cv-06830-VC-MEJ, filed Apr. 26, 2018, 5 pages.
Exhibit 19 for Declaration of Clara W. Wang in Support of Boston Scientific's Responsive regarding Claim Construction Brief; Opposition to Nevro's Motion for Summary Judgement and Opening Motion for Summary Judgement (Document 358-25), Merriam-Webster's Collegiate Dictionary, *Nevro Corp. vs. Boston Scientific Corporation and Boston Scientific Neuromodulation Corporation,* Case No. 3:16-cv-06830-VC-MEJ, filed Apr. 26, 2018, 5 pages.
Exhibit 20 for Declaration of Clara W. Wang in Support of Boston Scientific's Responsive regarding Claim Construction Brief; Opposition to Nevro's Motion for Summary Judgement and Opening Motion for Summary Judgement (Document 358-26), Concise Oxford Dictionary, *Nevro Corp. vs. Boston Scientific Corporation and Boston Scientific Neuromodulation Corporation,* Case No. 3:16-cv-06830-VC-MEJ, filed Apr. 26, 2018, 5 pages.
Exhibit 21 for Declaration of Clara W. Wang in Support of Boston Scientific's Responsive regarding Claim Construction Brief; Opposition to Nevro's Motion for Summary Judgement and Opening Motion for Summary Judgement (Document 358-27), Final Office Action for U.S. Appl. No. 15/134,285, issued Nov. 28, 2017, *Nevro Corp. vs. Boston Scientific Corporation and Boston Scientific Neuromodulation Corporation,* Case No. 3:16-cv-06830-VC-MEJ, filed Apr. 26, 2018, 22 pages.
Exhibit 22 for Declaration of Clara W. Wang in Support of Boston Scientific's Responsive regarding Claim Construction Brief; Opposition to Nevro's Motion for Summary Judgement and Opening Motion for Summary Judgement (Document 358-28), U.S. Pat. No. 8,355,797 by Caparso et al., *Nevro Corp. vs. Boston Scientific Corporation and Boston Scientific Neuromodulation Corporation,* Case No. 3:16-cv-06830-VC-MEJ, filed Apr. 26, 2018, 21 pages.
Exhibit 23 for Declaration of Clara W. Wang in Support of Boston Scientific's Responsive regarding Claim Construction Brief; Opposition to Nevro's Motion for Summary Judgement and Opening Motion for Summary Judgement (Document 358-29), Redacted Version of the Document Sought to be Filed under Seal—Deposition of Jon Parker dated Nov. 16, 2017, *Nevro Corp. vs. Boston Scientific Corporation and Boston Scientific Neuromodulation Corporation,* Case No. 3:16-cv-06830-VC-MEJ, filed Apr. 26, 2018, 12 pages.
Exhibit 24 for Declaration of Clara W. Wang in Support of Boston Scientific's Responsive regarding Claim Construction Brief; Oppo-

(56) References Cited

OTHER PUBLICATIONS sition to Nevro's Motion for Summary Judgement and Opening Motion for Summary Judgement (Document 358-30), Redacted Version of the Document Sought to be Filed under Seal—Corrected Rebuttal Expert Report of Ben Plesss regarding Validity dated Mar. 5, 2018, *Nevro Corp.* vs. *Boston Scientific Corporation and Boston Scientific Neuromodulation Corporation,* Case No. 3:16-cv-06830-VC-MEJ, filed Apr. 26, 2018, 55 pages.

Exhibit 25 for Declaration of Clara W. Wang in Support of Boston Scientific's Responsive regarding Claim Construction Brief; Opposition to Nevro's Motion for Summary Judgement and Opening Motion for Summary Judgement (Document 358-31), Deposition of Dr. Gene Fridman dated Mar. 7, 2018, *Nevro Corp.* vs. *Boston Scientific Corporation and Boston Scientific Neuromodulation Corporation,* Case No. 3:16-cv-06830-VC-MEJ, filed Apr. 26, 2018, 14 pages.

Exhibit 26 for Declaration of Clara W. Wang in Support of Boston Scientific's Responsive regarding Claim Construction Brief; Opposition to Nevro's Motion for Summary Judgement and Opening Motion for Summary Judgement (Document 358-32), Redacted Version of Document Sought to be Filed under Seal—Opening Expert Report of Ben Pless regarding Infringement dated Jan. 18, 2018, *Nevro Corp.* vs. *Boston Scientific Corporation and Boston Scientific Neuromodulation Corporation,* Case No. 3:16-cv-06830-VC-MEJ, filed Apr. 26, 2018, 23 pages.

Exhibit 27 for Declaration of Clara W. Wang in Support of Boston Scientific's Responsive regarding Claim Construction Brief; Opposition to Nevro's Motion for Summary Judgement and Opening Motion for Summary Judgement (Document 358-33), U.S. Patent Application Publication No. 2017/0050021 to Cosman Sr., *Nevro Corp.* vs. *Boston Scientific Corporation and Boston Scientific Neuromodulation Corporation,* Case No. 3:16-cv-06830-VC-MEJ, filed Apr. 26, 2018, 32 pages.

Exhibit 28 for Declaration of Clara W. Wang in Support of Boston Scientific's Responsive regarding Claim Construction Brief; Opposition to Nevro's Motion for Summary Judgement and Opening Motion for Summary Judgement (Document 358-34), Expert Report of William S. Rosenberg, MD, FAANS, dated Jan. 18, 2018, *Nevro Corp.* vs. *Boston Scientific Corporation and Boston Scientific Neuromodulation Corporation,* Case No. 3:16-cv-06830-VC-MEJ, filed Apr. 26, 2018, 4 pages.

Exhibit 29 for Declaration of Clara W. Wang in Support of Boston Scientific's Responsive regarding Claim Construction Brief; Opposition to Nevro's Motion for Summary Judgement and Opening Motion for Summary Judgement (Document 358-35), Declaration of David Caraway, M.D. Ph.D., dated Feb. 16, 2016, *Nevro Corp.* vs. *Boston Scientific Corporation and Boston Scientific Neuromodulation Corporation,* Case No. 3:16-cv-06830-VC-MEJ, filed Apr. 26, 2018, 8 pages.

Exhibit 30 for Declaration of Clara W. Wang in Support of Boston Scientific's Responsive regarding Claim Construction Brief; Opposition to Nevro's Motion for Summary Judgement and Opening Motion for Summary Judgement (Document 358-36), Filed under Seal—Document NEVRO_BSXCA0073295-300, *Nevro Corp.* vs. *Boston Scientific Corporation and Boston Scientific Neuromodulation Corporation,* Case No. 3:16-cv-06830-VC-MEJ, filed Apr. 26, 2018, 1 page.

Exhibit 31 for Declaration of Clara W. Wang in Support of Boston Scientific's Responsive regarding Claim Construction Brief; Opposition to Nevro's Motion for Summary Judgement and Opening Motion for Summary Judgement (Document 358-37), Article by Alexander J.R. Macdonald et al., *Nevro Corp.* vs. *Boston Scientific Corporation and Boston Scientific Neuromodulation Corporation,* Case No. 3:16-cv-06830-VC-MEJ, filed Apr. 26, 2018, 10 pages.

Exhibit 32 for Declaration of Clara W. Wang in Support of Boston Scientific's Responsive regarding Claim Construction Brief; Opposition to Nevro's Motion for Summary Judgement and Opening Motion for Summary Judgement (Document 358-38), U.S. Pat. No. 5,776,170 to MacDonald et al., *Nevro Corp.* vs. *Boston Scientific Corporation and Boston Scientific Neuromodulation Corporation,* Case No. 3:16-cv-06830-VC-MEJ, filed Apr. 26, 2018, 12 pages.

Exhibit 33 for Declaration of Clara W. Wang in Support of Boston Scientific's Responsive regarding Claim Construction Brief; Opposition to Nevro's Motion for Summary Judgement and Opening Motion for Summary Judgement (Document 358-39), File History for U.S. Appl. No. 14/525,134, issued Mar. 12, 2015, *Nevro Corp.* vs. *Boston Scientific Corporation and Boston Scientific Neuromodulation Corporation,* Case No. 3:16-cv-06830-VC-MEJ, filed Apr. 26, 2018, 34 pages.

Exhibit 34 for Declaration of Clara W. Wang in Support of Boston Scientific's Responsive regarding Claim Construction Brief; Opposition to Nevro's Motion for Summary Judgement and Opening Motion for Summary Judgement (Document 358-40), Filed under Seal—Document NEVRO_BSXCA0108347-8, *Nevro Corp.* vs. *Boston Scientific Corporation and Boston Scientific Neuromodulation Corporation,* Case No. 3:16-cv-06830-VC-MEJ, filed Apr. 26, 2018, 1 page.

Exhibit 35 for Declaration of Clara W. Wang in Support of Boston Scientific's Responsive regarding Claim Construction Brief; Opposition to Nevro's Motion for Summary Judgement and Opening Motion for Summary Judgement (Document 358-41), Non-Final Office Action for U.S. Appl. No. 14/503,259, issued Dec. 3, 2015, *Nevro Corp.* vs. *Boston Scientific Corporation and Boston Scientific Neuromodulation Corporation,* Case No. 3:16-cv-06830-VC-MEJ, filed Apr. 26, 2018, 11 pages.

Exhibit 36 for Declaration of Clara W. Wang in Support of Boston Scientific's Responsive regarding Claim Construction Brief; Opposition to Nevro's Motion for Summary Judgement and Opening Motion for Summary Judgement (Document 358-42), Documents from File History for U.S. Appl. No. 14/261,369, *Nevro Corp.* vs. *Boston Scientific Corporation and Boston Scientific Neuromodulation Corporation,* Case No. 3:16-cv-06830-VC-MEJ, filed Apr. 26, 2018, 59 pages.

Exhibit 37 for Declaration of Clara W. Wang in Support of Boston Scientific's Responsive regarding Claim Construction Brief; Opposition to Nevro's Motion for Summary Judgement and Opening Motion for Summary Judgement (Document 358-43), Final Office Action for U.S. Appl. No. 15/134,285, issued Nov. 28, 2017, *Nevro Corp.* vs. *Boston Scientific Corporation and Boston Scientific Neuromodulation Corporation,* Case No. 3:16-cv-06830-VC-MEJ, filed Apr. 26, 2018, 22 pages.

Exhibit 38 for Declaration of Clara W. Wang in Support of Boston Scientific's Responsive regarding Claim Construction Brief; Opposition to Nevro's Motion for Summary Judgement and Opening Motion for Summary Judgement (Document 358-44), U.S. National Library of Medicine—ClinicalTrials.gov, *Nevro Corp.* vs. *Boston Scientific Corporation and Boston Scientific Neuromodulation Corporation,* Case No. 3:16-cv-06830-VC-MEJ, filed Apr. 26, 2018, 6 pages.

Exhibit 39 for Declaration of Clara W. Wang in Support of Boston Scientific's Responsive regarding Claim Construction Brief; Opposition to Nevro's Motion for Summary Judgement and Opening Motion for Summary Judgement (Document 358-45), Redacted Version of Document Sought to be Filed under Seal—Jan. 23, 2014 Correspondence to Boston Scientific Corporation, *Nevro Corp.* vs. *Boston Scientific Corporation and Boston Scientific Neuromodulation Corporation,* Case No. 3:16-cv-06830-VC-MEJ, filed Apr. 26, 2018, 10 pages.

Exhibit 40 for Declaration of Clara W. Wang in Support of Boston Scientific's Responsive regarding Claim Construction Brief; Opposition to Nevro's Motion for Summary Judgement and Opening Motion for Summary Judgement (Document 358-46), Redacted Version of Document Sought to be Filed under Seal—Nov. 23, 2016 Email and Correspondence to Kaoru Adair, *Nevro Corp.* vs. *Boston Scientific Corporation and Boston Scientific Neuromodulation Corporation,* Case No. 3:16-cv-06830-VC-MEJ, filed Apr. 26, 2018, 8 pages.

Exhibit 41 for Declaration of Clara W. Wang in Support of Boston Scientific's Responsive regarding Claim Construction Brief; Opposition to Nevro's Motion for Summary Judgement and Opening Motion for Summary Judgement (Document 358-47), Boston Scientific—Investigational Device Exemption (IDE) Application, sub-

(56) References Cited

OTHER PUBLICATIONS mission date Feb. 21, 2013, *Nevro Corp. vs. Boston Scientific Corporation and Boston Scientific Neuromodulation Corporation*, Case No. 3:16-cv-06830-VC-MEJ, filed Apr. 26, 2018, 5 pages.

Exhibit 42 for Declaration of Clara W. Wang in Support of Boston Scientific's Responsive regarding Claim Construction Brief; Opposition to Nevro's Motion for Summary Judgement and Opening Motion for Summary Judgement (Document 358-48), Redacted Version of Document Sought to be Filed under Seal—Boston Scientific—A Randomized Controlled Study to Evaluate the Safety and Effectiveness of the Precision Spinal Cord Stimulator System Adapted for High-Rate Spinal Cord Stimulation, *Nevro Corp. vs. Boston Scientific Corporation and Boston Scientific Neuromodulation Corporation*, Case No. 3:16-cv-06830-VC-MEJ, filed Apr. 26, 2018, 5 pages.

Exhibit 43 for Declaration of Clara W. Wang in Support of Boston Scientific's Responsive regarding Claim Construction Brief; Opposition to Nevro's Motion for Summary Judgement and Opening Motion for Summary Judgement (Document 358-49), World Medical Association—WMA Declaration of Helsinki—Ethical Principles for Medical Research Involving Human Subjects, *Nevro Corp. vs. Boston Scientific Corporation and Boston Scientific Neuromodulation Corporation*, Case No. 3:16-cv-06830-VC-MEJ, filed Apr. 26, 2018, 3 pages.

Exhibit 44 for Declaration of Clara W. Wang in Support of Boston Scientific's Responsive regarding Claim Construction Brief; Opposition to Nevro's Motion for Summary Judgement and Opening Motion for Summary Judgement (Document 358-50), U.S. Patent Application Publication No. 2007/0073354 to Knudson et al., *Nevro Corp. vs. Boston Scientific Corporation and Boston Scientific Neuromodulation Corporation*, Case No. 3:16-cv-06830-VC-MEJ, filed Apr. 26, 2018, 15 pages.

Exhibit 45 for Declaration of Clara W. Wang in Support of Boston Scientific's Responsive regarding Claim Construction Brief; Opposition to Nevro's Motion for Summary Judgement and Opening Motion for Summary Judgement (Document 358-51), U.S. Patent Application Publication No. 2007/0060954 to Cameron et al., *Nevro Corp. vs. Boston Scientific Corporation and Boston Scientific Neuromodulation Corporation*, Case No. 3:16-cv-06830-VC-MEJ, filed Apr. 26, 2018, 21 pages.

Exhibit 46 for Declaration of Clara W. Wang in Support of Boston Scientific's Responsive regarding Claim Construction Brief; Opposition to Nevro's Motion for Summary Judgement and Opening Motion for Summary Judgement (Document 358-52), Documents from File History for U.S. Appl. No. 12/765,747, *Nevro Corp. vs. Boston Scientific Corporation and Boston Scientific Neuromodulation Corporation*, Case No. 3:16-cv-06830-VC-MEJ, filed Apr. 26, 2018, 57 pages.

Exhibit 47 for Declaration of Clara W. Wang in Support of Boston Scientific's Responsive regarding Claim Construction Brief; Opposition to Nevro's Motion for Summary Judgement and Opening Motion for Summary Judgement (Document 358-53), Response to Final Office Action for U.S. Appl. No. 14/292,671, filed Jan. 17, 2017, *Nevro Corp. vs. Boston Scientific Corporation and Boston Scientific Neuromodulation Corporation*, Case No. 3:16-cv-06830-VC-MEJ, filed Apr. 26, 2018, 12 pages.

Exhibit 48 for Declaration of Clara W. Wang in Support of Boston Scientific's Responsive regarding Claim Construction Brief; Opposition to Nevro's Motion for Summary Judgement and Opening Motion for Summary Judgement (Document 358-54), Response to Non-Final Office Action for U.S. Appl. No. 14/503,259, filed Mar. 16, 2015, *Nevro Corp. vs. Boston Scientific Corporation and Boston Scientific Neuromodulation Corporation*, Case No. 3:16-cv-06830-VC-MEJ, filed Apr. 26, 2018, 30 pages.

Exhibit 49 for Declaration of Clara W. Wang in Support of Boston Scientific's Responsive regarding Claim Construction Brief; Opposition to Nevro's Motion for Summary Judgement and Opening Motion for Summary Judgement (Document 358-55), Redacted Version of Document Sought to be Filed under Seal—Deposition of Konstantinos Alataris dated Nov. 14, 2017, *Nevro Corp. vs. Boston Scientific Corporation and Boston Scientific Neuromodulation Corporation*, Case No. 3:16-cv-06830-VC-MEJ, filed Apr. 26, 2018, 21 pages.

Exhibit 50 for Declaration of Clara W. Wang in Support of Boston Scientific's Responsive regarding Claim Construction Brief; Opposition to Nevro's Motion for Summary Judgement and Opening Motion for Summary Judgement (Document 358-56), Chart for Asserted Claims by Limitation Category, *Nevro Corp. vs. Boston Scientific Corporation and Boston Scientific Neuromodulation Corporation*, Case No. 3:16-cv-06830-VC-MEJ, filed Apr. 26, 2018, 12 pages.

Exhibit 51 for Declaration of Clara W. Wang in Support of Boston Scientific's Responsive regarding Claim Construction Brief; Opposition to Nevro's Motion for Summary Judgement and Opening Motion for Summary Judgement (Document 358-57), U.S. Patent Application Publication No. 2009/0204173 to Fang et al., *Nevro Corp. vs. Boston Scientific Corporation and Boston Scientific Neuromodulation Corporation*, Case No. 3:16-cv-06830-VC-MEJ, filed Apr. 26, 2018, 33 pages.

Exhibit 52 for Declaration of Clara W. Wang in Support of Boston Scientific's Responsive regarding Claim Construction Brief; Opposition to Nevro's Motion for Summary Judgement and Opening Motion for Summary Judgement (Document 358-58), Applicant-Initiated Interview Summary for U.S. Appl. No. 14/037,262, issued Feb. 25, 2014, *Nevro Corp. vs. Boston Scientific Corporation and Boston Scientific Neuromodulation Corporation*, Case No. 3:16-cv-06830-VC-MEJ, filed Apr. 26, 2018, 5 pages.

Exhibit 53 for Declaration of Clara W. Wang in Support of Boston Scientific's Responsive regarding Claim Construction Brief; Opposition to Nevro's Motion for Summary Judgement and Opening Motion for Summary Judgement (Document 358-59), Redacted Version of Document Sought to be Filed under Seal—Videotaped Deposition of Zi-Ping Fang dated Nov. 2, 2017, *Nevro Corp. vs. Boston Scientific Corporation and Boston Scientific Neuromodulation Corporation*, Case No. 3:16-cv-06830-VC-MEJ, filed Apr. 26, 2018, 16 pages.

Exhibit 54 for Declaration of Clara W. Wang in Support of Boston Scientific's Responsive regarding Claim Construction Brief; Opposition to Nevro's Motion for Summary Judgement and Opening Motion for Summary Judgement (Document 358-60), Handwritten Figure, *Nevro Corp. vs. Boston Scientific Corporation and Boston Scientific Neuromodulation Corporation*, Case No. 3:16-cv-06830-VC-MEJ, filed Apr. 26, 2018, 3 pages.

Exhibit 55 for Declaration of Clara W. Wang in Support of Boston Scientific's Responsive regarding Claim Construction Brief; Opposition to Nevro's Motion for Summary Judgement and Opening Motion for Summary Judgement (Document 358-61), Handwritten Figure, *Nevro Corp. vs. Boston Scientific Corporation and Boston Scientific Neuromodulation Corporation*, Case No. 3:16-cv-06830-VC-MEJ, filed Apr. 26, 2018, 3 pages.

Exhibit 56 for Declaration of Clara W. Wang in Support of Boston Scientific's Responsive regarding Claim Construction Brief; Opposition to Nevro's Motion for Summary Judgement and Opening Motion for Summary Judgement (Document 358-62), Declaration of Rafael Cabunaru in Support of Boston Scientific's Invalidity Contentions, *Nevro Corp. vs. Boston Scientific Corporation and Boston Scientific Neuromodulation Corporation*, Case No. 3:16-cv-06830-VC-MEJ, filed Apr. 26, 2018, 132 pages.

Exhibit 57 for Declaration of Clara W. Wang in Support of Boston Scientific's Responsive regarding Claim Construction Brief; Opposition to Nevro's Motion for Summary Judgement and Opening Motion for Summary Judgement (Document 358-63), Deposition of David Caraway, M.D., Ph.D., dated Nov. 14, 2017, *Nevro Corp. vs. Boston Scientific Corporation and Boston Scientific Neuromodulation Corporation*, Case No. 3:16-cv-06830-VC-MEJ, filed Apr. 26, 2018, 15 pages.

Exhibit 58 for Declaration of Clara W. Wang in Support of Boston Scientific's Responsive regarding Claim Construction Brief; Opposition to Nevro's Motion for Summary Judgement and Opening Motion for Summary Judgement (Document 358-64), Filed under Seal—Document NEVRO_BSXCA0209790-812, *Nevro Corp. vs.*

(56) References Cited

OTHER PUBLICATIONS

*Boston Scientific Corporation and Boston Scientific Neuromodulation Corporation,* Case No. 3:16-cv-06830-VC-MEJ, filed Apr. 26, 2018, 1 page.
Exhibit 59 for Declaration of Clara W. Wang in Support of Boston Scientific's Responsive regarding Claim Construction Brief; Opposition to Nevro's Motion for Summary Judgement and Opening Motion for Summary Judgement (Document 358-65), Videotaped Deposition of Dr. James North taken on Nov. 18, 2017, *Nevro Corp. vs. Boston Scientific Corporation and Boston Scientific Neuromodulation Corporation,* Case No. 3:16-cv-06830-VC-MEJ, filed Apr. 26, 2018, 11 pages.
Exhibit 60 for Declaration of Clara W. Wang in Support of Boston Scientific's Responsive regarding Claim Construction Brief; Opposition to Nevro's Motion for Summary Judgement and Opening Motion for Summary Judgement (Document 358-66), Videotaped Deposition of Robert Nathan taken on Nov. 15, 2017, *Nevro Corp. vs. Boston Scientific Corporation and Boston Scientific Neuromodulation Corporation,* Case No. 3:16-cv-06830-VC-MEJ, filed Apr. 26, 2018, 11 pages.
Exhibit 61 for Declaration of Clara W. Wang in Support of Boston Scientific's Responsive regarding Claim Construction Brief; Opposition to Nevro's Motion for Summary Judgement and Opening Motion for Summary Judgement (Document 358-67), Case Report by Yearwood et al., *Nevro Corp. vs. Boston Scientific Corporation and Boston Scientific Neuromodulation Corporation,* Case No. 3:16-cv-06830-VC-MEJ, filed Apr. 26, 2018, 3 pages.
Exhibit 62 for Declaration of Clara W. Wang in Support of Boston Scientific's Responsive regarding Claim Construction Brief; Opposition to Nevro's Motion for Summary Judgement and Opening Motion for Summary Judgement (Document 358-68), Videotaped Deposition of Dr. William S. Rosenberg dated Mar. 21, 2018, *Nevro Corp. vs. Boston Scientific Corporation and Boston Scientific Neuromodulation Corporation,* Case No. 3:16-cv-06830-VC-MEJ, filed Apr. 26, 2018, 11 pages.
Exhibit 63 for Declaration of Clara W. Wang in Support of Boston Scientific's Responsive regarding Claim Construction Brief; Opposition to Nevro's Motion for Summary Judgement and Opening Motion for Summary Judgement (Document 358-69), Document by Yearwood et al., *Nevro Corp. vs. Boston Scientific Corporation and Boston Scientific Neuromodulation Corporation,* Case No. 3:16-cv-06830-VC-MEJ, filed Apr. 26, 2018, 8 pages.
Exhibit 64 for Declaration of Clara W. Wang in Support of Boston Scientific's Responsive regarding Claim Construction Brief; Opposition to Nevro's Motion for Summary Judgement and Opening Motion for Summary Judgement (Document 358-70), Redacted Version of Document Sought to be Filed under Seal—Videotaped Deposition of James Thacker (vol. I) dated Dec. 7, 2017, *Nevro Corp. vs. Boston Scientific Corporation and Boston Scientific Neuromodulation Corporation,* Case No. 3:16-cv-06830-VC-MEJ, filed Apr. 26, 2018, 35 pages.
Exhibit 65 for Declaration of Clara W. Wang in Support of Boston Scientific's Responsive regarding Claim Construction Brief; Opposition to Nevro's Motion for Summary Judgement and Opening Motion for Summary Judgement (Document 358-71), Filed under Seal—Document NEVRO_BSXCA0118164-203, *Nevro Corp. vs. Boston Scientific Corporation and Boston Scientific Neuromodulation Corporation,* Case No. 3:16-cv-06830-VC-MEJ, filed Apr. 26, 2018, 1 page.
Exhibit 66 for Declaration of Clara W. Wang in Support of Boston Scientific's Responsive regarding Claim Construction Brief; Opposition to Nevro's Motion for Summary Judgement and Opening Motion for Summary Judgement (Document 358-72), Videotaped Deposition of Kerry Bradley dated Nov. 8, 2017, *Nevro Corp. vs. Boston Scientific Corporation and Boston Scientific Neuromodulation Corporation,* Case No. 3:16-cv-06830-VC-MEJ, filed Apr. 26, 2018, 10 pages.
Exhibit 67 for Declaration of Clara W. Wang in Support of Boston Scientific's Responsive regarding Claim Construction Brief; Opposition to Nevro's Motion for Summary Judgement and Opening Motion for Summary Judgement (Document 358-73), Response to Final Office Action for U.S. Appl. No. 12/765,685, filed Sep. 19, 2013, *Nevro Corp. vs. Boston Scientific Corporation and Boston Scientific Neuromodulation Corporation,* Case No. 3:16-cv-06830-VC-MEJ, filed Apr. 26, 2018, 15 pages.
Exhibit 68 for Declaration of Clara W. Wang in Support of Boston Scientific's Responsive regarding Claim Construction Brief; Opposition to Nevro's Motion for Summary Judgement and Opening Motion for Summary Judgement (Document 358-74), Response to Non-Final Office Action for U.S. Appl. No. 13/830,992, filed Feb. 24, 2014, *Nevro Corp. vs. Boston Scientific Corporation and Boston Scientific Neuromodulation Corporation,* Case No. 3:16-cv-06830-VC-MEJ, filed Apr. 26, 2018, 15 pages.
Rebuttal Expert Report and Declaration of Daniel Lanovaz (Document 359), *Nevro Corp. vs. Boston Scientific Corporation and Boston Scientific Neuromodulation Corporation,* Case No. 3:16-cv-06830-VC-MEJ, filed Apr. 26, 2018, 10 pages.
Nevro's Reply in Support of its Motion for Summary Adjudication and Opposition to BSC's Motion for Summary Judgement (Document 468), Updated Redacted Version of ECF No. 382-2, *Nevro Corp. vs. Boston Scientific Corporation and Boston Scientific Neuromodulation Corporation,* Case No. 3:16-cv-06830-VC-MEJ, filed Jul. 30, 2018, 40 pages.
Declaration of Joshua Goshorn in Support of Nevro's Reply in Support of Motion for Summary Adjudication and Opposition to BSC's Motion for Summary Judgement (Document 375), *Nevro Corp. vs. Boston Scientific Corporation and Boston Scientific Neuromodulation Corporation,* Case No. 3:16-cv-06830-VC-MEJ, filed May 10, 2018, 2 pages.
Exhibit A for Declaration of Joshua Goshorn in Support of Nevro's Reply in Support of Motion for Summary Adjudication and Opposition to BSC's Motion for Summary Judgement (Document 375-1), Entire Document Sought—Joshua Goshorn opening Expert Report, *Nevro Corp. vs. Boston Scientific Corporation and Boston Scientific Neuromodulation Corporation,* Case No. 3:16-cv-06830-VC-MEJ, filed May 10, 2018, 1 page.
Declaration of Ben Pless in Support of Nevro's Reply in Support of Motion for Summary Adjudication and Opposition to BSC's Motion for Summary Judgement (Document 376), *Nevro Corp. vs. Boston Scientific Corporation and Boston Scientific Neuromodulation Corporation,* Case No. 3:16-cv-06830-VC-MEJ, filed May 10, 2018, 2 pages.
Exhibit A for Declaration of Ben Pless in Support of Nevro's Reply in Support of Motion for Summary Adjudication and Opposition to BSC's Motion for Summary Judgement (Document 376-1), Redacted Version of Document Sought to be Sealed—Opening Expert Report of Ben Pless, *Nevro Corp. vs. Boston Scientific Corporation and Boston Scientific Neuromodulation Corporation,* Case No. 3:16-cv-06830-VC-MEJ, filed May 10, 2018, 151 pages.
Exhibit B for Declaration of Ben Pless in Support of Nevro's Reply in Support of Motion for Summary Adjudication and Opposition to BSC's Motion for Summary Judgement (Document 376-2), Redacted Version of Document Sought to be Sealed—Corrected Rebuttal Expert Report of Ben Pless regarding Validity, dated Mar. 5, 2018, *Nevro Corp. vs. Boston Scientific Corporation and Boston Scientific Neuromodulation Corporation,* Case No. 3:16-cv-06830-VC-MEJ, filed May 10, 2018, 116 pages.
Declaration of William Sanford Rosenberg in Support of Nevro's Reply in Support of Motion for Summary Adjudication and Opposition to BSC's Motion for Summary Judgement (Document 377), *Nevro Corp. vs. Boston Scientific Corporation and Boston Scientific Neuromodulation Corporation,* Case No. 3:16-cv-06830-VC-MEJ, filed May 10, 2018, 2 pages.
Exhibit A for Declaration of William Sanford Rosenberg in Support of Nevro's Reply in Support of Motion for Summary Adjudication and Opposition to BSC's Motion for Summary Judgement (Document 377-1), Curriculum Vitae of William Sanford Rosenberg, M.D., *Nevro Corp. vs. Boston Scientific Corporation and Boston Scientific Neuromodulation Corporation,* Case No. 3:16-cv-06830-VC-MEJ, filed May 10, 2018, 21 pages.
Exhibit B for Declaration of William Sanford Rosenberg in Support of Nevro's Reply in Support of Motion for Summary Adjudication and Opposition to BSC's Motion for Summary Judgement (Docu-

(56) References Cited

OTHER PUBLICATIONS ment 377-2), Redacted Version of Document Sought to be Sealed—Deposition of William Sanford Rosenberg, M.D. FAAMS, *Nevro Corp. vs. Boston Scientific Corporation and Boston Scientific Neuromodulation Corporation*, Case No. 3:16-cv-06830-VC-MEJ, filed May 10, 2018, 40 pages.

Declaration of Robert Schiff in Support of Nevro's Reply in Support of Motion for Summary Adjudication and Opposition to BSC's Motion for Summary Judgement (Document 378), *Nevro Corp. vs. Boston Scientific Corporation and Boston Scientific Neuromodulation Corporation*, Case No. 3:16-cv-06830-VC-MEJ, filed May 10, 2018, 2 pages.

Exhibit A—Updated—for Declaration of Robert Schiff in Support of Nevro's Reply in Support of Motion for Summary Adjudication and Opposition to BSC's Motion for Summary Judgement (Document 410), Redacted Version of ECF No. 382-10—Exhibit A to the May 9, 2018 Declaration of Robert Schiff, *Nevro Corp. vs. Boston Scientific Corporation and Boston Scientific Neuromodulation Corporation*, Case No. 3:16-cv-06830-VC-MEJ, filed May 10, 2018, 72 pages.

Declaration of Nicholas Fung in Support of Nevro's Reply in Support of Motion for Summary Adjudication and Opposition to BSC's Motion for Summary Judgement (Document 379), *Nevro Corp. vs. Boston Scientific Corporation and Boston Scientific Neuromodulation Corporation*, Case No. 3:16-cv-06830-VC-MEJ, filed May 10, 2018, 5 pages.

Exhibit 1 for Declaration of Nicholas Fung in Support of Nevro's Reply in Support of Motion for Summary Adjudication and Opposition to BSC's Motion for Summary Judgement (Document 379-1), Claims Chart, *Nevro Corp. vs. Boston Scientific Corporation and Boston Scientific Neuromodulation Corporation*, Case No. 3:16-cv-06830-VC-MEJ, filed May 10, 2018, 3 pages.

Exhibit 2 for Declaration of Nicholas Fung in Support of Nevro's Reply in Support of Motion for Summary Adjudication and Opposition to BSC's Motion for Summary Judgement (Document 379-2), Entire Document Sought to be Sealed—Document BSC-NVRO_00713169-172, *Nevro Corp. vs. Boston Scientific Corporation and Boston Scientific Neuromodulation Corporation*, Case No. 3:16-cv-06830-VC-MEJ, filed May 10, 2018, 1 page.

Exhibit 3 for Declaration of Nicholas Fung in Support of Nevro's Reply in Support of Motion for Summary Adjudication and Opposition to BSC's Motion for Summary Judgement (Document 379-3), Redacted Version of Document Sought to be Sealed—BSC's Second Supplemental Responses and Objections to Nevro's First Set of Interrogatory Request (1-8), *Nevro Corp. vs. Boston Scientific Corporation and Boston Scientific Neuromodulation Corporation*, Case No. 3:16-cv-06830-VC-MEJ, filed May 10, 2018, 13 pages.

Exhibit 4 for Declaration of Nicholas Fung in Support of Nevro's Reply in Support of Motion for Summary Adjudication and Opposition to BSC's Motion for Summary Judgement (Document 379-4), Redacted Version of Document Sought to be Sealed—Videotaped Deposition of Sridhar Kothandaraman, *Nevro Corp. vs. Boston Scientific Corporation and Boston Scientific Neuromodulation Corporation*, Case No. 3:16-cv-06830-VC-MEJ, filed May 10, 2018, 14 pages.

Exhibit 5 for Declaration of Nicholas Fung in Support of Nevro's Reply in Support of Motion for Summary Adjudication and Opposition to BSC's Motion for Summary Judgement (Document 379-5), Videotaped Deposition of Brian Erickson dated Dec. 15, 2017, *Nevro Corp. vs. Boston Scientific Corporation and Boston Scientific Neuromodulation Corporation*, Case No. 3:16-cv-06830-VC-MEJ, filed May 10, 2018, 7 pages.

Exhibit 6 for Declaration of Nicholas Fung in Support of Nevro's Reply in Support of Motion for Summary Adjudication and Opposition to BSC's Motion for Summary Judgement (Document 379-6), Plaintiff's Brief regarding Claim Construction of the "Adapted To" Claim Term, *Nevro Corp. vs. Boston Scientific Corporation and Boston Scientific Neuromodulation Corporation*, Case No. 3:16-cv-06830-VC-MEJ, filed May 10, 2018, 7 pages.

Exhibit 7 for Declaration of Nicholas Fung in Support of Nevro's Reply in Support of Motion for Summary Adjudication and Opposition to BSC's Motion for Summary Judgement (Document 379-7), Plaintiff's Response Brief regarding Claim Construction of the "Adapted To" Claim Term, *Nevro Corp. vs. Boston Scientific Corporation and Boston Scientific Neuromodulation Corporation*, Case No. 3:16-cv-06830-VC-MEJ, filed May 10, 2018, 6 pages.

Exhibit 8 for Declaration of Nicholas Fung in Support of Nevro's Reply in Support of Motion for Summary Adjudication and Opposition to BSC's Motion for Summary Judgement (Document 379-8), Deposition of Ben Pless dated Apr. 10, 2018, *Nevro Corp. vs. Boston Scientific Corporation and Boston Scientific Neuromodulation Corporation*, Case No. 3:16-cv-06830-VC-MEJ, filed May 10, 2018, 31 pages.

Exhibit 9 for Declaration of Nicholas Fung in Support of Nevro's Reply in Support of Motion for Summary Adjudication and Opposition to BSC's Motion for Summary Judgement (Document 379-9), Deposition of Dr. Gene Fridman dated Mar. 7, 2018, *Nevro Corp. vs. Boston Scientific Corporation and Boston Scientific Neuromodulation Corporation*, Case No. 3:16-cv-06830-VC-MEJ, filed May 10, 2018, 62 pages.

Exhibit 10 for Declaration of Nicholas Fung in Support of Nevro's Reply in Support of Motion for Summary Adjudication and Opposition to BSC's Motion for Summary Judgement (Document 379-10), Expert Report and Declaration of Gene Fridman, Ph.D., regarding Claim Construction, *Nevro Corp. vs. Boston Scientific Corporation and Boston Scientific Neuromodulation Corporation*, Case No. 3:16-cv-06830-VC-MEJ, filed May 10, 2018, 6 pages.

Exhibit 11 for Declaration of Nicholas Fung in Support of Nevro's Reply in Support of Motion for Summary Adjudication and Opposition to BSC's Motion for Summary Judgement (Document 379-11), Article by Tan et al., *Nevro Corp. vs. Boston Scientific Corporation and Boston Scientific Neuromodulation Corporation*, Case No. 3:16-cv-06830-VC-MEJ, filed May 10, 2018, 8 pages.

Exhibit 12 for Declaration of Nicholas Fung in Support of Nevro's Reply in Support of Motion for Summary Adjudication and Opposition to BSC's Motion for Summary Judgement (Document 379-12), Decision Denying Institution of Inter Partes Review for U.S. Pat. No. 8,359,102 (Case IPR2015-01203), *Nevro Corp. vs. Boston Scientific Corporation and Boston Scientific Neuromodulation Corporation*, Case No. 3:16-cv-06830-VC-MEJ, filed May 10, 2018, 21 pages.

Exhibit 13 for Declaration of Nicholas Fung in Support of Nevro's Reply in Support of Motion for Summary Adjudication and Opposition to BSC's Motion for Summary Judgement (Document 379-13), Certified Copy of U.S. Pat. No. 9,327,125, *Nevro Corp. vs. Boston Scientific Corporation and Boston Scientific Neuromodulation Corporation*, Case No. 3:16-cv-06830-VC-MEJ, filed May 10, 2018, 66 pages.

Exhibit 14 for Declaration of Nicholas Fung in Support of Nevro's Reply in Support of Motion for Summary Adjudication and Opposition to BSC's Motion for Summary Judgement (Document 379-14), U.S. Pat. No. 9,492,664, *Nevro Corp. vs. Boston Scientific Corporation and Boston Scientific Neuromodulation Corporation*, Case No. 3:16-cv-06830-VC-MEJ, filed May 10, 2018, 25 pages.

Exhibit 15 for Declaration of Nicholas Fung in Support of Nevro's Reply in Support of Motion for Summary Adjudication and Opposition to BSC's Motion for Summary Judgement (Document 379-15), U.S. Pat. No. 9,339,655, *Nevro Corp. vs. Boston Scientific Corporation and Boston Scientific Neuromodulation Corporation*, Case No. 3:16-cv-06830-VC-MEJ, filed May 10, 2018, 23 pages.

Exhibit 16 for Declaration of Nicholas Fung in Support of Nevro's Reply in Support of Motion for Summary Adjudication and Opposition to BSC's Motion for Summary Judgement (Document 379-16), Redacted Version of Document Sought to be Sealed—Videotaped Deposition of Richard T. Mihran, Ph.D., dated Mar. 12, 2018, *Nevro Corp. vs. Boston Scientific Corporation and Boston Scientific Neuromodulation Corporation*, Case No. 3:16-cv-06830-VC-MEJ, filed May 10, 2018, 29 pages.

Exhibit 17 for Declaration of Nicholas Fung in Support of Nevro's Reply in Support of Motion for Summary Adjudication and Opposition to BSC's Motion for Summary Judgement (Document 379-17), Redacted Version of Document Sought to be Sealed—

(56) References Cited

OTHER PUBLICATIONS

Videotaped Deposition of Jim Cassidy, dated May 17, 2017, *Nevro Corp. vs. Boston Scientific Corporation and Boston Scientific Neuromodulation Corporation,* Case No. 3:16-cv-06830-VC-MEJ, filed May 10, 2018, 13 pages.

Exhibit 18 for Declaration of Nicholas Fung in Support of Nevro's Reply in Support of Motion for Summary Adjudication and Opposition to BSC's Motion for Summary Judgement (Document 379-18), Redacted Version of Document Sought to be Sealed—Deposition of Adam Lipson, M.D., dated Apr. 12, 2018, *Nevro Corp. vs. Boston Scientific Corporation and Boston Scientific Neuromodulation Corporation,* Case No. 3:16-cv-06830-VC-MEJ, filed May 10, 2018, 10 pages.

Exhibit 19 for Declaration of Nicholas Fung in Support of Nevro's Reply in Support of Motion for Summary Adjudication and Opposition to BSC's Motion for Summary Judgement (Document 379-19), Redacted Version of Document Sought to be Sealed—BSC's Nov. 10, 17 Supplemental Responses and Objections to Nevro's Interrogatory Requests Nos. 2, 4, 5, and 7, *Nevro Corp. vs. Boston Scientific Corporation and Boston Scientific Neuromodulation Corporation,* Case No. 3:16-cv-06830-VC-MEJ, filed May 10, 2018, 9 pages.

Exhibit 20 for Declaration of Nicholas Fung in Support of Nevro's Reply in Support of Motion for Summary Adjudication and Opposition to BSC's Motion for Summary Judgement (Document 379-20), Entire Document Sought to be Sealed—Deposition of Kaoru Adair, *Nevro Corp. vs. Boston Scientific Corporation and Boston Scientific Neuromodulation Corporation,* Case No. 3:16-cv-06830-VC-MEJ, filed May 10, 2018, 1 page.

Exhibit 21—Updated—for Declaration of Nicholas Fung in Support of Nevro's Reply in Support of Motion for Summary Adjudication and Opposition to BSC's Motion for Summary Judgement (Document 471), Redacted Version of ECF No. 382-24—Videotaped Deposition of Kaoru Adair dated May 10, 2017, *Nevro Corp. vs. Boston Scientific Corporation and Boston Scientific Neuromodulation Corporation,* Case No. 3:16-cv-06830-VC-MEJ, filed May 10, 2018, 18 pages.

Exhibit 22 Declaration of Nicholas Fung in Support of Nevro's Reply in Support of Motion for Summary Adjudication and Opposition to BSC's Motion for Summary Judgement (Document 379-22), Redacted Version of Document Sought to be Sealed—Nevro Corp.'s First Amended Disclosure of Asserted Claims and Infringement Contentions, *Nevro Corp. vs. Boston Scientific Corporation and Boston Scientific Neuromodulation Corporation,* Case No. 3:16-cv-06830-VC-MEJ, filed May 10, 2018, 6 pages.

Exhibit 23 for Declaration of Nicholas Fung in Support of Nevro's Reply in Support of Motion for Summary Adjudication and Opposition to BSC's Motion for Summary Judgement (Document 379-23), Entire Document Sought to be Sealed—Document BSC-NVRO_00720938-940, *Nevro Corp. vs. Boston Scientific Corporation and Boston Scientific Neuromodulation Corporation,* Case No. 3:16-cv-06830-VC-MEJ, filed May 10, 2018, 1 page.

Exhibit 24 for Declaration of Nicholas Fung in Support of Nevro's Reply in Support of Motion for Summary Adjudication and Opposition to BSC's Motion for Summary Judgement (Document 379-24), Redacted Version of Document Sought to be Sealed—Deposition of Joshua Goshorn, dated Mar. 23, 2018, *Nevro Corp. vs. Boston Scientific Corporation and Boston Scientific Neuromodulation Corporation,* Case No. 3:16-cv-06830-VC-MEJ, filed May 10, 2018, 15 pages.

Exhibit 25 for Declaration of Nicholas Fung in Support of Nevro's Reply in Support of Motion for Summary Adjudication and Opposition to BSC's Motion for Summary Judgement (Document 379-25), Redacted Version of Document Sought to be Sealed—Videotaped Deposition of Daniel Lanovaz, dated Mar. 21, 2018, *Nevro Corp. vs. Boston Scientific Corporation and Boston Scientific Neuromodulation Corporation,* Case No. 3:16-cv-06830-VC-MEJ, filed May 10, 2018, 11 pages.

Exhibit 26 for Declaration of Nicholas Fung in Support of Nevro's Reply in Support of Motion for Summary Adjudication and Opposition to BSC's Motion for Summary Judgement (Document 379-26), Redacted Version of Document Sought to be Sealed—Rebuttal Expert Report of Richard T. Mihran, Ph.D. dated Feb. 14, 2018, *Nevro Corp. vs. Boston Scientific Corporation and Boston Scientific Neuromodulation Corporation,* Case No. 3:16-cv-06830-VC-MEJ, filed May 10, 2018, 23 pages.

Exhibit 27 for Declaration of Nicholas Fung in Support of Nevro's Reply in Support of Motion for Summary Adjudication and Opposition to BSC's Motion for Summary Judgement (Document 379-27), Expert Report of Richard T. Mihran, Ph.D., regarding Invalidity of U.S. Pat. No. 8,712,533; U.S. Pat. No. 9,327,125; U.S. Pat. No. 8,359,102; U.S. Pat. No. 9,480,842; U.S. Pat. No. 9,333,357; U.S. Pat. No. 8,792,988, and U.S. Pat. No. 8,768,472, *Nevro Corp. vs. Boston Scientific Corporation and Boston Scientific Neuromodulation Corporation,* Case No. 3:16-cv-06830-VC-MEJ, filed May 10, 2018, 6 pages.

Exhibit 28 for Declaration of Nicholas Fung in Support of Nevro's Reply in Support of Motion for Summary Adjudication and Opposition to BSC's Motion for Summary Judgement (Document 379-28), Declaration of Rafael Carbunaru in Support of Boston Scientific's Invalidity Contentions, *Nevro Corp. vs. Boston Scientific Corporation and Boston Scientific Neuromodulation Corporation,* Case No. 3:16-cv-06830-VC-MEJ, filed May 10, 2018, 13 pages.

Exhibit 29 for Declaration of Nicholas Fung in Support of Nevro's Reply in Support of Motion for Summary Adjudication and Opposition to BSC's Motion for Summary Judgement (Document 379-29), Redacted Version of Document Sought to be Sealed—Videotaped Deposition of Nevro Corp., with designated corporate representative Rafael Carbunaru, dated May 18, 2017, *Nevro Corp. vs. Boston Scientific Corporation and Boston Scientific Neuromodulation Corporation,* Case No. 3:16-cv-06830-VC-MEJ, filed May 10, 2018, 8 pages.

Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382), *Nevro Corp. vs. Boston Scientific Corporation and Boston Scientific Neuromodulation Corporation,* Case No. 3:16-cv-06830-VC-MEJ, filed May 14, 2018, 13 pages.

Exhibit A—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 468), Redacted Version of ECF No. 382-2—Nevro's Reply in Support of its Motion for Summary Adjudication and Opposition to BSC's Motion for Summary Judgment, *Nevro Corp. vs. Boston Scientific Corporation and Boston Scientific Neuromodulation Corporation,* Case No. 3:16-cv-06830-VC-MEJ, filed May 14, 2018, 40 pages.

Exhibit B for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-3), Redacted Version of Document Sought to be Filed under Seal—Expert Report of Joshua Goshorn, *Nevro Corp. vs. Boston Scientific Corporation and Boston Scientific Neuromodulation Corporation,* Case No. 3:16-cv-06830-VC-MEJ, filed May 14, 2018, 15 pages.

Exhibit C for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-5), Redacted Version of Document Sought to be Filed under Seal—Expert Report of William S. Rosenberg, M.D., FAANS, *Nevro Corp. vs. Boston Scientific Corporation and Boston Scientific Neuromodulation Corporation,* Case No. 3:16-cv-06830-VC-MEJ, filed May 14, 2018, 41 pages.

Exhibit D—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 469), Redacted Version of ECF No. 382-8—Opening Expert Report of Ben Pless regarding Infringement, dated

(56) References Cited

OTHER PUBLICATIONS

Jan. 18, 2018, *Nevro Corp. vs. Boston Scientific Corporation and Boston Scientific Neuromodulation Corporation,* Case No. 3:16-cv-06830-VC-MEJ, filed May 14, 2018, 152 pages.

Exhibit E—Updated—for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 470), Redacted Version of ECF No. 382-10—Expert Report of Robert Schiff, Ph.D., RAC, CQA, FRAPS, *Nevro Corp. vs. Boston Scientific Corporation and Boston Scientific Neuromodulation Corporation,* Case No. 3:16-cv-06830-VC-MEJ, filed May 14, 2018, 72 pages.

Exhibit F for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-11), Redacted Version of Document Sought to be Filed under Seal—Cross-Border HCP Arrangement Request, *Nevro Corp. vs. Boston Scientific Corporation and Boston Scientific Neuromodulation Corporation,* Case No. 3:16-cv-06830-VC-MEJ, filed May 14, 2018, 6 pages.

Exhibit G for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-13), Redacted Version of Document Sought to be Filed under Seal—BSC's Second Supplemental Responses and Objections to Nevro's First Set of Interrogatory Request (1-8), *Nevro Corp. vs. Boston Scientific Corporation and Boston Scientific Neuromodulation Corporation,* Case No. 3:16-cv-06830-VC-MEJ, filed May 14, 2018, 14 pages.

Exhibit H for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-15), Redacted Version of Document Sought to be Filed under Seal—Videotaped Deposition of Sridhar Kothandaraman, dated Nov. 17, 2017, *Nevro Corp. vs. Boston Scientific Corporation and Boston Scientific Neuromodulation Corporation,* Case No. 3:16-cv-06830-VC-MEJ, filed May 14, 2018, 15 pages.

Exhibit I for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-17), Redacted Version of Document Sought to be Filed under Seal—Videotaped Deposition of Richard T. Mihran, dated Mar. 12, 2018, *Nevro Corp. vs. Boston Scientific Corporation and Boston Scientific Neuromodulation Corporation,* Case No. 3:16-cv-06830-VC-MEJ, filed May 14, 2018, 30 pages.

Exhibit J for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-19), Redacted Version of Document Sought to be Filed under Seal—BSC's Nov. 10, 2017 Supplemental Responses and Objections to Nevro's Interrogatory Requests Nos. 2, 4, 5, and 7, *Nevro Corp. vs. Boston Scientific Corporation and Boston Scientific Neuromodulation Corporation,* Case No. 3:16-cv-06830-VC-MEJ, filed May 14, 2018, 10 pages.

Exhibit K for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-21), Redacted Version of Document Sought to be Filed under Seal—Dec. 14, 2016 Correspondence between Boston Scientific and U.S. Food and Drug Administration, *Nevro Corp. vs. Boston Scientific Corporation and Boston Scientific Neuromodulation Corporation,* Case No. 3:16-cv-06830-VC-MEJ, filed May 14, 2018, 23 pages.

Exhibit L—Updated for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 471), Updated Redacted Version of ECF No. 382-24—Videotaped Deposition of Kaoru Lee Adair, dated May 10, 2017, *Nevro Corp. vs. Boston Scientific Corporation and Boston Scientific Neuromodulation Corporation,* Case No. 3:16-cv-06830-VC-MEJ, filed May 14, 2018, 18 pages.

Exhibit M for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-25), Redacted Version of Document Sought to be Filed under Seal—Nevro Corp.'s First Amended Disclosure of Asserted Claims and Infringement Contentions, *Nevro Corp. vs. Boston Scientific Corporation and Boston Scientific Neuromodulation Corporation,* Case No. 3:16-cv-06830-VC-MEJ, filed May 14, 2018, 7 pages.

Exhibit N for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-27), Redacted Version of Document Sought to be Filed under Seal—Feb. 2016 Email regarding Precision 10K Training Follow-up, *Nevro Corp. vs. Boston Scientific Corporation and Boston Scientific Neuromodulation Corporation,* Case No. 3:16-cv-06830-VC-MEJ, filed May 14, 2018, 5 pages.

Exhibit O for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-29), Redacted Version of Document Sought to be Filed under Seal—Deposition of Joshua Goshorn dated Mar. 23, 2018, *Nevro Corp. vs. Boston Scientific Corporation and Boston Scientific Neuromodulation Corporation,* Case No. 3:16-cv-06830-VC-MEJ, filed May 14, 2018, 16 pages.

Exhibit P for Declaration of Carson D. Anderson in Support of Nevro's Administrative Motion to File under Seal Portions of Nevro's Reply in Support of It's Motion for Summary Adjudication and Opposition to BSC's Motion for Summary Judgement (Document 382-31), Redacted Version of Document Sought to be Filed under Seal—Videotaped Deposition of Daniel Lanovaz dated Mar. 21, 2018, *Nevro Corp. vs. Boston Scientific Corporation and Boston Scientific Neuromodulation Corporation,* Case No. 3:16-cv-06830-VC-MEJ, filed May 14, 2018, 12 pages.

[Proposed] Order Granting Administrative Motion to File under Seal Portions of Nevro's Reply in Support of It's Motion for Summary Adjudication and Opposition to BSC's Motion for Summary Judgement and Supporing Documents (Document 382-33), *Nevro Corp. vs. Boston Scientific Corporation and Boston Scientific Neuromodulation Corporation,* Case No. 3:16-cv-06830-VC-MEJ, filed May 14, 2018, 7 pages.

Updated Boston Scientific's Reply in Support of Motion for Summary Judgement (Document 473), Updated Redacted Version of ECF No. 397-3, *Nevro Corp. vs. Boston Scientific Corporation and Boston Scientific Neuromodulation Corporation,* Case No. 3:16-cv-06830-VC-MEJ, filed Jul. 30, 2018, 27 pages.

Declaration of Carson D. Anderson in Support of Boston Scientific's Reply in Support of Motion for Summary Judgement (Document 398-1), Redacted Version of Document Sought to be Filed under Seal—Cross-Border HCP Arrangement Request, *Nevro Corp. vs. Boston Scientific Corporation and Boston Scientific Neuromodulation Corporation,* Case No. 3:16-cv-06830-VC-MEJ, filed May 24, 2018, 3 pages.

Exhibit 1 for Declaration of Carson D. Anderson in Support of Boston Scientific's Reply in Support of Motion for Summary Judgement (Document 398-2), Redacted Version of Document Sought to be Filed under Seal—May 2004 Email regarding Post-Market Studies for AB SCS System, *Nevro Corp. vs. Boston Scientific Corporation and Boston Scientific Neuromodulation Corporation,* Case No. 3:16-cv-06830-VC-MEJ, filed May 24, 2018, 5 pages.

(56) References Cited

OTHER PUBLICATIONS

Exhibit 2 for Declaration of Carson D. Anderson in Support of Boston Scientific's Reply in Support of Motion for Summary Judgement (Document 398-3), Redacted Version of Document Sought to be Filed under Seal—Corrected Rebuttal Expert Report of Ben Pless regarding Validity, dated Mar. 5, 2018, *Nevro Corp.* vs. *Boston Scientific Corporation and Boston Scientific Neuromodulation Corporation*, Case No. 3:16-cv-06830-VC-MEJ, filed May 24, 2018, 4 pages.

Exhibit 3 for Declaration of Carson D. Anderson in Support of Boston Scientific's Reply in Support of Motion for Summary Judgement (Document 398-4), U.S. Pat. No. 7,389,145 by Kilgore et al., *Nevro Corp.* vs. *Boston Scientific Corporation and Boston Scientific Neuromodulation Corporation*, Case No. 3:16-cv-06830-VC-MEJ, filed May 24, 2018, 12 pages.

Exhibit 4 for Declaration of Carson D. Anderson in Support of Boston Scientific's Reply in Support of Motion for Summary Judgement (Document 398-5), Redacted Version of Document Sought to be Filed under Seal—Videotaped Deposition of Robert Schiff, dated Mar. 15, 2018, *Nevro Corp.* vs. *Boston Scientific Corporation and Boston Scientific Neuromodulation Corporation*, Case No. 3:16-cv-06830-VC-MEJ, filed May 24, 2018, 19 pages.

Exhibit 5 for Declaration of Carson D. Anderson in Support of Boston Scientific's Reply in Support of Motion for Summary Judgement (Document 398-6), Filed under Seal—Document NEVRO_BSXCA0093092-109, *Nevro Corp.* vs. *Boston Scientific Corporation and Boston Scientific Neuromodulation Corporation*, Case No. 3:16-cv-06830-VC-MEJ, filed May 24, 2018, 1 page.

Exhibit 6 for Declaration of Carson D. Anderson in Support of Boston Scientific's Reply in Support of Motion for Summary Judgement (Document 398-7), Filed under Seal—Document NEVRO_BSXCA0067869-75, *Nevro Corp.* vs. *Boston Scientific Corporation and Boston Scientific Neuromodulation Corporation*, Case No. 3:16-cv-06830-VC-MEJ, filed May 24, 2018, 1 page.

Exhibit 7 for Declaration of Carson D. Anderson in Support of Boston Scientific's Reply in Support of Motion for Summary Judgement (Document 398-8), Filed under Seal—Document NEVRO_BSXCA0147580-86, *Nevro Corp.* vs. *Boston Scientific Corporation and Boston Scientific Neuromodulation Corporation*, Case No. 3:16-cv-06830-VC-MEJ, filed May 24, 2018, 1 page.

Exhibit 8 for Declaration of Carson D. Anderson in Support of Boston Scientific's Reply in Support of Motion for Summary Judgement (Document 398-9), Filed under Seal—Opening Expert Report of Ben Pless regarding Infringement, dated Jan. 18, 2018, *Nevro Corp.* vs. *Boston Scientific Corporation and Boston Scientific Neuromodulation Corporation*, Case No. 3:16-cv-06830-VC-MEJ, filed May 24, 2018, 7 pages.

Exhibit 9 for Declaration of Carson D. Anderson in Support of Boston Scientific's Reply in Support of Motion for Summary Judgement (Document 398-10), Filed under Seal—Expert Report of W. Todd Schoettelkotte Relating to Damages, dated Jan. 18, 2018, *Nevro Corp.* vs. *Boston Scientific Corporation and Boston Scientific Neuromodulation Corporation*, Case No. 3:16-cv-06830-VC-MEJ, filed May 24, 2018, 1 page.

Exhibit 10 for Declaration of Carson D. Anderson in Support of Boston Scientific's Reply in Support of Motion for Summary Judgement (Document 398-11), Redacted Version of Document Sought to be Filed under Seal—Design Change Analysis Form (DCAF), *Nevro Corp.* vs. *Boston Scientific Corporation and Boston Scientific Neuromodulation Corporation*, Case No. 3:16-cv-06830-VC-MEJ, filed May 24, 2018, 2 pages.

Exhibit 11 for Declaration of Carson D. Anderson in Support of Boston Scientific's Reply in Support of Motion for Summary Judgement (Document 398-12), Redacted Version of Document Sought to be Filed under Seal—Videotaped Deposition of Rafael Carbunaru, Ph.D., dated Nov. 14, 2017, *Nevro Corp.* vs. *Boston Scientific Corporation and Boston Scientific Neuromodulation Corporation*, Case No. 3:16-cv-06830-VC-MEJ, filed May 24, 2018, 9 pages.

Exhibit 12 for Declaration of Carson D. Anderson in Support of Boston Scientific's Reply in Support of Motion for Summary Judgement (Document 398-13), Declaration of James Thacker under 37 CFR 1.1.32, dated Jun. 6, 2013, *Nevro Corp.* vs. *Boston Scientific Corporation and Boston Scientific Neuromodulation Corporation*, Case No. 3:16-cv-06830-VC-MEJ, filed May 24, 2018, 9 pages.

Exhibit 13 for Declaration of Carson D. Anderson in Support of Boston Scientific's Reply in Support of Motion for Summary Judgement (Document 398-14), Information Disclosure Statement SB-08 Form for U.S. Appl. No. 14/525,134, *Nevro Corp.* vs. *Boston Scientific Corporation and Boston Scientific Neuromodulation Corporation*, Case No. 3:16-cv-06830-VC-MEJ, filed May 24, 2018, 13 pages.

Exhibit 14 for Declaration of Carson D. Anderson in Support of Boston Scientific's Reply in Support of Motion for Summary Judgement (Document 398-15), Amendment in Response to Final Office Action for U.S. Appl. No. 12/765,685, filed Sep. 19, 2013, *Nevro Corp.* vs. *Boston Scientific Corporation and Boston Scientific Neuromodulation Corporation*, Case No. 3:16-cv-06830-VC-MEJ, filed May 24, 2018, 15 pages.

Exhibit 15 for Declaration of Carson D. Anderson in Support of Boston Scientific's Reply in Support of Motion for Summary Judgement (Document 398-16), Amendment in Response to Non-Final Office Action for U.S. Appl. No. 13/830,992, filed Feb. 24, 2014, *Nevro Corp.* vs. *Boston Scientific Corporation and Boston Scientific Neuromodulation Corporation*, Case No. 3:16-cv-06830-VC-MEJ, filed May 24, 2018, 15 pages.

Exhibit 16 for Declaration of Carson D. Anderson in Support of Boston Scientific's Reply in Support of Motion for Summary Judgement (Document 398-17), Amendment in Response to Final Office Action for U.S. Appl. No. 14/292,671, filed Jan. 17, 2017, *Nevro Corp.* vs. *Boston Scientific Corporation and Boston Scientific Neuromodulation Corporation*, Case No. 3:16-cv-06830-VC-MEJ, filed May 24, 2018, 12 pages.

Declaration of J. Lawrence Stevens in Support of Boston Scientific's Reply in Support of Motion for Summary Judgement (Document 398-18), *Nevro Corp.* vs. *Boston Scientific Corporation and Boston Scientific Neuromodulation Corporation*, Case No. 3:16-cv-06830-VC-MEJ, filed May 24, 2018, 34 pages.

Boston Scientific's Response to the Summons to Attend Oral Proceedings for European Patent No. 2207587 *Nevro Corp.* vs. *Boston Scientific Neuromodulation Corporation*, filed Sep. 6, 2018, 31 pages.

Boston Scientific's Responsive Claim Construction Brief, Opposition to in Nevro's Motion for Summary Judgment and Opening Motion for Summary Judgment (Document 358), *Nevro Corp.* vs. *Boston Scientific Corporation and Boston Scientific Neuromodulation Corporation*, Case No. 3:16-cv-06830-VC-MEJ, filed Apr. 26, 2018, 60 pages.

Declaration of Rafael Carbunaru in Support of Boston Scientific Administrative Motion to File under Seal Portions of Boston Scientific's Opposition to Nevro's Motion to Strike BSC's Undisclosed Invalidity Theories (Dkt No. 340) and Supporting Documents (Document 355-2), *Nevro Corp.* vs. *Boston Scientific Corporation and Boston Scientific Neuromodulation Corporation*, Case No. 3:16-cv-06830-VC-MEJ, filed Apr. 26, 2018, 3 pages.

Declaration of Sridhar Kothandaraman (Document 356-1), *Nevro Corp.* vs. *Boston Scientific Corporation and Boston Scientific Neuromodulation Corporation*, Case No. 3:16-cv-06830-VC-MEJ, filed Apr. 26, 2018, 4 pages Exhibit B to the Declaration of Clara W. Wang in Support of Nevro's Administrative Motion to File under Seal Portions of Nevro's Reply to Strike BSC's Invalidity Positions and Supporting Documents (Dkt No. 366) (Document 368-4), *Nevro Corp.* vs. *Boston Scientific Corporation and Boston Scientific Neuromodulation Corporation*, Case No. 3:16-cv-06830-VC-MEJ, filed May 7, 2018, 10 pages.

Order Re: Claim Construction and Cross-Motions for Summary Judgement (Document 449), *Nevro Corp.* vs. *Boston Scientific Corporation and Boston Scientific Neuromodulation Corporation*, Case No. 3:16-cv-06830-VC-MEJ, filed Jul. 24, 2018, 9 pages.

(56) References Cited

OTHER PUBLICATIONS

Tentative Ruling (Document 422), *Nevro Corp. vs. Boston Scientific Corporation and Boston Scientific Neuromodulation Corporation,* Case No. 3:16-cv-06830-VC-MEJ, filed Jul. 5, 2018, 3 pages.
Nevro Written Submissions for European Patent No. 2207587, Opponents: Medtronic Inc., and Boston Scientific Neuromodulation Corporation, mailed Jul. 24, 2018, 9 pages.
Notice of Opposition for European Patent No. 3156099, Proprietor of the Patent: Nevro Corporation; Opponent: Boston Scientific Neuromodulation Corporation, Dec. 15, 2017, 27 pages.
Thomson et al., "Effects of Rate on Analgesia in Kilohertz Frequency Spinal Cord Stimulation: Results of the PROCO Randomized Controlled Trial," Neuromodulation: Technology at the Neural Interface, 2017, 10 pages.
Brief for Plaintiff-Appellant Nevro Corp., *Nevro Corp. vs. Boston Scientific Corporation and Boston Scientific Neuromodulation Corporation,* Case No. 3:16-cv-06830-VC-MEJ, filed Nov. 8, 2018, 341 pages.
Medtronic's Response to the Summons to Attend Oral Proceedings for European Patent No. 2853285, *Nevro Corp. vs. Boston Scientific Neuromodulation Corporation and Medtronic, Inc.,* filed Nov. 30, 2018, 8 pages.
Boston Scientific's Response to the Summons to Attend Oral Proceedings for European Patent No. 2853285, *Nevro Corp. vs. Boston Scientific Neuromodulation Corporation and Medtronic, Inc.,* filed Nov. 30, 2018, 5 pages.
Decision Rejecting the Opposition (Art. 101(2) EPC) for European Patent No. 2207587, *Nevro Corp. vs. Boston Scientific Neuromodulation Corporation and Medtronic, Inc.,* Jan. 4, 2019, 18 pages.
Provision of a Copy of Minutes in accordance with Rule 124(4) EPC for Opposition by Medtronic, Inc., and Boston Scientific Neuromodulation Corporation for European Patent No. 2207587, mailed Jan. 4, 2019, 10 pages.
Medtronic's Submissions Commenting on the Auxiliary Requests for European Patent No. 2853285, *Nevro Corp. vs. Boston Scientific Neuromodulation Corporation and Medtronic, Inc.,* filed Jan. 11, 2019, 13 pages.
Decision Revoking for European Patent (Art. 101(2) and 101(3)(b) EPC) for European Patent No. 2853285, *Nevro Corp. vs. Boston Scientific Neuromodulation Corporation and Medtronic, Inc.,* mailed Apr. 1, 2019, 54 pages.
Patentee: Nevro Corporation reply to Notice of Opposition filed by Boston Science Neuromodulation on Jul. 27, 2018 and Medtronic, Inc., on Mar. 3, 2019 for European Patent No. 3156099, mailed Aug. 7, 2019, 104 pages.
Patentee: Nevro Corporation reply to Statement Grounds of Appeal in Support to the Notice of Appeal on May 17, 2019 for European Patent No. 2853285, mailed Aug. 9, 2019, 24 pages.
Patentee: Nevro Corporation reply to Summons to Oral Proceedings for European Patent No. 2853285, mailed Nov. 30, 2018, 6 pages.
Provision of a Copy of the Minutes in accordance with Rule 124(4) EPC, *Nevro Corp. vs. Boston Scientific Neuromodulation Corporation and Medtronic, Inc.,* for European Patent No. 2853285, mailed Apr. 1, 2019, 10 pages.
Non-Confidential Opening Brief of Appellant Stimwave Technologies, Inc. for Plaintiff-Appellee: Nevro Corp vs. Defendant-Appellant: Stimwave Technologies, Inc., United States Court of Appeals for Federal Circuit, Case 19-CV-325, filed Sep. 24, 2019, 156 pages.
Principal and Response Brief for Defendants-Cross-Appellants Boston Scientific Corporation's and Boston Scientific Neuromodulation Corporation's, *Nevro Corp. v. Boston Scientific Corporation and Boston Scientific Neuromodulation Corporation,* Case No. 3:16-cv-06830-VC (N.D. Cal.), Jan. 17, 2019, 71 pages.
Reply Brief for Defendants-Cross-Appellants Boston Scientific Corporation's and Boston Scientific Neuromodulation Corporation's, *Nevro Corp. v. Boston Scientific Corporation and Boston Scientific Neuromodulation Corporation,* Case No. 3:16-cv-06830-VC (N.D. Cal.), Jun. 3, 2019, 26 pages.

Response and Reply Brief for Plaintiff-Appellant Nevro Corp., *Nevro Corp. v. Boston Scientific Corporation and Boston Scientific Neuromodulation Corporation,* Case No. 3:16-cv-06830-VC (N.D. Cal.), Apr. 12, 2019, 68 pages.
Memorandum Opinion, Plaintiff: Nevro Corp. vs. Defendant-Appellant: Stimwave Technologies, Inc., United States Court for the District of Delaware, Civil Action No. 19-325-CFC, Case 19-CV-325, filed Jul. 24, 2019, 46 pages.
Medtronic—Spinal Cord Stimulation (SCS) Patient Management Guidelines for Clinicians, 1999, 114 pages.
Nevro—Leadership Through Innovation, J. P. Morgan 37th Annual Healthcare Conference, Jan. 24, 2019, 2 pages.
Notice of Opposition for European Patent No. 3156099, Proprietor of the Patent: Nevro Corporation; Opponent: Medtronic, Inc., Mar. 11, 2019, 31 pages.
Opponent Response to Patent Proprietor Comments to Declaration of Dr. Baranidharan for European Patent No. 2630984, mailed Nov. 8, 2016, 3 pages.
Opponents Boston Scientific Neuromodulation Corporation.: Statement Setting Out the Grounds of Appeal for European Patent No. 2207587, mailed May 2, 2019, 12 pages.
Opponents Medtronic, Inc.: Response to Grounds of Appeal for European Patent No. 2630984, mailed Dec. 19, 2017, 23 pages.
Opponents Medtronic, Inc.: Statement Setting Out the Grounds of Appeal for European Patent No. 2207587, mailed May 19, 2019, 21 pages.
Reply of the Patent Proprietor, Nevro Corporation for European Patent No. 2207587, Opponent 1: Medtronic, Inc., and Opponent 2: Boston Scientific Neuromodulation Corporation, mailed Sep. 25, 2019.
Summons to Attend Oral Proceedings pursuant to Rule 115(1) EPC for European Patent No. 3156099, Applicant: Nevro Corporation, mailed Nov. 22, 2019, 21 pages.
Al-Kaisy et al., "The Use of 10-Kilohertz Spinal Cord Stimulation in Cohort of Patients with Chronic Neuropathic Limb Pain Refractory to Medical Management," Neuromodulation: Technology at the Neural Interface, Feb. 2014, 7 pages.
Tesfaye et al., "Electrical Spinal-Cord Stimulation for Painful Diabetic Peripheral Neuropathy," The Lancet, vol. 348, Dec. 1996, 4 pages.
Van Beek et al., "Spinal Cord Stimulation in Experimental Chronic Painful Diabetic Polyneuropathy: Delayed Effect of High-Frequency Stimulation," European Journal of Pain, Oct. 2016, 9 pages.
Seattle Pain Relief Now Helping Diabetic Neuropathy Patients Restore Sensation with Spinal Cord Stimulation, PRWeb Online Visibility from Vocus, https://www.prweb.com/releases/diabetic-neuopathy/seattle-tacoma-wa/prweb13080906.htm, 2015, 2 pages.
Ahmed et al., "Effects of Spinal Cord Stimulation on Pain Thresholds and Sensory Perceptions in Chronic Pain Patients," Neuromodulation. 2015;18(5):6 pages.
Daousi C et al., "Electrical spinal cord stimulation in the long-term treatment of chronic painful diabetic neuropathy" Diabet Med. 2005;22(4):6 pages.
De Vos et al., "Burst spinal cord stimulation evaluated in patients with failed back surgery syndrome and painful diabetic neuropathy" Neuromodulation. 2014;17(2): 8 pages.
De Vos et al., Effect and safety of spinal cord stimulation for treatment of chronic pain caused by diabetic neuropathy. J Diabetes Complications. 2009;23(1): 6 pages.
De Vos et al., "Spinal cord stimulation in patients with painful diabetic neuropathy: a multicenter randomized clinical trial," Pain. 2014;155(11):.6 pages.
Duarte et al., "Quality of life increases in patients with painful diabetic neuropathy following treatment with spinal cord stimulation" Qual Life Res. 2016;25(7):7 pages.
Eisenberg et al., "Quantitative Sensory Testing for Spinal Cord Stimulation in Patients With Chronic Neuropathic Pain. Pain Practice" 2006;6(3):5 pages.
Eldabe et al. "Retrospective Case Series on the Treatment of Painful Diabetic Peripheral Neuropathy With Dorsal Root Ganglion Stimulation." Neuromodulation. 2018;21(8): 6 pages.

(56) References Cited

OTHER PUBLICATIONS

Koetsier et al., "Effectiveness of dorsal root ganglion stimulation and dorsal col. spinal cord stimulation in a model of experimental painful diabetic polyneuropathy," CNS Neurosci Ther. 2019;25(3): 8 pages.

Koetsier et al., "Mechanism of dorsal root ganglion stimulation for pain relief in painful diabetic polyneuropathy is not dependent on GABA release in the dorsal horn of the spinal cord" CNS Neurosci Ther. 2020;26(1): 8 pages.

Kumar et al., "Spinal cord stimulation for chronic pain in peripheral neuropathy" Surg Neurol. 1996;46(4):7 pages.

Pluijms et al. "Increased contact heat evoked potential stimulation latencies in responders to spinal cord stimulation for painful diabetic polyneuropathy," Neuromodulation. 2015;18(2) 7 pages.

Pluijms et al., "Pain relief and quality-of-life improvement after spinal cord stimulation in painful diabetic polyneuropathy: a pilot study" British Journal of Anaesthesia. 2012;109(4):7 pages.

Pluijms et al., "The effect of spinal cord stimulation frequency in experimental painful diabetic polyneuropathy" Eur J Pain. 2013;17(9):9 pages.

Slangen et al., "Spinal cord stimulation and pain relief in painful diabetic peripheral neuropathy: a prospective two-center randomized controlled trial" Diabetes Care. 2014;37(11): 9 pages.

Van Beek et al. "Sustained Treatment Effect of Spinal Cord Stimulation in Painful Diabetic Peripheral Neuropathy: 24-Month Follow-up of a Prospective Two-Center Randomized Controlled Trial. Diabetes Care" 2015;38(9):3 pages.

Van Beek et al., "Long-Term Spinal Cord Stimulation Alleviates Mechanical Hypersensitivity and Increases Peripheral Cutaneous Blood Perfusion in Experimental Painful Diabetic Polyneuropathy" Neuromodulation. 2018;21(5):8 pages.

Van Beek et al., "Severity of Neuropathy Is Associated With Long-term Spinal Cord Stimulation Outcome in Painful Diabetic Peripheral Neuropathy: Five-Year Follow-up of a Prospective Two-Center Clinical Trial" Diabetes Care. 2018;41(1): 7 pages.

Slangen et al., "Sustained effect of spinal cord" stimulation on pain and quality of life in painful diabetic peripheral neuropathy British Journal of Anaesthesia, 2013;111(6):1030-1031, 2 pages.

\* cited by examiner

| Effects of the Autonomic System on Body Organs ||||
|---|---|---|---|
| Effector organs | | Effects of sympathetic stimulation | Effects of parasympathetic stimulation |
| Adipose tissue | | (β) Lipolysis | |
| Adrenal medulla | | | Secretion of epinephrine and norepinephrine |
| Blood vessels | Coronary | (α) Constriction | Dilation |
| | | (β) Dilation | |
| | Cutaneous | (α) Constriction | |
| | | (ACh) Dilation | |
| | Skeletal muscle | (α) Constriction | |
| | | (β) Dilation | |
| | | (ACh) Dilation | |
| | Abdominal visceral | (α) Constriction | |
| | | (β) Dilation | |
| | Renal | (α) Constriction | |
| | Salivary glands | (α) Constriction | Dilation |
| Eye | Radial muscle of the iris | (α) Contraction (mydriasis) | |
| | Sphincter muscle of the iris | | Contraction (myosis) |
| | Ciliary muscle of the lens | (β) Relaxation Lens flattens | Contraction (Lens curves) |
| Gallbladder and ducts | | Relaxation | Contraction |
| Heart | SA node | (β) ↑ heart rate | ↓ heart rate |
| | Atria | (β) ↑ heart rate and force | ↓ heart force |
| | AV node | (β) ↑ conduction velocity | ↓ conduction velocity |
| | Purkinje system | (β) ↑ heart rate and force | |
| | Ventricles | (β) ↑ heart rate and force | |
| Intestine | Motility and tone | (α,β) Decrease | Increase |
| | Sphincters | (α) Contraction (usually) | Relaxation (usually) |
| | Secretion | Inhibition (?) | Stimulation |
| Juxtaglomerular cells | | (β) Renin secretion | |
| Lacrimal glands | | | Secretion |
| Liver | | (β) Glycogenolysis | |
| Lung (bronchial muscles) | | (β) Relaxation | Contraction |
| Male sex organs | | Ejaculation | Erection |
| Nasopharyngeal glands | | | Secretion |
| Pancreas | Acinar cells | ↓ secretion | Secretion |
| | Islet cells | (α) Inhibition of insulin and glucagon secretion | Insulin and glucagon secretion |
| | | (β) Insulin and glucagon secretion | |
| Pineal gland | | (β) Melatonin synthesis and secretion | |
| Salivary glands | | (α) Thick, sparse secretion | Profuse, watery secretion |
| Skin | Pilomotor muscles | (α) Contraction | |
| | Sweat glands | (α) Slight, localized secretion | |
| | | (ACh) Generalized secretions | |
| Spleen capsule | | (α) Contraction | |
| Stomach | Motility and tone | (β) Decrease (usually) | Increase |
| | Sphincters | (α) Contraction (usually) | Relaxation (usually) |
| | Secretion | Inhibition (?) | Stimulation |
| Ureter | Motility and tone | Increase (usually) | Increase (?) |
| Urinary bladder | Detrusor | (β) Relaxation (usually) | Contraction |
| | Trigone and sphincter | (α) Contraction | Relaxation |

(Source: www.neurophysiology.ws)

*FIG. 8*

AUTONOMIC NERVOUS SYSTEM CONTROL VIA HIGH FREQUENCY SPINAL CORD MODULATION, AND ASSOCIATED SYSTEMS AND METHODS

CROSS-REFERENCE TO RELATED APPLICATION

The present application is a continuation of U.S. patent application Ser. No. 16/406,982, now issued as U.S. Pat. No. 11,247,057, filed May 8, 2019 which is a continuation of U.S. patent application Ser. No. 15/808,891, now issued as U.S. Pat. No. 10,328,256, filed Nov. 9, 2017, which is a continuation of U.S. patent application Ser. No. 13/922,765, now issued as U.S. Pat. No. 9,833,614, filed Jun. 20, 2013, which claims priority to pending U.S. Provisional Application No. 61/663,466, filed on Jun. 22, 2012, and are incorporated herein by reference. To the extent the foregoing application and/or any other materials incorporated herein by reference conflict with the present disclosure, the present disclosure controls.

TECHNICAL FIELD

The present technology is directed generally to autonomic nervous system control obtained via high frequency spinal cord modulation, and associated systems and methods.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings spaced apart from each other at the distal end of the lead body. The conductive rings operate as individual electrodes and, in many cases, the SCS leads are implanted percutaneously through a large needle inserted into the epidural space, with or without the assistance of a stylet.

While the foregoing stimulators and techniques have proven beneficial in many instances, there remains a significant need in the medical community for improved devices and therapies that can address a broad range of patient indications.

BRIEF DESCRIPTION OF THE DRAWINGS

FIG. 8 is a table illustrating representative effects of the autonomic nervous system on representative organs.

DETAILED DESCRIPTION

1.0 Introduction

Figure 1A:
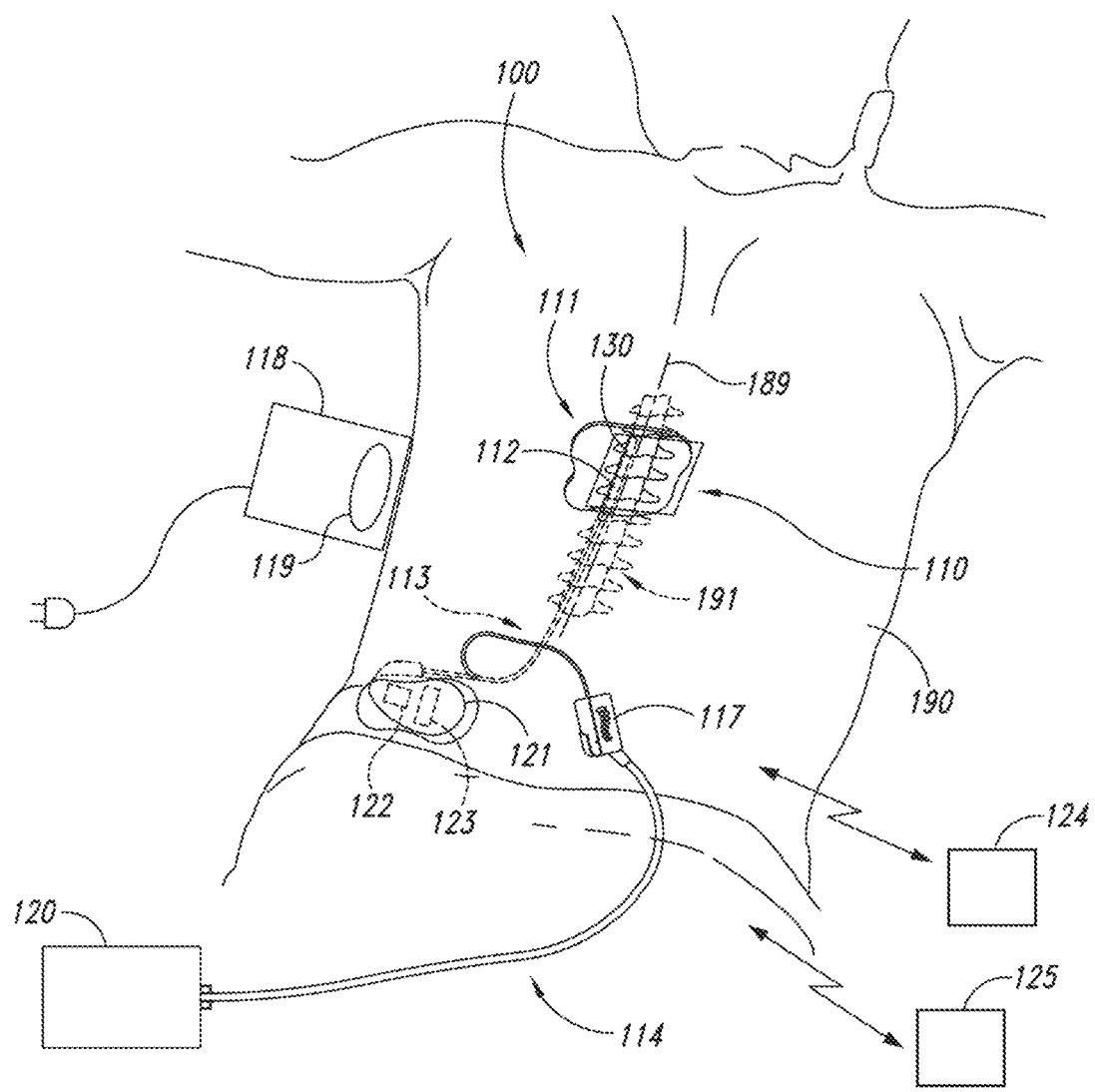
FIG. 1A is a partially schematic illustration of an implantable spinal cord modulation system positioned at the spine to deliver therapeutic signals in accordance with several embodiments of the present disclosure.

The present technology is directed generally to spinal cord modulation and associated systems and methods for controlling the autonomic nervous system and/or otherwise affecting the autonomic nervous system (ANS) via waveforms with high frequency elements or components (e.g., portions having high fundamental frequencies). These frequencies have also been demonstrated to provide pain relief generally with reduced or eliminated side effects. Such side effects can include unwanted motor stimulation or blocking, and/or interference with sensory functions other than the targeted pain, and/or patient proprioception. Several embodiments continue to provide pain relief for at least some period of time after the spinal cord modulation signals have ceased. Specific details of certain embodiments of the disclosure are described below with reference to methods for modulating one or more target neural populations (e.g., nerves) or sites of a patient, and associated implantable structures for providing the modulation. The following sections also describe physiological mechanisms by which it is expected that methods in accordance with certain embodiments achieve the observed results. Some embodiments can have configurations, components or procedures different than those described in this section, and other embodiments may eliminate particular components or procedures. A person of ordinary skill in the relevant art, therefore, will understand that the disclosure may include other embodiments with additional elements, and/or may include other embodiments without several of the features shown and described below with reference to FIGS. 1A-8.

In general terms, aspects of many of the following embodiments are directed to producing a therapeutic effect that includes pain reduction and/or ANS control in the patient. The therapeutic effect can be produced by inhibiting, suppressing, downregulating, blocking, preventing, or otherwise modulating the activity of the affected neural population. In many embodiments of the presently disclosed techniques, therapy-induced paresthesia is not a prerequisite to achieving pain reduction, unlike standard SCS techniques. It is also expected that the techniques described below with reference to FIGS. 1A-8 can produce longer lasting results than can existing spinal cord stimulation therapies. In particular, these techniques can produce results that persist after the modulation signal ceases. Accordingly, these techniques can use less power than existing techniques because they need not require delivering modulation signals continuously to obtain a beneficial effect.

In particular embodiments, therapeutic modulation signals are directed generally to the patient's spinal cord, e.g., the dorsal column of the patient's spinal cord. In other embodiments, the modulation signals can be directed to other neural populations, including but not limited to the dorsal horn, dorsal root, dorsal root ganglion, dorsal root entry zone, and/or other particular areas at or in close proximity to the spinal cord itself. The foregoing areas are referred to herein collectively as the spinal cord region. In still further embodiments, the modulation signals may be directed to other neurological structures and/or target neural populations.

Several aspects of the technology are embodied in computing devices, e.g., programmed/programmable pulse generators, controllers and/or other devices. The computing devices on which the described technology can be implemented may include one or more central processing units, memory, input devices (e.g., input ports), output devices (e.g., display devices), storage devices, and network devices (e.g., network interfaces). The memory and storage devices are computer-readable media that may store instructions that implement the technology. In many embodiments, the computer readable media are tangible media. In other embodiments, the data structures and message structures may be stored or transmitted via an intangible data transmission medium, such as a signal on a communications link. Various suitable communications links may be used, including but not limited to a local area network and/or a wide-area network.

2.0 Overall System Characteristics

FIG. 1A schematically illustrates a representative patient system 100 for providing relief from chronic pain and/or other conditions, and/or affect the ANS, arranged relative to the general anatomy of a patient's spinal cord 191. The overall patient system 100 can include a signal delivery system 110, which may be implanted within a patient 190, typically at or near the patient's midline 189, and coupled to a pulse generator 121. The signal delivery system 110 can provide therapeutic electrical signals to the patient during operation. In a representative example, the signal delivery system 110 includes a signal delivery device 111 that carries features for delivering therapy to the patient 190 after implantation. The pulse generator 121 can be connected directly to the signal delivery device 111, or it can be coupled to the signal delivery device 111 via a signal link 113 (e.g., an extension). In a further representative embodiment, the signal delivery device 111 can include an elongated lead or lead body 112. As used herein, the terms "lead" and "lead body" include any of a number of suitable substrates and/or support members that carry devices for providing therapy signals to the patient 190. For example, the lead 112 can include one or more electrodes or electrical contacts that direct electrical signals into the patient's tissue, such as to provide for patient relief. In other embodiments, the signal delivery device 111 can include structures other than a lead body (e.g., a paddle) that also direct electrical signals and/or other types of signals to the patient 190.

The pulse generator 121 can transmit signals (e.g., electrical signals) to the signal delivery device 111 that up-regulate (e.g., stimulate or excite) and/or down-regulate (e.g., block or suppress) target nerves. As used herein, and unless otherwise noted, the terms "modulate" and "modulation" refer generally to signals that have either type of the foregoing effects on the target nerves. The pulse generator 121 can include a machine-readable (e.g., computer-readable) medium containing instructions for generating and transmitting suitable therapy signals. The pulse generator 121 and/or other elements of the system 100 can include one or more processors 122, memories 123 and/or input/output devices. Accordingly, the process of providing modulation signals, providing guidance information for locating the signal delivery device 111, and/or executing other associated functions can be performed by computer-executable instructions contained by computer-readable media located at the pulse generator 121 and/or other system components. The pulse generator 121 can include multiple portions, elements, and/or subsystems (e.g., for directing signals in accordance with multiple signal delivery parameters), carried in a single housing, as shown in FIG. 1A, or in multiple housings.

In some embodiments, the pulse generator 121 can obtain power to generate the therapy signals from an external power source 118. The external power source 118 can transmit power to the implanted pulse generator 121 using electromagnetic induction (e.g., RF signals). For example, the external power source 118 can include an external coil 119 that communicates with a corresponding internal coil (not shown) within the implantable pulse generator 121. The external power source 118 can be portable for ease of use.

During at least some procedures, an external programmer 120 (e.g., a trial modulator) can be coupled to the signal delivery device 111 during an initial procedure, prior to implanting the pulse generator 121. For example, a practitioner (e.g., a physician and/or a company representative) can use the external programmer 120 to vary the modulation parameters provided to the signal delivery device 111 in real time, and select optimal or particularly efficacious parameters. These parameters can include the location from which the electrical signals are emitted, as well as the characteristics of the electrical signals provided to the signal delivery device 111. In a typical process, the practitioner uses a cable assembly 114 to temporarily connect the external programmer 120 to the signal delivery device 111. The practitioner can test the efficacy of the signal delivery device 111 in an initial position. The practitioner can then disconnect the cable assembly 114 (e.g., at a connector 117), reposition the signal delivery device 111, and reapply the electrical modulation. This process can be performed iteratively until the practitioner obtains the desired position for the signal delivery device 111. Optionally, the practitioner may move the partially implanted signal delivery element 111 without disconnecting the cable assembly 114.

After a trial period with the external programmer 120, the practitioner can implant the implantable pulse generator 121 within the patient 190 for longer term treatment. The signal delivery parameters provided by the pulse generator 121 can still be updated after the pulse generator 121 is implanted, via a wireless physician's programmer 125 (e.g., a physician's remote) and/or a wireless patient programmer 124 (e.g., a patient remote). Generally, the patient 190 has control over fewer parameters than does the practitioner.

Figure 1B:
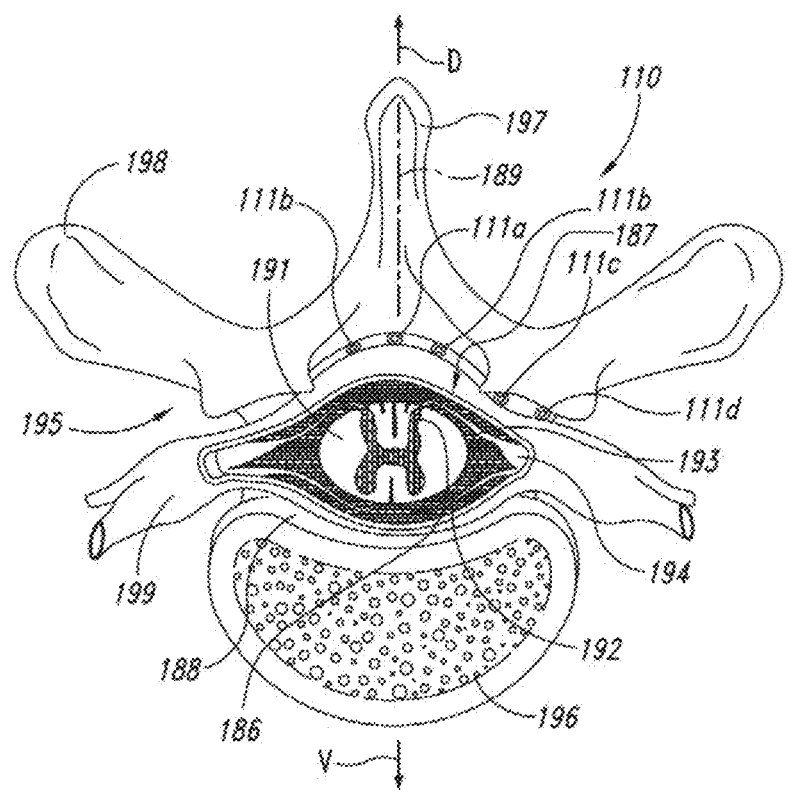
FIG. 1B is a partially schematic, cross-sectional illustration of a patient's spine, illustrating representative locations for implanted lead bodies in accordance with embodiments of the disclosure.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple signal delivery devices 111 (shown as signal delivery devices 111a-111d) implanted at representative locations. For purposes of illustration, multiple signal delivery devices 111 are shown in FIG. 1B implanted in a single patient. In actual use, any given patient will likely receive fewer than all the signal delivery devices 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry zone 187, and communicate with dorsal horn neurons located at the dorsal horn 186. In one embodiment, a single first signal delivery device 111a is positioned within the vertebral foramen 188, at or approximately at the spinal cord midline 189. In another embodiment, two second signal delivery devices 111b are positioned just off the spinal cord midline 189 (e.g., about 1 mm. offset) in opposing lateral directions so that the two signal delivery devices 111b are spaced apart from each other by about 2 mm. In still further embodiments, a single signal delivery device or pairs of signal delivery devices can be positioned at other locations, e.g., toward the outer edge of the dorsal root entry zone 187 as shown by a third signal delivery device 111c, or at the dorsal root ganglia 194, as shown by a fourth signal delivery device 111d. As will be described in further detail later, it is believed that high frequency modulation at or near the dorsal root entry zone 187, and/or at or near the dorsal horn 186 can produce effective patient pain relief, without paresthesia, without adverse sensory or motor effects, and in a manner that persists after the modulation ceases.

3.0 Addressing Patient Pain

Systems and methods for treating pain as discussed immediately below, and embodiments for addressing other patient indications via the autonomic nervous system are described later under Section 4.0. As discussed below, the pain may be addressed by applying high frequency modulation signals to dorsal neural populations. In particular embodiments, it is believed that such modulation signals may affect the wide dynamic range (WDR) neurons. Accordingly, it is further believed (and discussed in Section 4.0) that the modulation signals can affect the patient's autonomic nervous system, in addition to or in lieu of addressing patient pain.

3.1 Representative Results from Human Studies

Nevro Corporation, the assignee of the present application, has conducted several in-human clinical studies during which multiple patients were treated with the techniques, systems and devices that are disclosed herein. Nevro also commissioned animal studies focusing on mechanisms of action for the newly developed techniques. The human clinical studies are described immediately below and the animal studies are discussed thereafter.

Figure 2A:
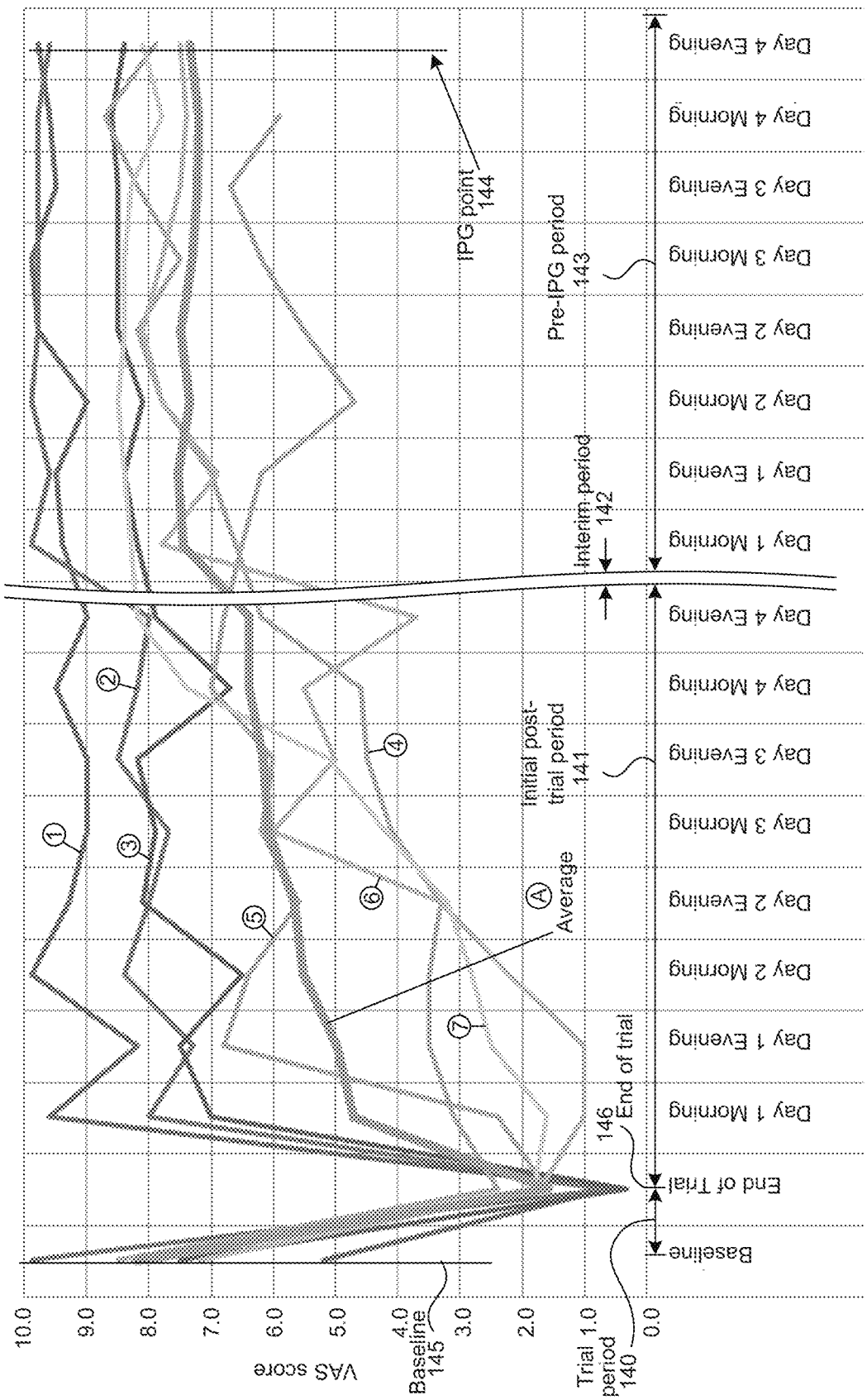
FIG. 2A is a graph illustrating representative patient VAS scores as a function of time for multiple patients receiving therapy in accordance with embodiments of the disclosure.

FIG. 2A is a graph illustrating results from patients who received therapy in accordance with the presently disclosed technology to treat chronic low back pain. In general, the therapy included high-frequency modulation at the patient's spinal cord, typically between vertebral levels T9 and T12 (inclusive), at an average location of mid T-10. The modulation signals were applied at a frequency of about 10 kHz, and at current amplitudes of from about 2.5 mA to about 3 mA. Pulse widths were about 35 μsec., at 100% duty cycle. Further details of representative modulation parameters are included in U.S. Pat. No. 8,170,675 incorporated herein by reference.

The graph shown in FIG. 2A illustrates visual analog scale ("VAS") scores for seven representative patients as a function of time during a clinical study. Individual lines for each patient are indicated with circled numbers in FIG. 2A, and the average is indicated by the circled letter "A". The VAS pain scale ranges from zero (corresponding to no sensed pain) to 10 (corresponding to unbearable pain). At the far left of FIG. 2A are VAS scores taken at a baseline point in time 145, corresponding to the patients' pain levels before receiving any high frequency modulation therapy. During a trial period 140, the patients received a high frequency modulation therapy in accordance with the foregoing parameters and the patients' VAS scores dropped significantly up to an end of trial point 146. In addition, many patients readily reduced or eliminated their intake of pain medications, despite the narcotic characteristics of these medications. During an initial post-trial period 141 (lasting, in this case, four days), the patients' VAS scores increased on average after the high frequency modulation therapy has been halted. The rate at which pain returned after the end of the trial period varied among patients, however, as will be discussed in further detail later. Following the four-day initial post-trial period 141 was an interim period 142 that lasted from about 45 days to about 80 days (depending on the patient), with the average being about 62 days. After the interim period 142, a four-day pre-IPG period 143 commenced ending at an IPG point 144. At the IPG point 144, the patients were implanted with an implantable pulse generator 121, generally similar to that described above with reference to FIG. 1A.

The VAS scores recorded at the baseline 145 and the end of the trial 146 were obtained by the patients recording their levels of pain directly to the practitioner. During the initial post-trial period 141 and the pre-IPG period 143, the patients tracked their VAS score in patient diaries.

Figure 2B:
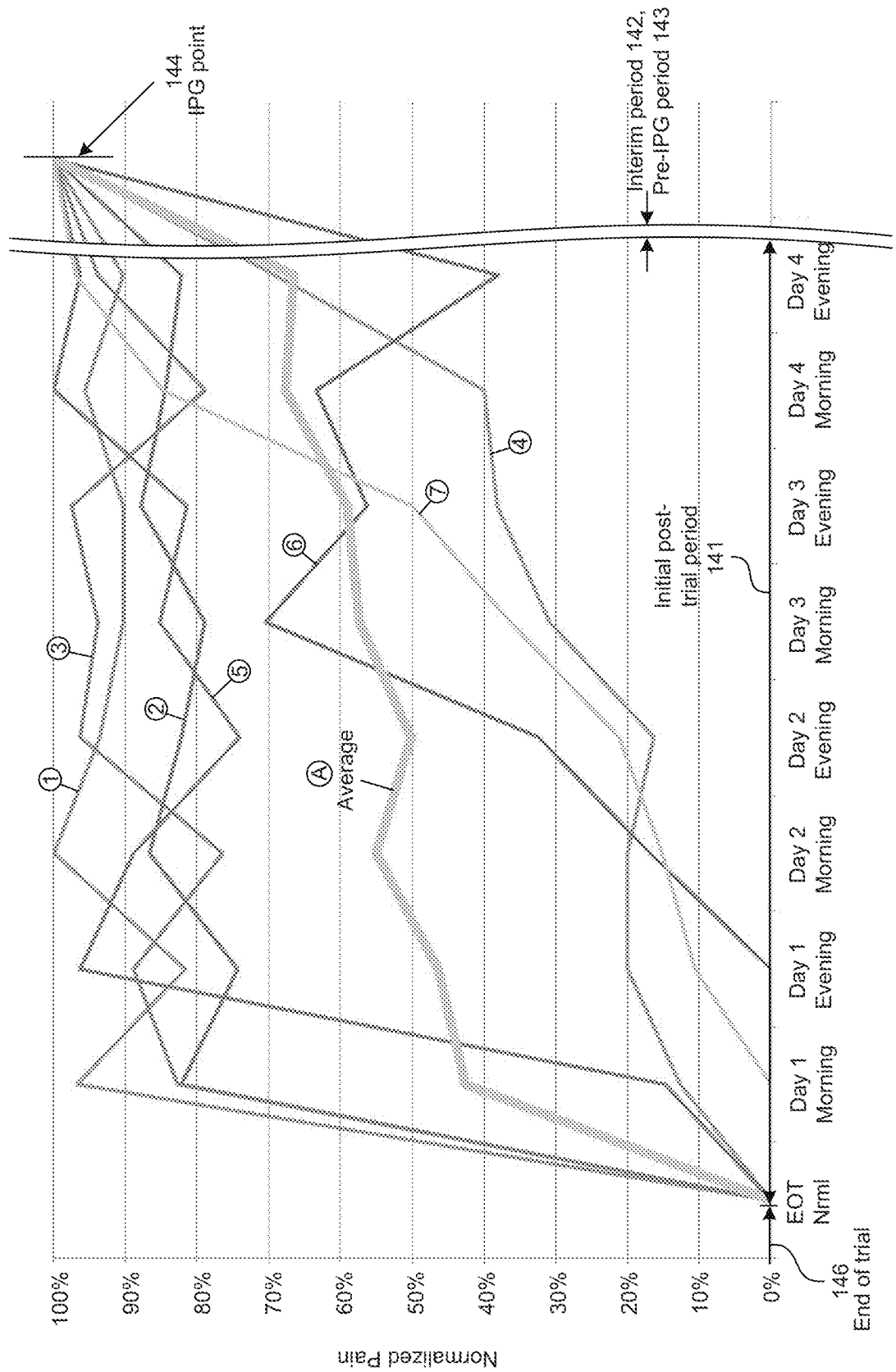
FIG. 2B is a graph illustrating normalized pain scores for the patients identified in FIG. 2A, during an initial post-trial period.

FIG. 2B illustrates data in the initial post-trial period 141 described above with reference to FIG. 2A. For each patient, the pain levels reported in FIG. 2A as VAS scores are shown in FIG. 2B as normalized by evaluating the patient's pain level at the end of trial 146 and at the IPG point 144. Accordingly, for each patient, the normalized pain value is zero at the end of trial 146, and 100% at the IPG point 144. As shown in FIG. 2B, the patients generally fell into two categories: a first group for whom the pain scores rapidly rose from 0% to nearly 100% within a span of about one day after the end of trial 146 (represented by lines 1, 2, 3 and 5); and a second group for whom the pain increase was more gradual, spanning several days before reaching levels above 50% (represented by lines 4, 6 and 7). Accordingly, the data indicate that the patients' pain levels increased compared to the levels obtained at the end of trial 146; however, different patients re-developed pain at different rates. The resolution of the data shown in FIG. 2B is not fine enough to identify precisely how long it took for the patients in the first group to feel a recurrence of high pain levels. However, it was observed by those conducting the studies that the return of the pain for all seven patients was more gradual than is typically associated with standard SCS methodologies. In particular, practitioners having experience with both standard SCS and the presently disclosed technology observed that patients receiving SCS immediately (e.g., within milliseconds) experience a return of pain upon halting the SCS treatment, while the return of pain for patients receiving the presently disclosed therapy was more gradual. Accordingly, it is expected that the persistence effect of the presently disclosed therapy after being administered for two weeks, is likely to be on the order of minutes or hours and, (for many patients), less than one day. It is also believed that the persistence effect may depend at least in part on how long the therapy was applied before it was halted. That is, it is expected that, within a given time period, the longer the patient receives the presently disclosed therapy, the longer the beneficial effect lasts after the therapy signals are halted. Accordingly, it is expected that the presently disclosed therapy can produce effects lasting at least one tenth of one second, at least one second, at least one minute, at least one hour, and/or at least one day, unlike standard SCS techniques, which typically produce effects lasting only milliseconds after the electrical signal ceases. In still further embodiments, it is expected that at least some of the lasting effect described above can be obtained by reducing the intensity (e.g., the current amplitude) of the therapy signal, without ceasing the signal altogether. In at least some embodiments (whether the signal intensity is reduced to zero or to a non-zero value), it is expected that a long enough modulation period can produce a neuroplastic or other change that can last indefinitely, to permanently reduce or eliminate patient pain.

An expected benefit of the persistence or long term effect described above is that it can reduce the need to deliver the therapy signals continuously. Instead, the signals can be delivered intermittently without significantly affecting pain relief. This arrangement can reduce power consumption, thus extending the life of an implanted battery or other power system. It is expected that the power can be cycled according to schedules other than the one explicitly shown in FIGS. 2A and 2B (e.g., other than two weeks on and up to one day off before a significant pain recurrence). The following discussion describes expected potential mechanisms of action by which the presently disclosed therapy operates, including expected mechanisms by which the presently disclosed therapy produces effects persisting after electrical modulation signals have ceased.

3.2 Representative Results from Animal Studies

Figure 3:
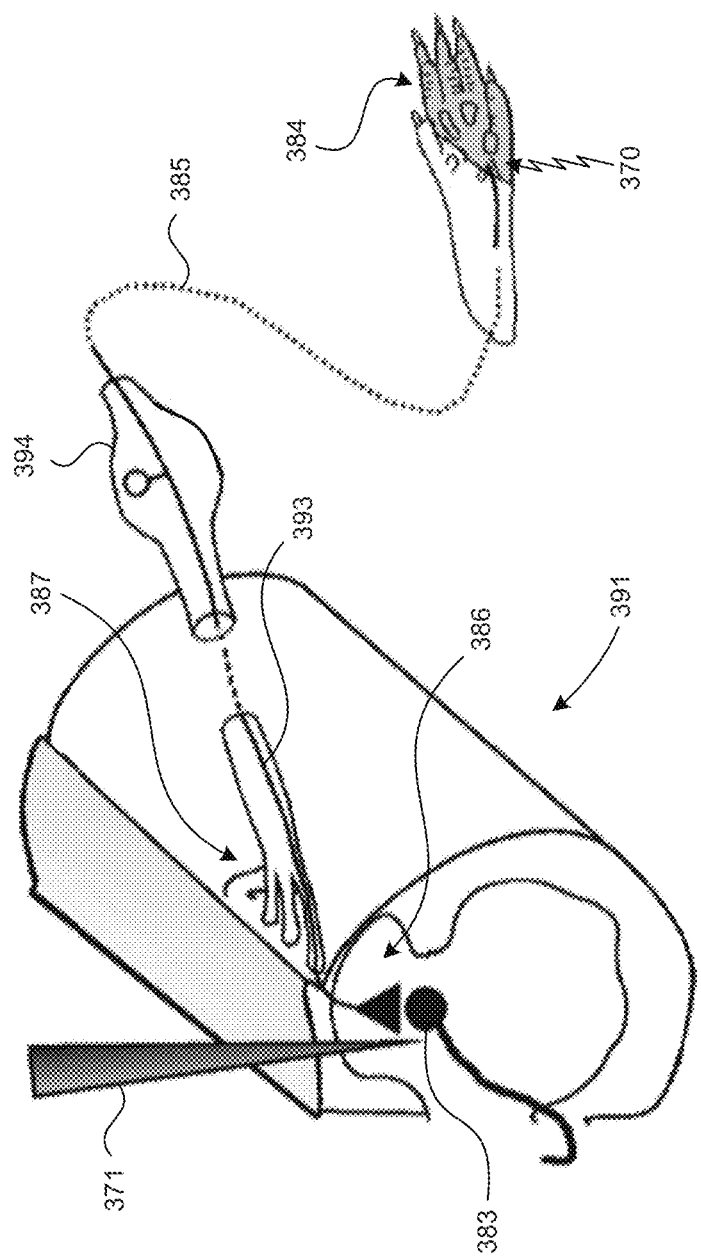
FIG. 3 is a partially schematic, isometric illustration of an animal spinal cord segment and associated nerve structures, used to demonstrate techniques in accordance with the present disclosure.

FIG. 3 is a partially schematic, isometric view of a portion of an animal spinal cord 391 illustrative of a study that was performed on a rat model to illustrate the principles described herein. Accordingly, in this particular embodiment, the illustrated spinal cord 391 is that of a rat. During this study, a noxious electrical stimulation 370 was applied to the rat's hind paw 384. Afferent pain signals triggered by the noxious stimulation 370 traveled along a peripheral nerve 385 to the dorsal root ganglion 394 and then to the dorsal root 393 at the L5 vertebral level. The dorsal root 393 joins the spinal cord 391 at the dorsal root entry zone 387, and transmits afferent signals to a dorsal horn neuron 383 located at the dorsal horn 386. The dorsal horn neuron 383 includes a wide dynamic range ("WDR") cell. An extracellular microelectrode 371 recorded signals transmitted by the dorsal horn neuron 383 to the rat's brain, in response to the noxious stimulation 370 received at the hind paw 384. A therapeutic modulation signal was applied at the dorsal root entry zone 387, proximate to the dorsal horn 386.

Figure 4:
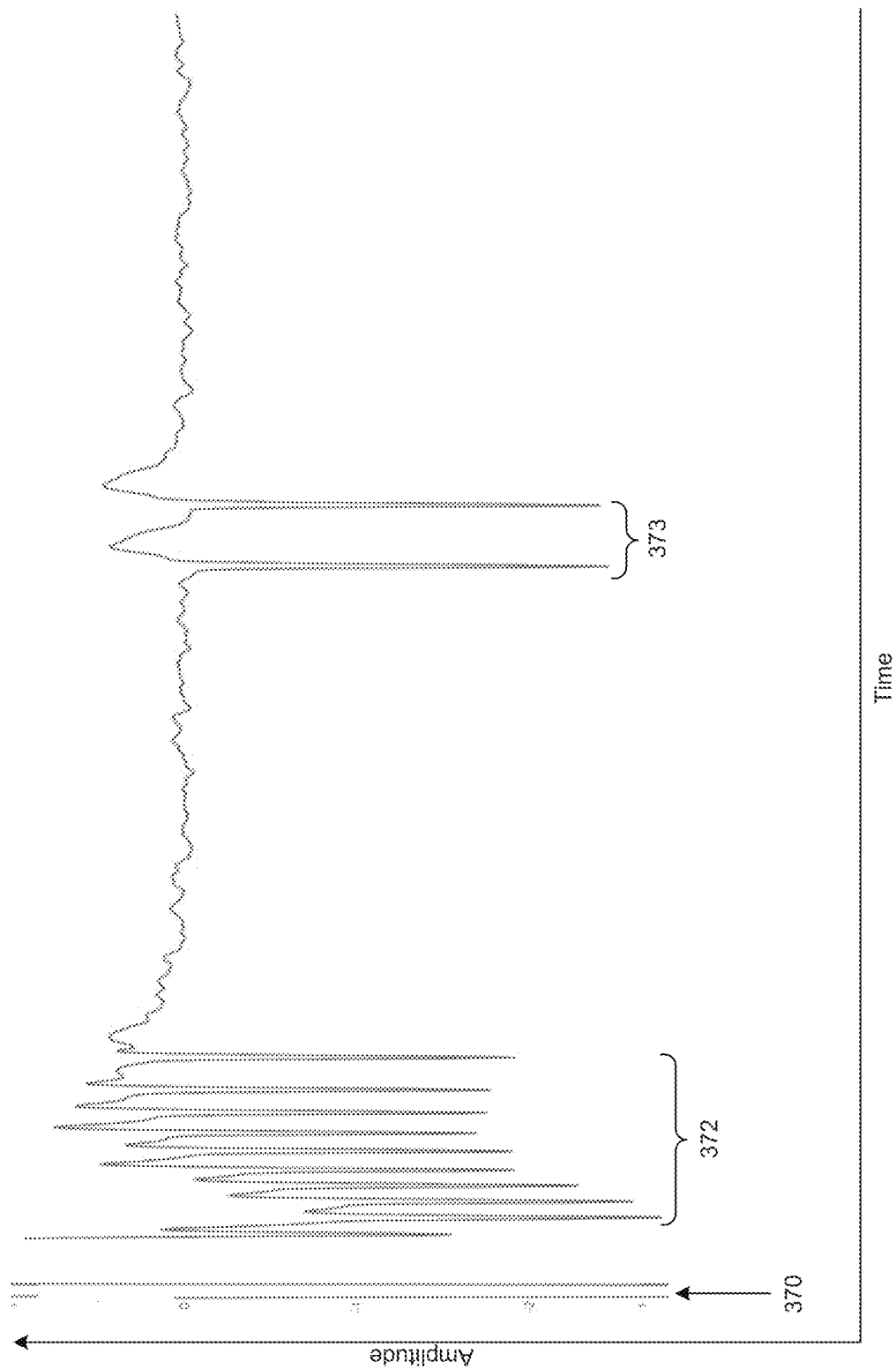
FIG. 4 is a graph illustrating stimulus and response characteristics as a function of time for an animal receiving noxious electrical stimulation in accordance with an embodiment of the disclosure.

FIG. 4 is a graph illustrating neural signal amplitude as a function of time, measured by the recording electrode 371 described above with reference to FIG. 3. FIG. 4 identifies the noxious stimulation 370 itself, the dorsal horn neuron's response to A-fiber inputs 372, and the dorsal horn neuron's response to C-fiber inputs 373. The larger A-fibers trigger an earlier response at the dorsal horn neuron than do the smaller C-fibers. Both responses are triggered by the same noxious stimulus 370. The rat's pain response is indicated by downward amplitude spikes. The foregoing response is a typical response to a noxious stimulus, absent pain modulation therapy.

Figures 5A, 5B, 5C, 5D, 5E:
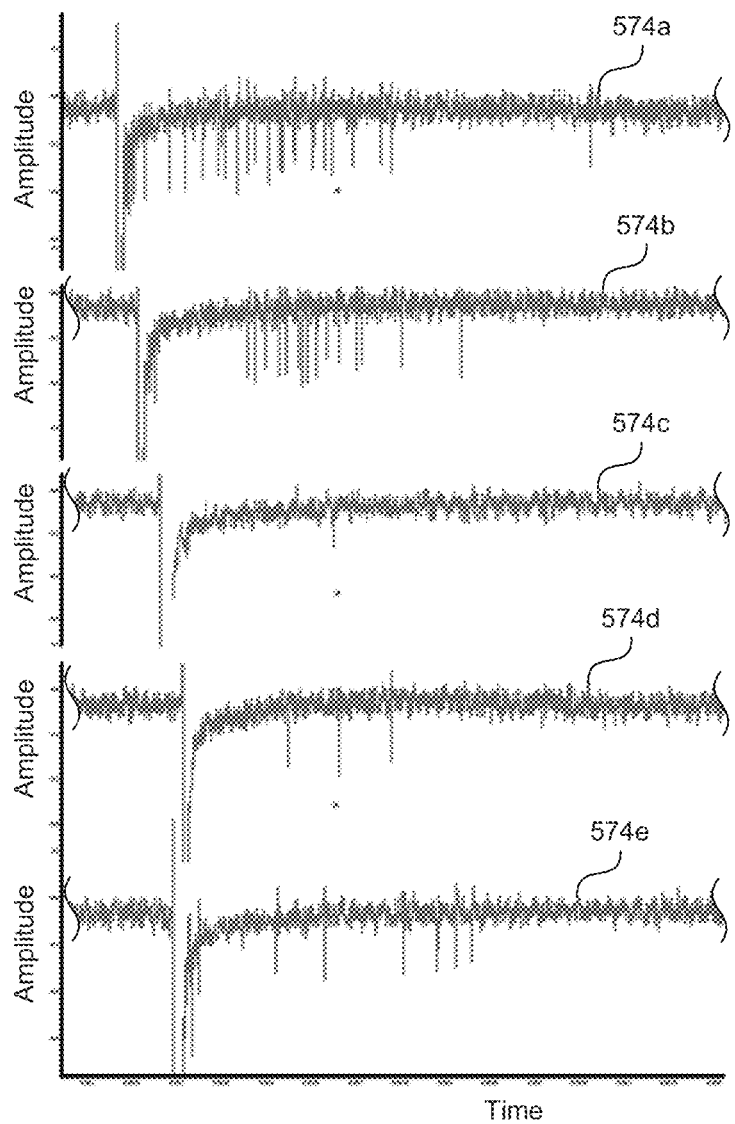
FIGS. 5A-5E illustrate response data for an animal receiving noxious electrical stimulation and therapy in accordance with an embodiment of the disclosure.

FIGS. 5A-5E illustrate the dorsal horn neuron response to ongoing noxious stimuli as the applied therapy signal was altered. The signal applied to each rat was applied at a constant frequency, which varied from rat to rat over a range of from about 3 kHz to about 100 kHz. The response data (which were obtained from nine rats) were relatively insensitive to frequency over this range. During the course of this study, the noxious stimuli were provided repeatedly at a constant rate of one stimulus per second over an approximately five-minute period. At the outset of the five-minute period, the therapy signal was turned off, resulting in a baseline response 574a shown in FIG. 5A, and then gradually increased as shown in FIG. 5B, to a maximum intensity shown in FIG. 5C. During the period shown in FIG. 5D, the intensity of the therapy signal was reduced, and in FIG. 5E, the therapy signal was turned off. Consistent with the data shown in FIG. 4, the rat's pain response is indicated by downward spikes. The baseline response 574a has a relatively large number of spikes, and the number of spikes begins to reduce as the intensity of the modulation signal is increased (see response 574b in FIG. 5B). At the maximum therapy signal intensity, the number of spikes has been reduced to nearly zero as indicated by response 574c in FIG. 5C. As the therapy signal intensity is then reduced, the spikes begin to return (see response 574d, FIG. 5D), and when the modulation signal is turned off, the spikes continue to return (see response 574e, FIG. 5E). Significantly, the number of spikes shown in FIG. 5E (10-20 seconds after the therapy has been turned off) is not as great as the number of spikes generated in the baseline response 574a shown in FIG. 5A. These data are accordingly consistent with the human trial data described above with reference to FIGS. 2A and 2B, which indicated a beneficial effect lasting beyond the cessation of the therapy signal. These data also differ significantly from results obtained from similar studies conducted with standard SCS. Notably, dorsal horn recordings during standard SCS treatments do not indicate a reduction in amplitude spikes.

Figures 6A, 6B:
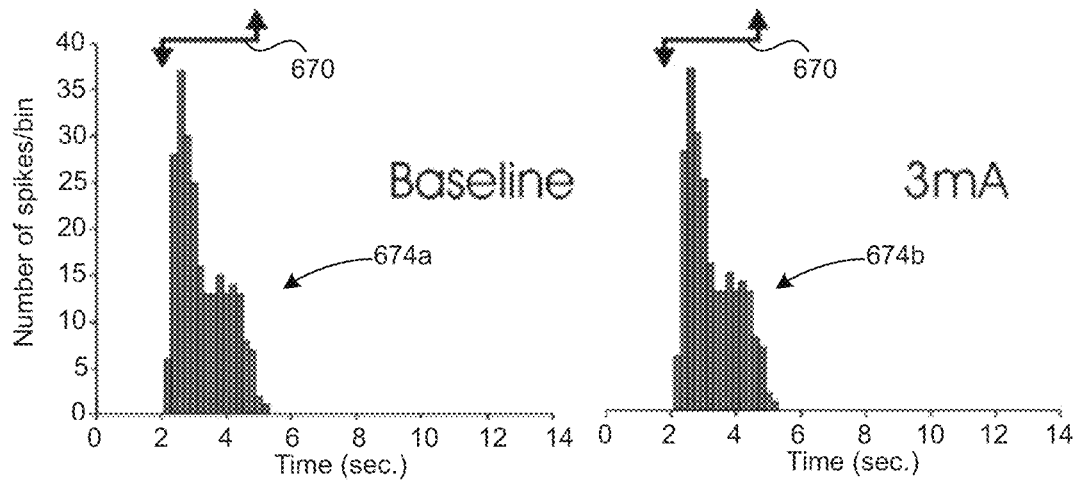
FIGS. 6A-6F illustrate animal response data for animals receiving noxious pinch stimuli in accordance with another embodiment of the disclosure.
Figures 6C, 6D:
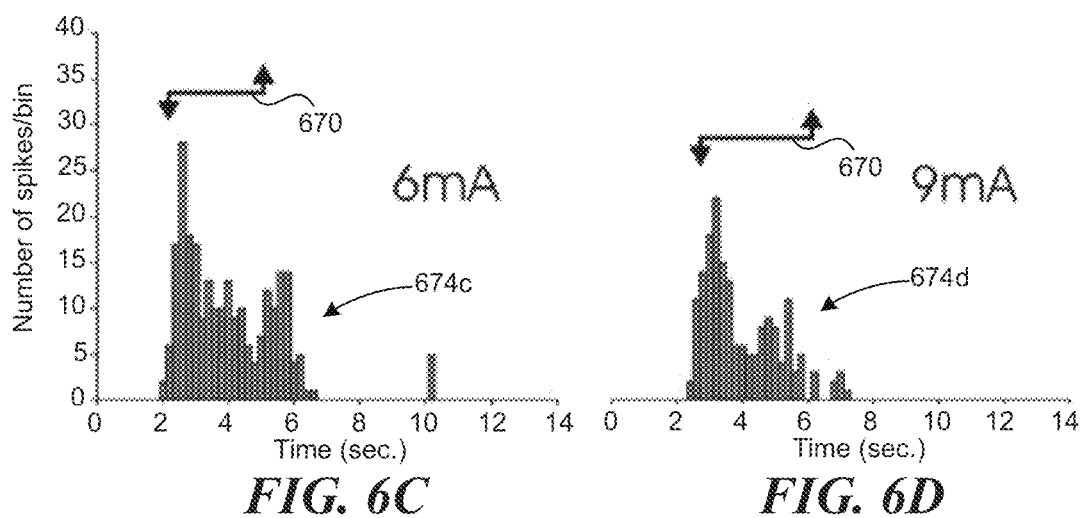
Figures 6E, 6F:
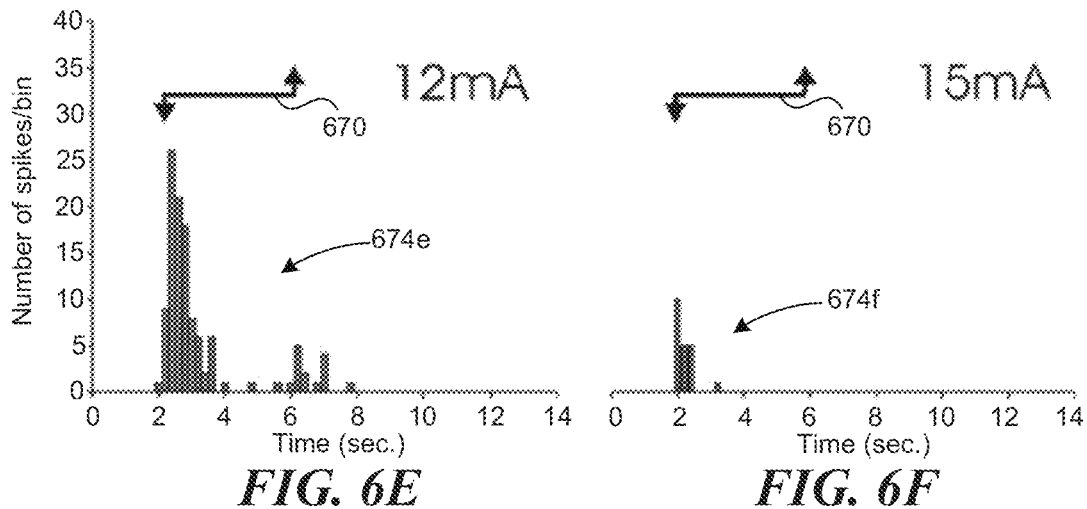

FIGS. 6A-6F illustrate animal response data in a rat model to a different noxious stimulus; in particular, a pinch stimulus 670. The pinch stimulus is a mechanical pinch (rather than an electrical stimulus) at the rat's hindpaw. In each succeeding figure in the series of FIGS. 6A-6F, the amplitude of the therapy signal was increased. The levels to which the signal amplitude was increased were significantly higher than for the human study simply due to a cruder (e.g., less efficient) coupling between the signal delivery electrode and the target neural population. The vertical axis of each Figure indicates the number of spikes (e.g., the spike-shaped inputs 372, 373 shown in FIG. 3) per bin; that is, the number of spikes occurring during a given time period. In the particular embodiment shown in FIGS. 6A-6F, each bin has a duration of 0.2 second, so that there are a total of five bins per second, or 10 bins during each two-second period. The pinch stimulus 670 lasts for three to five seconds in each of FIGS. 6A-6F. In FIG. 6A, the baseline response 674a indicates a large number of spikes per bin extending over the duration of the pinch stimulus 670. As shown in FIGS. 6B-6F, the number of spikes per bin decreases, as indicated by responses 674b-674f, respectively. In the final Figure in this series (FIG. 6F), the response 674f is insignificant or nearly insignificant when compared with the baseline response 674a shown in FIG. 6A.

The foregoing rat data was confirmed in a subsequent study using a large animal model (goat). Based on these data, it is clear that therapy signals in accordance with the present technology reduce pain; further, that they do so in a manner consistent with that observed during the human studies.

Returning now to FIG. 3, it is expected (without being bound by theory) that the therapy signals act to reduce pain via one or both of two mechanisms: (1) by reducing neural transmissions entering the spinal cord at the dorsal root 393 and/or the dorsal root entry zone 387, and/or (2) by reducing neural activity at the dorsal horn 386 itself. It is further expected that the therapy signals described in the context of the rat model shown in FIG. 3 operate in a similar manner on the corresponding structures of the human anatomy, e.g., those shown in FIG. 1B. In particular, it is generally known that chronic pain patients may be in a state of prolonged sensory sensitization at both the nociceptive afferent neurons (e.g., the peripheral nerve 385 and the associated dorsal root 393) and at higher order neural systems (e.g., the dorsal horn neuron 383). It is also known that the dorsal horn neurons 383 (e.g., the WDR cells) are sensitized in chronic pain states. The noxious stimuli applied during the animal studies can result in an acute "windup" of the WDR cells (e.g., to a hyperactive state). In accordance with mechanism (1) above, it is believed that the therapy signals applied using the current technology operate to reduce pain by reducing, suppressing, and/or attenuating the afferent nociceptive inputs delivered to the WDR cells 383, as it is expected that these inputs, unless attenuated, can be responsible for the sensitized state of the WDR cells 383. In accordance with mechanism (2) above, it is expected that the presently disclosed therapy can act directly on the WDR cells 383 to desensitize these cells. In particular, the patients selected to receive the therapy described above with reference to FIGS. 2A-2B included patients whose pain was not correlated with peripheral stimuli. In other words, these patients had hypersensitive WDR cells 383 independent of whether signals were transmitted to the WDR cells 383 via peripheral nerve inputs or not. These patients, along with the other treated patients, experienced the significant pain reductions described above. Accordingly, it is believed that the disclosed therapy can operate directly on the WDR cells 383 to reduce the activity level of hyperactive WDR cells 383, and/or can reduce incoming afferent signals from the peripheral nerve 385 and dorsal root 393. It is further believed that the effect of the presently disclosed therapy on peripheral inputs may produce short term pain relief, and the effect on the WDR cells may produce longer term pain relief. Whether the reduced output of the WDR cells results from mechanism (1), mechanism (2), or both, it is further expected that the high frequency characteristics of the therapeutic signals produce the observed results. In addition, embodiments of the presently disclosed therapy produce pain reduction without the side effects generally associated with standard SCS, as discussed further in U.S. Pat. No. 8,170,675, previously incorporated herein by reference. These and other advantages associated with embodiments of the presently disclosed technology are described further below.

Certain of the foregoing embodiments can produce one or more of a variety of advantages, for the patient and/or the practitioner, when compared with standard SCS therapies. Some of these benefits were described above. For example, the patient can receive beneficial effects from the modulation therapy after the modulation signal has ceased. In addition, the patient can receive effective pain relief without simultaneous paresthesia, without simultaneous patient-detectable disruptions to normal sensory signals along the spinal cord, and/or without simultaneous patient-detectable disruptions to normal motor signals along the spinal cord. In particular embodiments, while the therapy may create some effect on normal motor and/or sensory signals, the effect is below a level that the patient can reliably detect intrinsically, e.g., without the aid of external assistance via instruments or other devices. Accordingly, the patient's levels of motor signaling and other sensory signaling (other than signaling associated with the target pain) can be maintained at pretreatment levels. For example, the patient can experience a significant pain reduction that is largely independent of the patient's movement and position. In particular, the patient can assume a variety of positions and/or undertake a variety of movements associated with activities of daily living and/or other activities, without the need to adjust the parameters in accordance with which the therapy is applied to the patient (e.g., the signal amplitude). This result can greatly simplify the patient's life and reduce the effort required by the patient to experience pain relief while engaging in a variety of activities. This result can also provide an improved lifestyle for patients who experience pain during sleep.

Even for patients who receive a therapeutic benefit from changes in signal amplitude, the foregoing therapy can provide advantages. For example, such patients can choose from a limited number of programs (e.g., two or three) each with a different amplitude and/or other signal delivery parameter, to address some or all of the patient's pain. In one such example, the patient activates one program before sleeping and another after waking. In another such example, the patient activates one program before sleeping, a second program after waking, and a third program before engaging in particular activities that would otherwise cause pain. This reduced set of patient options can greatly simplify the patient's ability to easily manage pain, without reducing (and in fact, increasing) the circumstances under which the therapy effectively addresses pain. In any embodiments that include multiple programs, the patient's workload can be further reduced by automatically detecting a change in patient circumstance, and automatically identifying and delivering the appropriate therapy regimen. Additional details of such techniques and associated systems are disclosed in co-pending U.S. application Ser. No. 12/703,683, incorporated herein by reference.

Another benefit observed during clinical studies is that when the patient does experience a change in the therapy level, it is a gradual change. This is unlike typical changes associated with conventional SCS therapies. With conventional SCS therapies (e.g., neuromodulation therapies where electrical stimulation is provided between 2-1,200 Hz, and wherein paresthesia is used to mask a patient's sensation of pain), if a patient changes position and/or changes an amplitude setting, the patient can experience a sudden onset of pain, often described by patients as unbearable. By contrast, patients in the clinical studies described above, when treated with the presently disclosed therapy, reported a gradual onset of pain when signal amplitude was increased beyond a threshold level, and/or when the patient changed position, with the pain described as gradually becoming uncomfortable. One patient described a sensation akin to a cramp coming on, but never fully developing. This significant difference in patient response to changes in signal delivery parameters can allow the patient to more freely change signal delivery parameters and/or posture when desired, without fear of creating an immediately painful effect.

Another observation from the clinical studies described above is that the amplitude "window" between the onset of effective therapy and the onset of pain or discomfort is relatively broad, and in particular, broader than it is for standard SCS treatment. For example, during standard SCS treatment, the patient typically experiences a pain reduction at a particular amplitude, and begins experiencing pain from the therapeutic signal (which may have a sudden onset, as described above) at from about 1.2 to about 1.6 times that amplitude. This corresponds to an average dynamic range of about 1.4. In addition, patients receiving standard SCS stimulation typically wish to receive the stimulation at close to the pain onset level because the therapy is often most effective at that level. Accordingly, patient preferences may further reduce the effective dynamic range. By contrast, therapy in accordance with embodiments of the presently disclosed technology resulted in patients obtaining pain relief at 1 mA or less, and not encountering pain or muscle capture until the applied signal had an amplitude of 4 mA, and in some cases up to about 5 mA, 6 mA, or 8 mA, corresponding to a much larger dynamic range (e.g., larger than 1.6 or 60% in some embodiments, or larger than 100% in other embodiments). In particular embodiments, therapy resulted at 2-3 mA, and sensation at greater than 7 mA. Even at the forgoing amplitude levels, the pain experienced by the patients was significantly less than that associated with standard SCS pain onset. An expected advantage of this result is that the patient and practitioner can have significantly wider latitude in selecting an appropriate therapy amplitude with the presently disclosed methodology than with standard SCS methodologies. For example, the practitioner can increase the signal amplitude in an effort to affect more (e.g., deeper) fibers at the spinal cord, without triggering unwanted side effects. The existence of a wider amplitude window may also contribute to the relative insensitivity of the presently disclosed therapy to changes in patient posture and/or activity. For example, if the relative position between the implanted lead and the target neural population changes as the patient moves, the effective strength of the signal when it reaches the target neural population may also change. When the target neural population is insensitive to a wider range of signal strengths, this effect can in turn allow greater patient range of motion without triggering undesirable side effects.

Figure 7A:
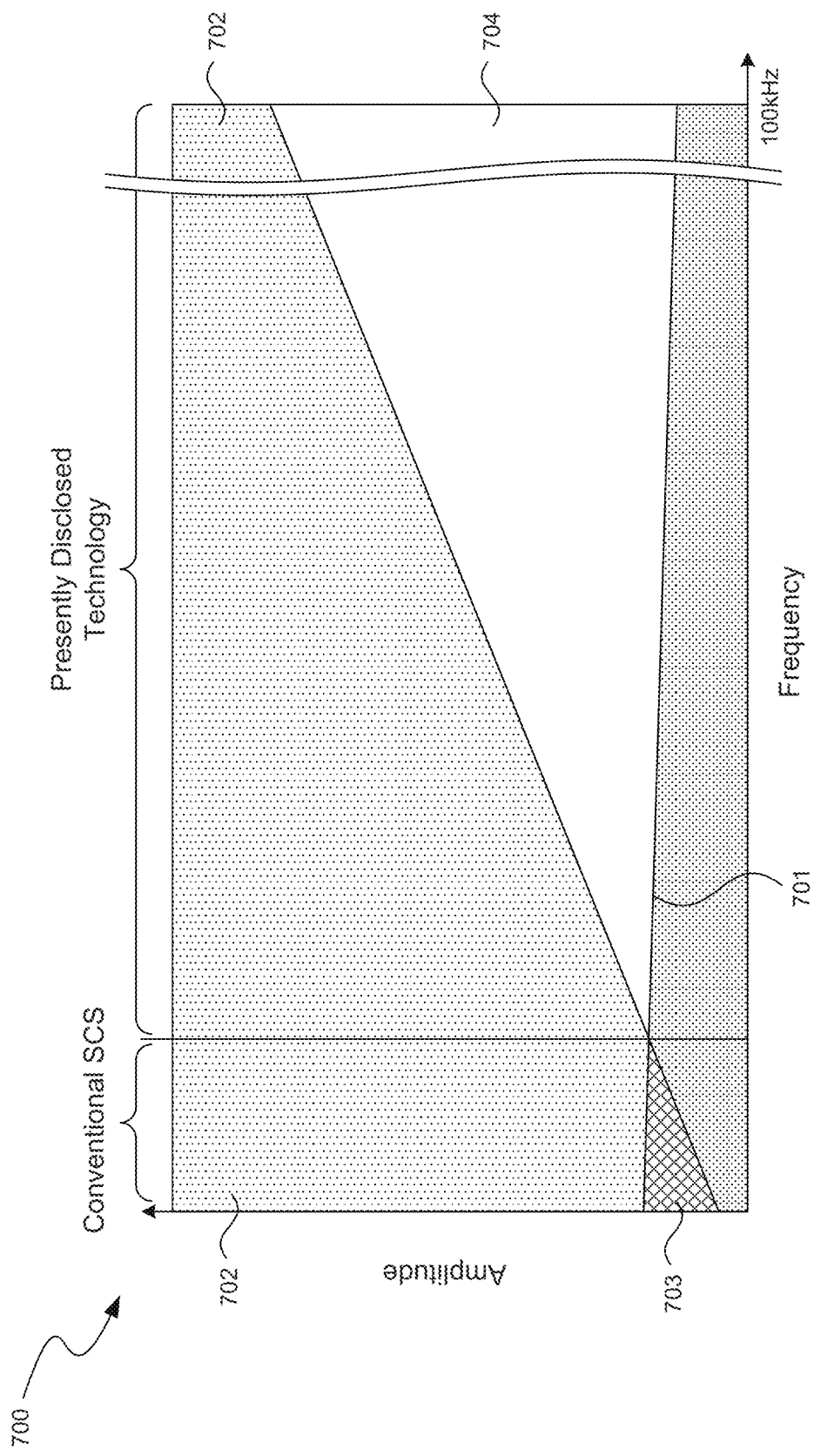
FIG. 7A is a graphical illustration comparing modulation amplitude effects for standard SCS with those for the presently disclosed technology.

FIG. 7A illustrates a graph 700 identifying amplitude as a function of frequency for conventional SCS and for therapy in accordance with embodiments of the presently disclosed technology. Threshold amplitude level 701 indicates generally the minimum amplitude necessary to achieve a therapeutic effect, e.g., pain reduction. A first region 702 corresponds to amplitudes, as a function of frequency, for which the patient senses paresthesia induced by the therapy, pain induced by the therapy, and/or uncomfortable or undesired muscle stimulation induced by the therapy. As shown in FIG. 7A, at conventional SCS frequencies, the first region 702 extends below the threshold amplitude level 701. Accordingly, a second region 703 indicates that the patient undergoing conventional SCS therapy typically detects paresthesia, other sensory effects, and/or undesirable motor effects below the amplitude necessary to achieve a therapeutic effect. One or more of these side effects are also present at amplitudes above the threshold amplitude level 701 required to achieve the therapeutic effect. By contrast, at frequencies associated with the presently disclosed technology, a "window" 704 exists between the threshold amplitude level 701 and the first region 702. Accordingly, the patient can receive therapeutic benefits at amplitudes above the threshold amplitude level 701, and below the amplitude at which the patient may experience undesirable side effects (e.g., paresthesia, sensory effects and/or motor effects).

Figure 7B:
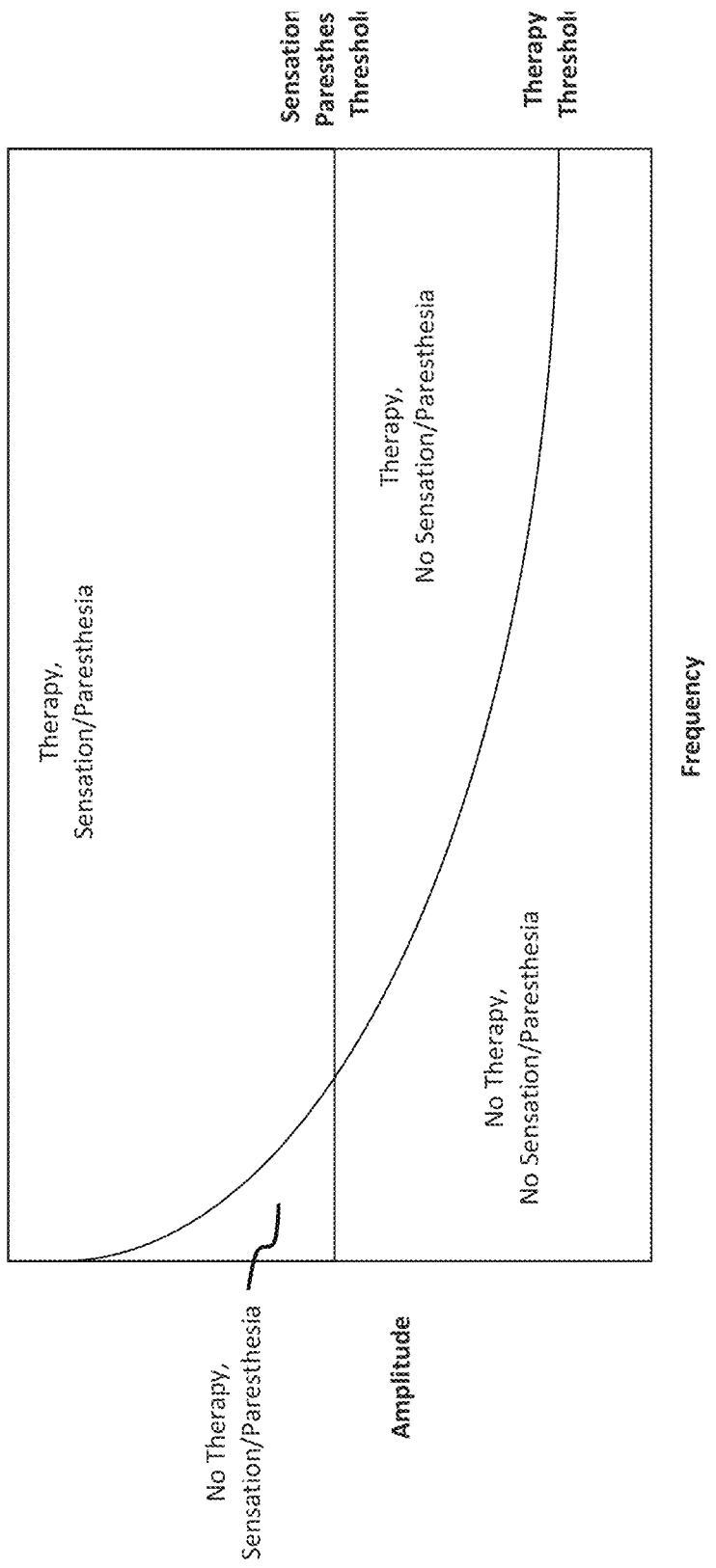
FIG. 7B is a graph of amplitude as a function of frequency, illustrating different therapeutic and non-therapeutic regimes.

FIG. 7B is a graph of amplitude as a function of frequency, illustrating representative regimes in accordance with a particular model for therapy delivery. FIG. 7B illustrates a sensation/paresthesia threshold, and a therapy threshold. These curves cross, creating four regions, each of which is identified in FIG. 7B based on whether or not the patient receives therapy, and whether or not the patient perceives sensation and/or paresthesia. Particular embodiments of the presently disclosed technology operate in the range identified as "Therapy, No Sensation/Paresthesia" to produce the therapeutic results without paresthesia, discussed above.

Although the presently disclosed therapies may allow the practitioner to provide modulation over a broader range of amplitudes, in at least some cases, the practitioner may not need to use the entire range. For example, as described above, the instances in which the patient may need to adjust the therapy may be significantly reduced when compared with standard SCS therapy because the presently disclosed therapy is relatively insensitive to patient position, posture and activity level. In addition to or in lieu of the foregoing effect, the amplitude of the signals applied in accordance with the presently disclosed techniques may be lower than the amplitude associated with standard SCS because the presently disclosed techniques may target neurons that are closer to the surface of the spinal cord. For example, it is believed that the nerve fibers associated with low back pain enter the spinal cord between T9 and T12 (inclusive), and are thus close to the spinal cord surface at these vertebral locations. Accordingly, the strength of the therapeutic signal (e.g., the current amplitude) can be modest because the signal need not penetrate through a significant depth of spinal cord tissue to have the intended effect. Such low amplitude signals can have a reduced (or zero) tendency for triggering side effects, such as unwanted sensory and/or motor responses. Such low amplitude signals can also reduce the power required by the implanted pulse generator, and can therefore extend the battery life and the associated time between recharging and/or replacing the battery.

Yet another expected benefit of providing therapy in accordance with the presently disclosed parameters is that the practitioner need not implant the lead with the same level of precision as is typically required for standard SCS lead placement. For example, while at least some of the foregoing results were obtained for patients having two leads (one positioned on either side of the spinal cord midline), it is expected that patients will receive the same or generally similar pain relief with only a single lead placed at the midline. Accordingly, the practitioner may need to implant only one lead, rather than two. It is still further expected that the patient may receive pain relief on one side of the body when the lead is positioned offset from the spinal cord midline in the opposite direction. Thus, even if the patient has bilateral pain, e.g., with pain worse on one side than the other, the patient's pain can be addressed with a single implanted lead. Still further, it is expected that the lead position can vary laterally from the anatomical and/or physiological spinal cord midline to a position 3-5 mm. away from the spinal cord midline (e.g., out to the dorsal root entry zone or DREZ). The foregoing identifiers of the midline may differ, but the expectation is that the foregoing range is effective for both anatomical and physiological identifications of the midline, e.g., as a result of the robust nature of the present therapy. Yet further, it is expected that the lead (or more particularly, the active contact or contacts on the lead) can be positioned at any of a variety of axial locations in a range of about T8-T11 or T8-T12 in one embodiment, and a range of one to two vertebral bodies within T8-T11 or T8-T12 in another embodiment, while still providing effective treatment for low back pain. Accordingly, the practitioner's selected implant site need not be identified or located as precisely as it is for standard SCS procedures (axially and/or laterally), while still producing significant patient benefits. In particular, the practitioner can locate the active contacts within the foregoing ranges without adjusting the contact positions in an effort to increase treatment efficacy and/or patient comfort. In addition, in particular embodiments, contacts at the foregoing locations can be the only active contacts delivering therapy to the patient. The foregoing features, alone or in combination, can reduce the amount of time required to implant the lead, and can give the practitioner greater flexibility when implanting the lead. For example, if the patient has scar tissue or another impediment at a preferred implant site, the practitioner can locate the lead elsewhere and still obtain beneficial results.

Still another expected benefit, which can result from the foregoing observed insensitivities to lead placement and signal amplitude, is that the need for conducting a mapping procedure at the time the lead is implanted may be significantly reduced or eliminated. This is an advantage for both the patient and the practitioner because it reduces the amount of time and effort required to establish an effective therapy regimen. In particular, standard SCS therapy typically requires that the practitioner adjust the position of the lead and the amplitude of the signals delivered by the lead, while the patient is in the operating room reporting whether or not pain reduction is achieved. Because the presently disclosed techniques are relatively insensitive to lead position and amplitude, the mapping process can be eliminated entirely. Instead, the practitioner can place the lead at a selected vertebral location (e.g., about T8-T11) and apply the signal at a pre-selected amplitude (e.g., 2 to 3 mA), with a significantly reduced or eliminated trial-and-error optimization process (for a contact selection and/or amplitude selection), and then release the patient. In addition to or in lieu of the foregoing effect, the practitioner can, in at least some embodiments, provide effective therapy to the patient with a simple bipole arrangement of electrodes, as opposed to a tripole or other more complex arrangement that is used in existing systems to steer or otherwise direct therapeutic signals. In light of the foregoing effect(s), it is expected that the time required to complete a patient lead implant procedure and select signal delivery parameters can be reduced by a factor of two or more, in particular embodiments. As a result, the practitioner can treat more patients per day, and the patients can more quickly engage in activities without pain.

The foregoing effect(s) can extend not only to the mapping procedure conducted at the practitioner's facility, but also to the subsequent trial period. In particular, patients receiving standard SCS treatment typically spend a week after receiving a lead implant during which they adjust the amplitude applied to the lead in an attempt to establish suitable amplitudes for any of a variety of patient positions and patient activities. Because embodiments of the presently disclosed therapy are relatively insensitive to patient position and activity level, the need for this trial and error period can be reduced or eliminated.

Still another expected benefit associated with embodiments of the presently disclosed treatment is that the treatment may be less susceptible to patient habituation. In particular, it is expected that in at least some cases, the high frequency signal applied to the patient can produce an asynchronous neural response, as is disclosed in co-pending U.S. application Ser. No. 12/362,244, incorporated herein by reference. The asynchronous response may be less likely to produce habituation than a synchronous response, which can result from lower frequency modulation.

Yet another feature of embodiments of the foregoing therapy is that the therapy can be applied without distinguishing between anodic contacts and cathodic contacts. As described in greater detail in U.S. application Ser. No. 12/765,790, incorporated herein by reference, this feature can simplify the process of establishing a therapy regimen for the patient. In addition, due to the high frequency of the waveform, the adjacent tissue may perceive the waveform as a pseudo steady state signal. As a result of either or both of the foregoing effects, tissue adjacent both electrodes may be beneficially affected. This is unlike standard SCS waveforms for which one electrode is consistently cathodic and another is consistently anodic.

In any of the foregoing embodiments, aspects of the therapy provided to the patient may be varied, while still obtaining beneficial results. For example, the location of the lead body (and in particular, the lead body electrodes or contacts) can be varied over the significant lateral and/or axial ranges described above. Other characteristics of the applied signal can also be varied. For example, the signal can be delivered at a frequency of from about 1.5 kHz to about 100 kHz, and in particular embodiments, from about 1.5 kHz to about 50 kHz. In more particular embodiments, the signal can be provided at frequencies of from about 3 kHz to about 20 kHz, or from about 3 kHz to about 15 kHz, or from about 5 kHz to about 15 kHz, or from about 3 kHz to about 10 kHz. The amplitude of the signal can range from about 0.1 mA to about 20 mA in a particular embodiment, and in further particular embodiments, can range from about 0.5 mA to about 10 mA, or about 0.5 mA to about 4 mA, or about 0.5 mA to about 2.5 mA. The amplitude of the applied signal can be ramped up and/or down. In particular embodiments, the amplitude can be increased or set at an initial level to establish a therapeutic effect, and then reduced to a lower level to save power without forsaking efficacy, as is disclosed in pending U.S. application Ser. No. 12/264,836, filed Nov. 4, 2008, incorporated herein by reference. In particular embodiments, the signal amplitude refers to the electrical current level, e.g., for current-controlled systems. In other embodiments, the signal amplitude can refer to the electrical voltage level, e.g., for voltage-controlled systems. The pulse width (e.g., for just the cathodic phase of the pulses) can vary from about 10 microseconds to about 333 microseconds. In further particular embodiments, the pulse width can range from about 25 microseconds to about 166 microseconds, or from about 33 microseconds to about 100 microseconds, or from about 50 microseconds to about 166 microseconds, or from about 30 to about 35 microseconds. The specific values selected for the foregoing parameters may vary from patient to patient and/or from indication to indication and/or on the basis of the selected vertebral location. In addition, the methodology may make use of other parameters, in addition to or in lieu of those described above, to monitor and/or control patient therapy. For example, in cases for which the pulse generator includes a constant voltage arrangement rather than a constant current arrangement, the current values described above may be replaced with corresponding voltage values.

In at least some embodiments, it is expected that the foregoing amplitudes will be suprathreshold. As used herein, the term "suprathreshold" refers generally to a signal that produces, triggers and/or otherwise results in an action potential at the target neuron(s) or neural population. It is also expected that, in at least some embodiments, the neural response to the foregoing signals will be asynchronous, as described above. Accordingly, the frequency of the signal can be selected to be higher (e.g., between two and ten times higher) than the refractory period of the target neurons at the patient's spinal cord, which in at least some embodiments is expected to produce an asynchronous response.

Patients can receive multiple signals in accordance with still further embodiments of the disclosure. For example, patients can receive two or more signals, each with different signal delivery parameters. In one particular example, the signals are interleaved with each other. For instance, the patient can receive 5 kHz pulses interleaved with 10 KHz pulses. In other embodiments, patients can receive sequential "packets" of pulses at different frequencies, with each packet having a duration of less than one second, several seconds, several minutes, or longer depending upon the particular patient and indication.

4.0 Effects of High Frequency Modulation on the Autonomic Nervous System

The autonomic nervous system (ANS) is largely responsible for automatically and subconsciously regulating many systems of the body, including the cardiovascular, renal, gastrointestinal, and thermoregulatory systems. By regulating these systems, the ANS can enable the body to adapt to changes in the environment, for example, changing states of stress. Autonomic nerve fibers innervate a variety of tissues, including cardiac muscle, smooth muscle, and glands. These nerve fibers help to regulate functions associated with the foregoing tissues, including but not limited to blood pressure, blood flow, gastrointestinal functions, body temperature, bronchial dilation, blood glucose levels, metabolism, micturition and defecation, pupilary light and accommodation reflexes, and glandular secretions. The effect of the ANS on selected organs can be demonstrated by cutting the nerve fibers. If the autonomic nerve fibers to an organ are cut or otherwise interrupted, the organ will fail to adjust to changing conditions. For example, if the autonomic nerve fibers to the heart are cut, the heart will largely lose its ability to increase cardiac output under stress.

The autonomic nervous system includes the sympathetic system and the parasympathetic system. These two systems in many instances have opposite effects and accordingly, each one can balance the effect of the other. FIG. 8 illustrates representative organs innervated by the ANS, together with the effects created by both the sympathetic system and the parasympathetic system.

In accordance with the presently disclosed technology, it is believed that organ dysfunction may be caused by (a) an imbalance in the parasympathetic and sympathetic effects, and/or (b) the combined effect of the parasympathetic and sympathetic systems being higher or lower than normal. The foregoing effects individually or together, are referred to herein generally as autonomic system deficits. One approach to addressing organ dysfunction in accordance with embodiments of the present technology is to apply high frequency signals to normalize the autonomic nervous system, e.g., to reduce or eliminate autonomic system deficits. Accordingly, normalizing the autonomic nervous system can include providing or increasing the level of homeostatis or equilibrium of the ANS system, and/or altering the overall output of the ANS. For example, the autonomic system can experience a deficit when the effect of the sympathetic system is stronger than or dominates the effect of the parasympathetic system, or vice versa. Without being bound by theory, it is believed that the high frequency modulation signals can bring equilibrium to the ANS (or at least reduce dis-equilibrium when one of the sympathetic and parasympathetic systems is more active and/or creates a greater effect than the other.

As was discussed above in the context of pain treatment, one possible mechanism of action by which high frequency signals are expected to address pain is to reduce the excitability of wide dynamic range (WDR) neurons. It is believed that high frequency signals can operate in a similar and/or analogous manner to reduce excitability of an overactive sympathetic or parasympathetic system and/or otherwise reduce autonomic system deficits.

Electrical signals to address autonomic system deficits can be applied to the spinal cord in manners generally similar to those discussed above in the context of reducing pain, and in accordance with modulation parameters generally similar to those described above in the context of reducing pain. For example, the signal can be applied in accordance with any of the foregoing frequency ranges of from about 1.5 kHz to about 100 KHz, and in accordance with any of the foregoing current amplitude ranges of from about 0.1 mA to about 20 mA. Depending upon the embodiment, a particular modulation signal can be directed to (a) reduce pain, (b) control the autonomic system (e.g., reduce autonomic system deficits) or (c) both.

In at least some embodiments, the modulation signal can be applied at a particular vertebral level associated with the organ of interest. For example, the modulation signal can be applied to upper thoracic vertebral levels to address cardiac and/or pulmonary autonomic system deficits. In other embodiments, the modulation signal can be applied to cervical levels of the spinal cord (e.g., C3-C5) to address organs associated not only with that vertebral level, but also with vertebral levels below it. Further details of particular vertebral levels and associated organs are described in U.S. Pat. No. 8,170,675, previously incorporated herein by reference.

The high frequency modulation signal can operate on the targeted organ or organs in accordance with any of a number of mechanisms. For example, the high frequency modulation signal can have an effect on a network of neurons, rather than an effect on a particular neuron. This network effect can in turn operate to normalize the autonomic system described above. In accordance with another mechanism of action, the high frequency modulation signal can affect gene expression. For example, the high frequency modulation signal can cause genes which otherwise are not expressed, or are inadequately expressed, to express or increase expression. In another example, gene expression associated with a particular abnormality can be down-regulated by the high frequency modulation signal.

Either or both of the foregoing mechanisms of action can have a cascading effect on other systems. For example, the effect of increasing gene expression and/or the network effect can be to increase metabolism, which in turn can increase hormone production, which in turn can affect the target organ. It is believed that, as a result of this indirect effect, the ultimate effect on the organ may not occur instantaneously, but rather may take time (e.g., days) to develop, in response to a modulation signal that is applied to the patient for over a similar period of time (e.g., days).

The effect of the high frequency modulation signal on the autonomic system can operate to decrease incontinence, improve digestion, reverse the effects of heart conditions that produce low cardiac output, normalize a patient's diabetic response, and/or reduce impotence, among other effects. In any of these or other embodiments, the effect may not be limited to increasing organ output or decreasing organ output, but may instead produce a normalized organ output, which may include increasing or decreasing output depending upon the initial state of the organ.

In at least some embodiments, a practitioner can obtain feedback from the patient to detect the effect of the high frequency modulation signal on the ANS, and, if necessary or desired, modify the signal delivery parameters to improve the effect. For example, the practitioner and/or the patient can directly observe/report changes in heart condition, diabetic response, pulmonary function, sexual function, and/or other functions. In other embodiments, the physician can more directly monitor and distinguish between effects on the sympathetic system and/or the parasympathetic system. Suitable products for monitoring these systems include those available from the Ansar Group, Inc. of Philadelphia, PA.

In at least some embodiments, the patient's ANS response to high frequency modulation signals may be correlated with the patient's pain response to such signals. Accordingly, detecting the patient's ANS response in accordance with any of the foregoing techniques can produce a supplemental or surrogate indication of the patient's pain response. This in turn can provide an alternate and in some cases more objective indication of the patient's pain response and/or response to other treatments for other ANS deficits.

5.0 Representative Examples

Embodiments of the presently disclosed technology are described in the following representative examples. A method for treating a patient in accordance with one example includes reducing or eliminating an autonomic system deficit of the patient by applying or directing application of an electrical signal to a spinal cord or spinal cord region of the patient, with the electrical signal having a frequency in a range of from about 1.5 kHz to about 100 kHz. In a further particular aspect of this example, reducing or eliminating the autonomic system deficit includes reducing or eliminating an imbalance between an effect of the patient's sympathetic system and an effect of the patient's parasympathetic system. In another aspect of this example, reducing or eliminating the autonomic system deficit includes normalizing a combined effect of the patient's sympathetic and parasympathetic systems. In still a further aspect, applying or directing application of the electrical signal includes applying or directing application of the signal to WDR neurons of the patient's spinal cord. In any of these examples, the autonomic system deficit can affect any of a number of representative target organs, including target organs of the patient's cardiovascular system and/or the patient's gastrointestinal system.

A method for treating a patient in accordance with another representative example includes implanting a signal delivery device at a location (e.g., an epidural location) proximate to the patient's spinal cord, based at least in part on an indication that the patient has an autonomic system deficit. The method can further include directing an electrical signal to the patient's spinal cord at a frequency in a range of from about 1.5 kHz to about 100 kHz (e.g., from about 3 kHz to about 20 kHz) to reduce or eliminate the autonomic system deficit. Reducing or eliminating the autonomic system deficit can include reducing or eliminating an imbalance between an effect of the patient's sympathetic system and an effect of the patient's parasympathetic system, and/or normalizing a combined effect of the patient's sympathetic and parasympathetic system. The electrical signal can be directed to WDR neurons of the patient's spinal cord and/or the dorsal horn of the patient's spinal cord. In further embodiments, the method can include monitoring the patient's autonomic system function, e.g., by observing a function of the patient controlled by the autonomic system and/or monitoring the patient with a medical device. In response to results obtained from monitoring the patient's autonomic system function, the method can further include adjusting at least one signal delivery parameter in accordance with which the electrical signal is applied to the patient's spinal cord.

Still a further representative example of a method in accordance with the present technology includes directing an electrical therapy signal to a patient's spinal cord to reduce or inhibit pain in the patient, with the electrical therapy signal having a frequency of from about 1.5 kHz to about 100 KHz. The method can further include receiving feedback corresponding to an autonomic system response by the patient to the electrical therapy signal, and, based at least in part on the feedback, identifying a characteristic of the patient's pain response to the electrical therapy signal. In particular embodiments, the electrical therapy signal is delivered without the electrical therapy signal causing paresthesia in the patient. In further particular embodiments, the method can include adjusting at least one signal delivery parameter in accordance with which the electrical therapy signal is directed to the patient's spinal cord, e.g., based at least in part on the feedback received from the patient.

The methods disclosed herein include and encompass, in addition to methods of making and using the disclosed devices and systems, methods of instructing others to make and use the disclosed devices and systems. For example, a method in accordance with a particular embodiment includes reducing or eliminating an autonomic system deficit of the patient by applying an electrical signal to a spinal cord of the patient, with the electrical signal having a frequency in a range of from about 1.5 kHz to about 100 kHz. A method in accordance with another embodiment includes instructing or directing such a method. Accordingly, any and all methods of use and manufacture disclosed herein also fully disclose and enable corresponding methods of instructing such methods of use and manufacture.

In still further examples, some or all of the foregoing method operations can be performed automatically by computer-based systems. Accordingly, embodiments of the present technology include computer-readable media and/or other non-transitory system components that are programmed or otherwise configured to perform such operations.

In still a further examples, there are provided methods for treating a patient's organ dysfunction resulting from an autonomic system deficit. The methods include applying a therapeutic signal to the patient's spinal cord so as to modulate (a) a sympathetic stimulation effect, (b) a parasympathetic effect, or (c) both a sympathetic effect and a parasympathetic effect on the target organ. Examples of target organs and corresponding sympathetic and parasympathetic effects are listed in FIG. 8. For example, methods are provided for treating a heart condition of the SA node, atria, AV node, Purkinje system, or ventricles by the application of a neuromodulation signal to the patient's spinal cord. At least a portion of the neuromodulation signal may have a frequency between about 1.5 kHz and 100 kHz, and may be applied at an amplitude such that the patient does not perceive paresthesia or any other uncomfortable stimulation sensations (i.e., the therapy signal does not generate paresthesia). Detailed examples of therapeutic signal parameters are provided above. The neuromodulation signal can thus modulate (a) a sympathetic stimulation effect, (b) a parasympathetic effect, or (c) both a sympathetic effect and a parasympathetic effect on the heart.

From the foregoing, it will be appreciated that specific embodiments of the technology have been described herein for purposes of illustration, but that various modifications may be made without deviating from the present disclosure. For example, therapies described in the context of particular vertebral locations to treat low back pain may be applied to other vertebral levels to treat other types of pain. In still further embodiments, the therapeutic effect can include indications in addition to or in lieu of pain. Methods and systems in accordance with particular embodiments of the present technology control autonomic system deficits via high frequency signals applied to the spinal cord, e.g., the WDR neurons and/or other dorsally located neural structures. In other embodiments, the signals can be applied to other neural populations, e.g., the dorsal root ganglia and/or peripheral nerves. Certain aspects of the disclosure described in the context of particular embodiments may be combined or eliminated in other embodiments. For example, patients can receive treatment at multiple vertebral levels and/or via leads or other signal delivery devices positioned at multiple locations. The foregoing mechanisms of action are believed to account for the patient responses observed during treatment in accordance with the presently disclosed technology; however, other mechanisms or processes may operate in addition to or in lieu of the foregoing mechanisms in at least some instances. Further, while advantages associated with certain embodiments have been described in the context of those embodiments, other embodiments may also exhibit such advantages, and not all embodiments need necessarily exhibit such advantages to fall within the scope of the present technology. Accordingly, the present disclosure and associated technology can encompass other embodiments not expressly shown or described herein.

I claim:

1. A method for regulating a patient's blood glucose levels, comprising:
    programming a signal generator to deliver a non-paresthesia producing electrical signal to the patient's spinal cord via at least one implanted signal delivery device,
    wherein the non-paresthesia producing electrical signal regulates the patient's blood glucose levels by modulating neurons of the patient's autonomic nervous system.

2. The method of claim 1 wherein modulating neurons of the patient's autonomic nervous system includes normalizing a combined effect of the patient's sympathetic and parasympathetic systems to regulate the patient's blood glucose levels.

3. The method of claim 1 wherein the non-paresthesia producing electrical signal modulates neurons of the patient's sympathetic nervous system.

4. The method of claim 3 wherein the non-paresthesia producing electrical signal inhibits neurons of the patient's sympathetic nervous system.

5. The method of claim 1 wherein modulating neurons of the patient's autonomic nervous system includes reducing or modifying organ dysfunction in the patient to regulate the patient's blood glucose levels.

6. The method of claim 5 wherein the implanted signal delivery device is positioned at a vertebral level associated with an organ responsible for the organ dysfunction in the patient.

7. The method of claim 6 wherein the vertebral level is an upper thoracic vertebral level.

8. The method of claim 6 wherein the vertebral level is a cervical vertebral level.

9. The method of claim 1 wherein the at least one implanted signal delivery device is positioned in an epidural space within the patient's spinal cord region.

10. The method of claim 1 wherein the non-paresthesia producing electrical signal has a frequency in a frequency range of from 1.5 kHz to 100 KHz.

11. The method of claim 1 wherein the non-paresthesia producing electrical signal has a frequency in a frequency range of from 5 KHz to 50 KHz.

12. The method of claim 1 wherein the non-paresthesia producing electrical signal has a frequency in a frequency range of from 5 kHz to 25 KHz.

13. The method of claim 1 wherein the non-paresthesia producing electrical signal has a frequency of 10 kHz.

14. The method of claim 1 wherein the non-paresthesia producing electrical signal has an amplitude in an amplitude range of from 0.1 mA to 20 mA.

15. The method of claim 1 wherein the non-paresthesia producing electrical signal has a pulse width in a pulse width range of from 25 microseconds to 166 microseconds.

16. The method of claim 1 wherein the non-paresthesia producing electrical signal has (i) a frequency in a frequency range of from 1.5 kHz to 100 KHz, (ii) an amplitude in an amplitude range of from 0.1 mA to 20 mA, and (iii) a pulse width in a pulse width range of from 25 microseconds to 166 microseconds.

17. The method of claim 1 wherein programming the implantable signal generator includes programming the implantable signal generator to deliver the non-paresthesia producing electrical signal in accordance with a duty cycle.

18. The method of claim 1 wherein programming the implantable signal generator is done in response to the patient having a disorder characterized by abnormal regulation of blood glucose levels.

19. The method of claim 1 wherein the signal generator is implantable.

20. A method for normalizing a patient's diabetic response, comprising:
    programming a signal generator to deliver a non-paresthesia producing electrical signal to the patient's spinal cord via at least one implanted signal delivery device,
    wherein the non-paresthesia producing electrical signal normalizes the patient's diabetic response by modulating neurons of the patient's autonomic nervous system.

21. The method of claim 20 wherein modulating neurons of the patient's autonomic nervous system includes normalizing a combined effect of the patient's sympathetic and parasympathetic systems to normalize the patient's diabetic response.

22. The method of claim 20 wherein the non-paresthesia producing electrical signal modulates neurons of the patient's sympathetic nervous system.

23. The method of claim 22 wherein the non-paresthesia producing electrical signal inhibits neurons of the patient's sympathetic nervous system.

24. The method of claim 22 wherein modulating neurons of the patient's autonomic nervous system includes reducing or modifying organ dysfunction in the patient to normalize the patient's diabetic response.

25. The method of claim 24 wherein the implanted signal delivery device is positioned at a vertebral level associated with an organ responsible for the organ dysfunction in patient.

26. The method of claim 25 wherein the vertebral level is an upper thoracic vertebral level.

27. The method of claim 25 wherein the vertebral level is a cervical vertebral level.

28. The method of claim 20 wherein the at least one implanted signal delivery device is positioned in an epidural space within the patient's spinal cord region.

29. The method of claim 20 wherein the non-paresthesia producing electrical signal has a frequency in a frequency range of from 1.5 kHz to 100 kHz.

30. The method of claim 20 wherein the non-paresthesia producing electrical signal has a frequency in a frequency range of from 5 kHz to 50 KHz.

31. The method of claim 20 wherein the non-paresthesia producing electrical signal has a frequency in a frequency range of from 5 kHz to 25 kHz.

32. The method of claim 20 wherein the non-paresthesia producing electrical signal has a frequency of 10 KHz.

33. The method of claim 20 wherein the non-paresthesia producing electrical signal has an amplitude in an amplitude range of from 0.1 mA to 20 mA.

34. The method of claim 20 wherein the non-paresthesia producing electrical signal has a pulse width in a pulse width range of from 25 microseconds to 166 microseconds.

35. The method of claim 20 wherein the non-paresthesia producing electrical signal has (i) a frequency in a frequency range of from 1.5 kHz to 100 kHz, (ii) an amplitude in an amplitude range of from 0.1 mA to 20 mA, and (iii) a pulse width in a pulse width range of from 25 microseconds to 166 microseconds.

36. The method of claim 20 wherein programming the implantable signal generator includes programming the implantable signal generator to deliver the non-paresthesia producing electrical signal in accordance with a duty cycle.

37. The method of claim 20 wherein programming the implantable signal generator is done in response to the patient having a disorder characterized by an abnormal diabetic response.

38. The method of claim 20 wherein the signal generator is implantable.

* * * * *